United States Patent
Prakash et al.

(10) Patent No.: US 9,144,251 B2
(45) Date of Patent: *Sep. 29, 2015

(54) HIGH-POTENCY SWEETENER COMPOSITION WITH MINERAL AND COMPOSITIONS SWEETENED THEREWITH

(75) Inventors: Indra Prakash, Alpharetta, GA (US); Grant E. DuBois, Roswell, GA (US)

(73) Assignee: The Coca-Cola Company, Atlanta, GA (US)

( * ) Notice: Subject to any disclaimer, the term of this patent is extended or adjusted under 35 U.S.C. 154(b) by 1188 days.

This patent is subject to a terminal disclaimer.

(21) Appl. No.: 11/556,058

(22) Filed: Nov. 2, 2006

(65) Prior Publication Data

US 2007/0116832 A1 May 24, 2007

Related U.S. Application Data

(60) Provisional application No. 60/739,302, filed on Nov. 23, 2005, provisional application No. 60/739,124, filed on Nov. 23, 2005, provisional application No. 60/805,216, filed on Jun. 19, 2006, provisional application No. 60/805,209, filed on Jun. 19, 2006.

(51) Int. Cl.

| | | |
|---|---|---|
| *A23L 1/236* | (2006.01) | |
| *A23L 2/60* | (2006.01) | |
| *A23G 3/36* | (2006.01) | |
| *A23G 4/06* | (2006.01) | |
| *A23G 9/32* | (2006.01) | |
| *A23L 1/22* | (2006.01) | |
| *A23L 1/304* | (2006.01) | |
| *A61K 33/06* | (2006.01) | |
| *A61K 33/24* | (2006.01) | |
| *A61K 33/26* | (2006.01) | |
| *A61K 33/30* | (2006.01) | |
| *A61K 45/06* | (2006.01) | |

(52) U.S. Cl.
CPC ... *A23L 2/60* (2013.01); *A23G 3/36* (2013.01); *A23G 3/362* (2013.01); *A23G 4/06* (2013.01); *A23G 4/064* (2013.01); *A23G 9/32* (2013.01); *A23G 9/325* (2013.01); *A23L 1/22075* (2013.01); *A23L 1/2364* (2013.01); *A23L 1/2366* (2013.01); *A23L 1/304* (2013.01); *A61K 33/06* (2013.01); *A61K 33/24* (2013.01); *A61K 33/26* (2013.01); *A61K 33/30* (2013.01); *A61K 45/06* (2013.01); *A23V 2002/00* (2013.01)

(58) Field of Classification Search
CPC ..... A23L 2/60; A23L 1/22075; A23L 1/2364; A23L 1/2366; A23L 1/304; A23G 3/36; A23G 3/362; A23G 4/06; A23G 4/064; A23G 9/32; A23G 9/325; A23V 2002/00; A61K 33/06; A61K 33/24; A61K 33/26; A61K 33/30; A61K 45/06
USPC .......................... 426/74, 548, 590
See application file for complete search history.

(56) References Cited

U.S. PATENT DOCUMENTS

| | | | |
|---|---|---|---|
| 4,551,342 A | 11/1985 | Nakel et al. | |
| 4,612,942 A | 9/1986 | Dobberstein et al. | |
| 5,433,965 A | 7/1995 | Fischer et al. | |
| 5,437,880 A * | 8/1995 | Takaichi et al. | 426/73 |
| 5,576,039 A | 11/1996 | Lewis | |
| 5,731,025 A | 3/1998 | Mitchell | |
| 5,962,678 A * | 10/1999 | Payzant et al. | 536/128 |
| 6,045,850 A | 4/2000 | Kondou | |
| 6,652,901 B2 | 11/2003 | Ishii | |
| 6,814,958 B1 * | 11/2004 | Sekimoto | 424/58 |
| 6,838,107 B1 | 1/2005 | Bakal et al. | |
| 7,067,150 B2 * | 6/2006 | Farber et al. | 424/488 |
| 7,074,438 B2 | 7/2006 | Xu | |
| 7,186,431 B1 | 3/2007 | Silver | |
| 7,267,835 B2 | 9/2007 | Kitazume et al. | |
| 7,531,192 B2 * | 5/2009 | Farber et al. | 424/488 |
| 7,815,956 B2 | 10/2010 | Lee et al. | |
| 7,851,005 B2 | 12/2010 | Bingley et al. | |

(Continued)

FOREIGN PATENT DOCUMENTS

| | | |
|---|---|---|
| AU | 2004202670 A1 | 1/2005 |
| EP | 0346866 A | 12/1989 |
| EP | 0470259 A1 | 2/1992 |
| EP | 0390299 B2 | 7/2000 |
| EP | 1629730 A | 3/2006 |

(Continued)

OTHER PUBLICATIONS

Geuns, Jan M.C., "Review: The safety of stevioside used as a sweetener", in Proceedings of the first symposium 'The Safety of Stevioside', p. 85-127 (2004).*

(Continued)

*Primary Examiner* — Leslie Wong
(74) *Attorney, Agent, or Firm* — King & Spalding

(57) ABSTRACT

The present invention relates generally to functional sweetener compositions comprising non-caloric or low-caloric natural and/or synthetic high-potency sweeteners and methods for making and using them. In particular, the present invention relates to different functional sweetener compositions comprising at least one non-caloric or low-caloric natural and/or synthetic high-potency sweetener, at least one sweet taste improving composition, and at least one functional ingredient, such as a mineral. The present invention also relates to functional sweetener compositions and methods that can improve the tastes of non-caloric or low-caloric high-potency sweeteners by imparting a more sugar-like taste or characteristic. In particular, the functional sweetener compositions and methods provide a more sugar-like temporal profile, including sweetness onset and sweetness linger, and/or a more sugar-like favor profile.

15 Claims, 5 Drawing Sheets

(56) References Cited

U.S. PATENT DOCUMENTS

| | | | |
|---|---|---|---|
| 2002/0132780 | A1 | 9/2002 | Heisey et al. |
| 2002/0197372 | A1 | 12/2002 | Janssen et al. |
| 2003/0035875 | A1* | 2/2003 | Dulebohn et al. ............ 426/548 |
| 2003/0124200 | A1 | 7/2003 | Stone |
| 2003/0152524 | A1 | 8/2003 | Eshita |
| 2003/0152684 | A1* | 8/2003 | Saito et al. .................... 426/548 |
| 2004/0022914 | A1 | 2/2004 | Allen |
| 2004/0058050 | A1 | 3/2004 | Guo |
| 2004/0120900 | A1 | 6/2004 | Arsenault |
| 2004/0237663 | A1 | 12/2004 | Faber et al. |
| 2005/0214412 | A1 | 9/2005 | Koo et al. |
| 2006/0093720 | A1 | 5/2006 | Tatz |
| 2007/0003679 | A1 | 1/2007 | Shimizu et al. |
| 2007/0031561 | A1 | 2/2007 | Lakkis et al. |
| 2007/0082103 | A1 | 4/2007 | Magomet et al. |
| 2009/0202697 | A1 | 8/2009 | Erickson et al. |

FOREIGN PATENT DOCUMENTS

| | | | |
|---|---|---|---|
| JP | 59183670 | A | 10/1984 |
| JP | 60075252 | A2 | 4/1985 |
| JP | 60188035 | A | 9/1985 |
| JP | 62-079752 | | 4/1987 |
| JP | 62091161 | A | 4/1987 |
| JP | 63-258557 | | 10/1988 |
| JP | 63304964 | A2 | 12/1988 |
| JP | H02-261359 | | 10/1990 |
| JP | 03-251160 | A | 11/1991 |
| JP | 04091753 | A2 | 3/1992 |
| JP | 06191944 | A | 7/1994 |
| JP | 06192283 | A | 7/1994 |
| JP | 731407 | A | 2/1995 |
| JP | 07143860 | A | 6/1995 |
| JP | 08000214 | A | 1/1996 |
| JP | 08089207 | A | 4/1996 |
| JP | 09104625 | A2 | 4/1997 |
| JP | 09173009 | A2 | 7/1997 |
| JP | 09194370 | A2 | 7/1997 |
| JP | 1094382 | A | 4/1998 |
| JP | 10150958 | A | 6/1998 |
| JP | 10276712 | A | 10/1998 |
| JP | 10-304829 | | 11/1998 |
| JP | 11123069 | A | 5/1999 |
| JP | 11243906 | | 9/1999 |
| JP | 11302142 | A | 11/1999 |
| JP | 11-346708 | | 12/1999 |
| JP | 2000-004836 | | 1/2000 |
| JP | 2000037170 | A | 2/2000 |
| JP | 2000037178 | A | 2/2000 |
| JP | 2000236842 | | 9/2000 |
| JP | 2000300190 | A | 10/2000 |
| JP | 2001161308 | A2 | 6/2001 |
| JP | 2003180288 | | 7/2003 |
| JP | 2003210147 | A | 7/2003 |
| JP | 2004149481 | | 5/2004 |
| JP | 2004073197 | | 11/2004 |
| JP | 2005237303 | | 9/2005 |
| WO | WO 94/08471 | A | 4/1994 |
| WO | WO 94/18855 | A | 9/1994 |
| WO | WO 98/04156 | | 2/1998 |
| WO | WO 00/24273 | | 5/2000 |
| WO | WO 00/62628 | | 10/2000 |
| WO | WO 02/087358 | A1 | 11/2002 |
| WO | WO 2004/089113 | A | 10/2004 |

OTHER PUBLICATIONS

Sasaki, Kazuhito, "Application of Stevia Sweetener to Soft Drinks," *New Food Ind.*, 1983, pp. 38-43, vol. 25 No. 4, Sanyo Kokusaku Pulp Co. Ltd., Japan.

Kohda, Hiroshi, et al., "New Sweet Diterpene Glucosides from Stevia Rebaudiana," *Phytochemistry*, 1976, pp. 981-983, vol. 15 No. 6, School of Medicine, Hiroshima Univ., Hiroshima, Japan.

Nabors, Lyn O'Brien, et. al., "Alternative Sweeteners," *Food Science and Technology*, 1985, pp. 295-307, vol. 17, Marcel Dekker, Inc., New York, NY, USA.

"SteviaClear™ Liquid Stevia," Jun. 2005, Advertisement.

Abudula, Reziwanggu, et al., "Rebaudioside A Potently Stimulates Insulin Secretion from Isolated Mice Islets: Studies on the Dose-Glucose-, and Calcium-Dependency," *Metabolism*, Oct. 2004, vol. 53 No. 10, Arhus University Hospital, Arhus, Denmark.

Mizutani, Kenji, et al., "Use of Stevia Rebaudiana Sweeteners in Japan," *Stevia: The Genus Stevia*, 2002, pp. 178-195, A. Douglas Kinghorn, ed., Taylor and Francis, Inc., New York, NY, USA.

Kim, Jinwoong, et al., "Use of Stevioside and Cultivation of Stevia Rebaudiana in Korea," *Stevia: The Genus Stevia*, 2002, pp. 196-202, A. Douglas Kinghorn, ed., Taylor and Francis, Inc., New York, NY, USA.

Chang, Shin S., et al., "Stability Studies of Stevioside and Rebaudioside A in Carbonated Beverages," *J. Agri. Food. Chem.*, 1983, pp. 409-412., vol. 31, American Chemical Society, USA.

Goettemoeller, Jeffrey, "Stevia Sweet Recipes: Sugar Free—Naturally!" 1998, pp. 1-17, Vital Health Publishing, Bloomingdale, Illinois, USA.

Depuydt, Rita, "Baking with Stevia 11," 1998, pp. 5-6, 9-10, 15, 104, Sun Coast Enterprises, Oak View, California, USA.

The Ministry of Health and Welfare, Food Chemical Department, "List of Food Additives excluding chemical synthetics," 1989, The Government of Japan, Tokyo, Japan.

Geuns, Jan M. C., "Review: The Safety of Stevioside used as a Sweetener," in Proceedings of the first symposium, 'The Safety of Stevioside,' 2004, pp. 85-127, Laboratory of Functional Biology, KULeuven, Leuven, Belgium.

Food Standards Australia New Zealand, "Draft Assessment Report, Application A540, Steviol Glycosides as Intense Sweeteners," 2007, Canberra, Australia.

Sunrider Product Catalog, Apr. 1994, pp. 3, 5, The Sunrider Corporation, Torrance, CA, USA.

Sunrider Product Catalog, Apr. 1999, pp. 1-2, The Sunrider Corporation, Torrance, CA, USA.

Sunrider Product Catalog, Apr. 2000, pp. 1-2, The Sunrider Corporation, Torrance, CA, USA.

Sunrider Product Catalog, Jan. 2001, pp. 1, 12-13, The Sunrider Corporation, Torrance, CA, USA.

Sunrider Product Catalog, Jan. 2002, pp. 6-7, 18-19, The Sunrider Corporation, Torrance, CA, USA.

Sunrider Product Catalog, May 2003, pp. 10-11, 18-19, The Sunrider Corporation, Torrance, CA, USA.

Sunrider Product Catalog, Feb. 2005, pp. 7-8, 21-22, The Sunrider Corporation, Torrance, CA, USA.

Sunrider Product Catalog, 2006, pp. 7-8, 21-22, The Sunrider Corporation, Torrance, CA, USA.

Sunrider Product Catalog, 2007, pp. 8-9, 14-15, The Sunrider Corporation, Torrance, CA, USA.

The Sunrider Corporation, "Delicious Nutritious Whole Food Sunrider Recipes," 2004, http://healthregeneration.com/recipes.html.

The Sunrider Corporation, VitaFruit product advertising flyer, 1994, Torrance, CA, USA.

Sunwriter Newsletter, "The Truth About Trusweet," Jul. 1983, p. 2, The Sunrider Corporation, Torrance, CA, USA.

Sunwriter Newsletter, "The Truth About Trusweet," Apr. 1984, p. 2, The Sunrider Corporation, Torrance, CA, USA.

The SunSpot Newsletter, "SunCare is Available," May 1985, p. 2, The Sunrider Corporation, Torrance, CA, USA.

The SunSpot Newsletter, Jan. 1988, pp. 1-2, The Sunrider Corporation, Torrance, CA, USA.

The SunSpot Newsletter, Nov. 1993, pp. 1-2, vol. 11, No. 11, The Sunrider Corporation, Torrance, CA, USA.

The SunSpot Newsletter, Dec. 1993, pp. 1-2, vol. 11, No. 12, The Sunrider Corporation, Torrance, CA, USA.

The SunSpot Newsletter, Mar. 1995, pp. 1, 3, vol. 13, No. 3, The Sunrider Corporation, Torrance, CA, USA.

Sunwriter Newsletter, "Sunectar," Holiday Issue 1995, vol. 12, No. 5, The Sunrider Corporation, Torrance, CA, USA.

(56) References Cited

OTHER PUBLICATIONS

Sunwriter Newsletter, "Sunnydew," May/Jun. 1996, vol. 13, No. 3, The Sunrider Corporation, Torrance, CA, USA.
Sunwriter Newsletter, Sep./Oct. 1996, vol. 13, No. 5, The Sunrider Corporation, Torrance, CA, USA.
The SunSpot Newsletter, "VitaSpray," Sep. 1996, vol. 14, No. 9, The Sunrider Corporation, Torrance, CA, USA.
The SunSpot Newsletter, pp. 1-2, Nov. 1996, vol. 14, No. 10, The Sunrider Corporation, Torrance, CA, USA.
The SunSpot Newsletter, pp. 1-2, Aug. 1997, vol. 15, No. 8, The Sunrider Corporation, Torrance, CA, USA.
The SunSpot Newsletter, pp. 1-2, May 1998, vol. 16, No. 5, The Sunrider Corporation, Torrance, CA, USA.
The SunSpot Newsletter, pp. 1-3, Jul. 1998, vol. 16, No. 7, The Sunrider Corporation, Torrance, CA, USA.
The SunSpot Newsletter, pp. 1-2, Oct. 1998, vol. 16, No. 10, The Sunrider Corporation, Torrance, CA, USA.
The SunSpot Newsletter, pp. 1, 4, Mar. 1999, vol. 18, No. 3, The Sunrider Corporation, Torrance, CA, USA.
The SunSpot Newsletter, pp. 1-2, Jan. 1999, vol. 18, No. 1, The Sunrider Corporation, Torrance, CA, USA.
Sunwriter Newsletter, pp. 12, 14, 1999, vol. 16, No. 1, The Sunrider Corporation, Torrance, CA, USA.
The SunSpot Newsletter, pp. 1-2, Mar. 2000, vol. 19, No. 3, The Sunrider Corporation, Torrance, CA, USA.
The SunSpot Newsletter, pp. 1, 4, Oct. 2000, vol. 19, No. 10, The Sunrider Corporation, Torrance, CA, USA.
The SunSpot Newsletter, pp. 1-2, Apr. 2001, vol. 20, No. 4, The Sunrider Corporation, Torrance, CA, USA.
The SunSpot Newsletter, pp. 1-2, Jun. 2002, vol. 21, No. 6, The Sunrider Corporation, Torrance, CA, USA.
The SunSpot Newsletter, pp. 1-2, Oct. 2002, vol. 21, No. 10, The Sunrider Corporation, Torrance, CA, USA.
Director Update Newsletter, "Sunrider VitaFruit Liquid Concentrate," Nov. 1993, The Sunrider Corporation, Torrance, CA, USA.
Director Update Newsletter, Dec. 1993, The Sunrider Corporation, Torrance, CA, USA.
Director Update Newsletter, Jun. 1994, The Sunrider Corporation, Torrance, CA, USA.
Director Update Newsletter, Dec. 1994, The Sunrider Corporation, Torrance, CA, USA.
Director Update Newsletter, Apr. 1995, The Sunrider Corporation, Torrance, CA, USA.
Director Update Newsletter, Jun. 1995, The Sunrider Corporation, Torrance, CA, USA.
Director Update Newsletter, Jul. 1995, The Sunrider Corporation, Torrance, CA, USA.
Director Update Newsletter, Nov. 1995, The Sunrider Corp., Torrance, CA, USA.
Director Update Newsletter, Dec. 1995, The Sunrider Corporation, Torrance, CA, USA.
Director Update Newsletter, Feb. 1996, The Sunrider Corporation, Torrance, CA, USA.
Director Update Newsletter, May 1996, The Sunrider Corporation, Torrance, CA, USA.
Director Update Newsletter, Jun. 1996, The Sunrider Corporation, Torrance, CA, USA.
Director Update Newsletter, Jul. 1996, The Sunrider Corporation, Torrance, CA, USA.
Director Update Newsletter, Aug. 1996, The Sunrider Corporation, Torrance, CA, USA.
Director Update Newsletter, Sep. 1996, The Sunrider Corporation, Torrance, CA, USA.
Director Update Newsletter, Nov. 1996, The Sunrider Corporation, Torrance, CA, USA.
Director Update Newsletter, Feb. 2000, The Sunrider Corporation, Torrance, CA, USA.
Director Update Newsletter, Nov. 2001, The Sunrider Corporation, Torrance, CA, USA.
Director Update Newsletter, Aug. 2003, The Sunrider Corporation, Torrance, CA, USA.
Director Update Newsletter, Nov. 2004, The Sunrider Corporation, Torrance, CA, USA.
Director Update Newsletter, Aug. 2005, The Sunrider Corporation, Torrance, CA, USA.
The Sunrider Corporation, Trusweet Extract product packaging, 1982, Torrance, CA, USA.
The Sunrider Corporation, Sunectar Dietary Supplement product label, 1995, 1996, 2002, 2003, Torrance, CA, USA.
Sunrider International, SunCare Natural Facial Masque product label, 1989, 1990, 1991, 1992, 1994, 1995, Torrance, CA, USA.
Sunrider International, SunCare Herbal Skincare product label, 1991, 1993, 1992, 1995, Torrance, CA, USA.
The Sunrider Corporation, VitaFruit Lemon Liquid Herb Fruit Concentrate product label, 1993, 1994, 1995, 1996, 1997, 2000, 2001, 2002, 2003, 2006, Torrance, CA, USA.
The Sunrider Corporation, VitaSpray Dietary Supplement product label, Dec. 2002, Torrance, CA, USA.
The Sunrider Corporation, Sunnydew Dietary Supplement product label, Jun. 1999, 2002, 2003, 2006, Torrance, CA, USA.
The Sunrider Corporation, SunSmile Tabs product label, 1998, Torrance, CA, USA.
The Sunrider Corporation, Herbal Cal Tab Dietary Supplement product label, 1999, 2000, 2001, 2002, 2003, Torrance, CA, USA.
The Sunrider Corporation, Calli product label, 1983, Torrance, CA, USA.
The Sunrider Corporation, Alpha 20C product label, 1999, 2000, Torrance, CA, USA.
The Sunrider Corporation, Sunrise product label, 1999.
The Sunrider Corporation, Evergreen product label, 2000.
The Sunrider Corporation, Quinary product label, year not indicated.
The Sunrider Corporation, Fortune Delight product label, Mar. 2003, Torrance, CA, USA.
The Sunrider Corporation, NuPlus product label, 2002, 2003, Torrance, CA, USA.
Adechy, Miriam, "International Search Report and Written Opinion of the International Searching Authority," Apr. 11, 2007 , PCT/US2006/044574, European Patent Office, Rijswijk, The Netherlands.
Georgopoulos, N., "International Search Report and Written Opinion of the International Searching Authority," Mar. 14, 2007, PCT/US2006/044518, European Patent Office, Rijswijk, The Netherlands.
Couzy, Francois, "International Search Report and Written Opinion of the International Searching Authority," Mar. 22, 2007, PCT/US2006/044724, European Patent Office, Rijswijk, The Netherlands.
Couzy, Francois, "International Search Report and Written Opinion of the International Searching Authority," Jun. 22, 2007, PCT/US2006/044802, European Patent Office, Rijswijk, The Netherlands.
Popa, Marian, "International Search Report and Written Opinion of the International Searching Authority," May 11, 2007, PCT/US2006/044592, European Patent Office, Rijswijk, The Netherlands.
Ipinazar, Paula, "Partial International Search Report of the International Searching Authority," Apr. 2007, PCT/US2006/044600, European Patent Office, Rijswijk, The Netherlands.
Heirbaut, Marc, "International Search Report and Written Opinion of the International Searching Authority," Oct. 31, 2007, PCT/US2006/044513, European Patent Office, Rijswijk, The Netherlands.
Smeets, Dieter, "International Search Report and Written Opinion of the International Searching Authority," Apr. 10, 2007, PCT/US2006/044785, European Patent Office, Rijswijk, The Netherlands.
Couzy, Francois, "International Search Report and Written Opinion of the International Searching Authority," Mar. 23, 2007, PCT/US2006/044727, European Patent Office, Rijswijk, The Netherlands.
Couzy, Francois, "International Search Report and Written Opinion of the International Searching Authority," Mar. 21, 2007, PCT/US2006/044591, European Patent Office, Rijswijk, The Netherlands.
Georgopoulos, N., "International Search Report and Written Opinion of the International Searching Authority," Jun. 13, 2007, PCT/US2006/044599, European Patent Office, Rijswijk, The Netherlands.
Popa, Marian, "International Search Report and Written Opinion of the International Searching Authority," May 4, 2007, PCT/US2006/044577, European Patent Office, Rijswijk, The Netherlands.

(56) References Cited

OTHER PUBLICATIONS

Popa, Marian, "International Search Report and Written Opinion of the International Searching Authority," Mar. 15, 2007, PCT/US2006/044783, European Patent Office, Rijswijk, The Netherlands.
Donovan-Beerman, T., "International Search Report and Written Opinion of the International Searching Authority," Mar. 30, 2007, PCT/US2006/044573, European Patent Office, Rijswijk, The Netherlands.
Popa, Marian, "International Search Report and Written Opinion of the International Searching Authority," Mar. 16, 2007, PCT/US2006/044705, European Patent Office, Rijswijk, The Netherlands.
Groh, Bjorn, "International Search Report and Written Opinion of the International Searching Authority," Oct. 24, 2007, PCT/US2006/044803, European Patent Office, Rijswijk, The Netherlands.
Smeets, Dieter, "International Search Report and Written Opinion of the International Searching Authority," Apr. 3, 2007, PCT/US2006/044590, European Patent Office, Rijswijk, The Netherlands.
Groh, Bjorn, "International Search Report and Written Opinion of the International Searching Authority," Apr. 16, 2007, PCT/US2006/044706, European Patent Office, Rijswijk, The Netherlands.
Couzy, Francois, "International Search Report and Written Opinion of the International Searching Authority," Apr. 13, 2007, PCT/US2006/044703, European Patent Office, Rijswijk, The Netherlands.
Rinaldi, Francesco, "International Search Report and Written Opinion of the International Searching Authority," Mar. 20, 2007, PCT/US2006/044798, European Patent Office, Rijswijk, The Netherlands.
Hartlieb, Ariane, "International Search Report and Written Opinion of the International Searching Authority," Aug. 21, 2007, PCT/US2006/044801, European Patent Office, Rijswijk, The Netherlands.
Hicks, K., et. al., "Phytosterols and Phytostanols: Functional Food Cholesterol Busters," *Food Technology*, Jan. 1, 2001, pp. 63-67, vol. 55, No. 1, Inst. of Food Technologists, Chicago, IL, USA.
Sardesai, V. M., et. al., "Natural and Synthetic Intense Sweeteners," *Journal of Nutritional Biochemistry*, May 1991, pp. 236-244, vol. 2, No. 5, Butterworth Publishers, Stoneham, Great Britain.
Schiffman, S., et. al., "Investigation of Synergism in Binary Mixtures of Sweeteners," *Brain Research Bulletin*, 1995, pp. 105-120, vol. 38, No. 2, XP002428872.
Moriyama, et. al., "Soybean beta-conglycinin diet suppresses serun triglyceride levels in normal and genetically obese mice by induction of beta-oxidation, down regulation of fatty acid synthase, and inhibition of triglyceride absorption," *Bioscience, Biotechnology, and Biochemistry*, Dec. 2004, pp. 352-359, vol. 26, No. 6, XP018001511.
Nojiri, S., et. al., "Determination of sugar alcohols in confectionaries by high-performance liquid chromatography after nitrobenzoylation," Journal of Chromatography, Sep. 29, 2000, pp. 195-200, vol. 893, No. 1, Elsevier Science Publishers, B.V., Amsterdam, The Netherlands.
Abad, M. J., et. al., "Anti-Inflammatory Activity of two flavonoids from Tanacetum microphyllum," Journal of Natural Products, 1993, pp. 1164-1167, vol. 56, No. 7, Biosciences Information Service, Philadelphia, PA, USA.
Anon., "Sweet tasting amino acid, glycine, enhances flavor and provides functional properties," Food Processing USA, 1983, p. 90, vol. 44, No. 7, International Food Information Service, Frankfurt-Main, Germany.
Shamala, T. R., et. al., "Honey—it is more than just sweet," Indian Food Industry, 1999, pp. 349-357, vol. 18, No. 6, Dept. of Food Microbiology, Central Food Technology, Research Institute, Mysore, India.
Rajbhandari, A., "The Flavonoids of Stevia Rebaudiana," J. Nat. Prod., 1983, pp. 194-195, vol. 46, No. 2.
Geuns, Jan M. C., "Stevioside," Phytochemistry, Nov. 2003, pp. 913-921, vol. 64, No. 5, Pergamon Press, Great Britain.
Schiffman, S., et. al., "Synergism among ternary mixtures of fourteen sweeteners," Chemical Senses, 2000, pp. 131-140, vol. 25, IRL Press, Oxford, Great Britain.
Franke, S. I. R., et. al., "Influence of orange juice over the genotoxicity induced by alkylating agents: an in vivo analysis," Mutagenesis, Jun. 14, 2005, pp. 279-283, vol. 20, No. 4, IRL Press, Oxford, Great Britain.
Losada, M., et. al., "Toward a healthier diet for the colon: The influence of fructooligosaccharides and lactobacilli on intestinal health," Jan. 2002, Biosciences Information Service, Philadelphia, PA, USA.
Grenby, T. H., "Intense Sweeteners for the Food Industry: An Overview," *Trends in Food Science and Technology*, Jan. 1991, pp. 2-6, vol. 2, No. 1, Elsevier Science Publishers, Great Britain.
N. N., "Rebaudioside A and Stevia Extract," retrieved from the Internet on Mar. 16, 2007, pp. 1-5, http://emperorsherbologist.com/rabaudioside_a.php.
Anon., "Sugar-free Cake Mix Preparation by combining maltoligosyl-sucrose, sorbitol, and Stevia extract with glycine and/or DL-alanine," WPI/Thomson, Nov. 10, 1981, XP002425501.
Schiffman, Susan S., et al., "Selective Inhibition of Sweetness by Na-PMP," Apr. 26, 1999, pp. 439-437, Oxford University Press.
International Food Information Council, "Question and Answers About Functional Foods," IFIC (2006).
International Food Information Council, Background on functional foods, IFIC (2004).
Issue Paper, "Nutraceuticals for Health Promotion and Disease Prevention," Council for Agricultural Science & Technology, 24: 1-16 (Oct. 2003).
Jones, P., "Clinical nutrition: 7. functional foods—more than just nutrition," CMAJ, 166(12): 1555 1563 (2002).
Koletsko, et al., "Growth, development and differentiation: a functional food science approach," British Jour. Nutr., 80 (Suppl. 1): S5-S45 (1998).
Webb, G., "Dietary Supplements & Functional Foods," CRC Press, pp. 1-21 (2006).
Couzy, Francois, "International Search Report and Written Opinion of the International Searching Authority," Aug. 31, 2007, PCT/US2006/044576, European Patent Office, Rijswijk, The Netherlands.
Tadhani, M. and Subhash, R., "Preliminary studies on Stevia rebaudiana leaves: proximal composition, mineral analysis and phytochemical screening," J. Med. Sci. 6(3): 321-326 (2006).
Heirbaut, Marc, "International Search Report and Written Opinion of the International Searching Authority," Jan. 2, 2008, PCT/US2006/044797, European Patent Office, Rijswijk, The Netherlands.
Heirbaut, Marc, "International Search Report and Written Opinion of the International Searching Authority," Jan. 2, 2008, PCT/US2006/044725, European Patent Office, Rijswijk, The Netherlands.
Webb, Dietary Supplements and Functional Foods, 84-106, Blackwell Publishing, UK (2006).
Dietary Reference Intakes (DRIs): Recommended Intakes for Individuals, Vitamins, Food and Nutrition Board, Institute of Medicine, National Academies, USDA Natural Agricultural library, http://www.iom.edu/Object.File/Master/21/372/0.pdf.
Dietary Reference Intakes: Electrolytes and Water, USDA Natural Agricultural Library, http://www.iom.edu/Object.File/Master/20/004/0.pdf.
Dietary Reference Intakes: Elements, USDA Natural Agricultural Library, http://www.iom.edu/Object.File/Master/7/294/0.pdf.
Dietary Mineral, Wikipedia, http://en.wikipedia,org/wiki/Dietary_mineral.
Mineral, Wikipedia, http://en.wikipedia,org/wiki/mineral.
Mineral Deficiency, HealthAtoZ.com http://www.healthatoz.com/healthatoz/Atoz/common/standard/transform.jsp?requestURI=/healthatoz/Atoz/ency/mineral_deficiency.jsp.
Jasti, Minerals, http://www.faqs.org/nutrition/Met-Obe/Minerals.html, 2006, Thompson Gale.
Brody, Uretsky, Gale, Minerals Health Article, http://www.healthline.com/galecontents/minerals-1, 2006 Encyclopedia of Children's Health.
Parpinello, G. P. et al., "Stevioside as a replacement of sucrose in peach juice: sensory evaluation", *Journal of Sensory Studies* 2001, vol. 16, pp. 471-484.
Schiffman, S. S. et al., "Effect of repeated presentation on sweetness intensity of binary and ternary mixtures of sweeteners", *Chemical Senses* 2003, vol. 28, pp. 219-229.

(56) References Cited

OTHER PUBLICATIONS

Schiffman, S. S. et al., "Synergism among ternary mixtures of fourteen sweeteners", *Chemical Senses* 2000, vol. 25, pp. 131-140.

Yang, et al. "Studies on the Separation of Rebaudioside A by Recrystallization," *Ion Exchange and Absorption* 1998, vol. 14 (6), pp. 515-520 (English Abstract).

Morita Kagaku Kogyo Co., Ltd., The rebaudio A9 series, http://www.morita-kagaku-kogyo.co.jp/a9.htm.

Morita Kagaku Kogyo Co., Ltd., The rebaudio J series, http://www.morita-kagaku-kogyo.co.jp/j.htm.

Kinghorn, A. D. "Discovery of Terpenoid and Phenolic Sweeteners From Plants" 2002, vol. 74, No. 7, pp. 1169-1179.

Hirata, K. et al. "Analysis of Stevia Glycosides in Stevia Products of Natural Sweetening and Evaluation of their Chemical Quality", Ann. Rep. Tokyo Metr. Res. Lab. P.H., vol. 53, pp. 108-112, 2002.

Morita Kagaku Kogyo Co., Ltd., The rebaudio A9 series, http://www.morita-kagaku-kogyo.co.jp/a9.htm, no date.

Morita Kagaku Kogyo Co., Ltd., The rebaudio J series, http://www.morita-kagaku-kogyo.co.jp/j.htm, no date.

* cited by examiner

HIGH-POTENCY SWEETENER COMPOSITION WITH MINERAL AND COMPOSITIONS SWEETENED THEREWITH

RELATED APPLICATION DATA

The present application claims priority under 35 U.S.C. §119 to U.S. Provisional Application No. 60/739,302, entitled "Natural High-Potency Sweetener Compositions With Improved Temporal Profile And/Or Flavor Profile, Methods For Their Formulations, and Uses," filed on Nov. 23, 2005; U.S. Provisional Application No. 60/739,124, entitled "Synthetic Sweetener Compositions With Improved Temporal Profile And/Or Flavor Profile, Methods For Their Formulations, and Uses," filed on Nov. 23, 2005; U.S. Provisional Application No. 60/805,209, entitled "Natural High-Potency Tabletop Sweetener Compositions with Improved Temporal and/or Flavor Profiles, Methods for Their Formulation, and Uses," filed on Jun. 19, 2006; and U.S. Provisional Application No. 60/805,216, entitled "Rebaudioside A Composition and Method for Purifying Rebaudioside A," filed on Jun. 19, 2006. These applications are hereby incorporated by reference in their entirety.

FIELD OF THE INVENTION

The present invention relates generally to a functional sweetener and orally ingestible compositions containing same.

BACKGROUND OF THE INVENTION

Nutrition usually focuses on the relationship between food and human health from the perspective of ensuring all essential nutrients are adequately supplied and utilized to optimize health and well being. As diseases typically related to nutritional deficiency were managed, there has been a recognition that many nutrients have health benefits beyond basic nutrition. Accordingly, functional ingredients have been identified as playing a key role in an individual's overall health.

"Functional ingredients" offer potential health benefits beyond basic nutrition when incorporated into foods, beverages, and other orally ingested products. Such ingredients have been shown to help reduce the risk of or manage a number of health concerns, including cancer, heart and cardiovascular disease, gastrointestinal health, menopausal symptoms, osteoporosis, and vision. Since 1993, the United States Food and Drug Administration (FDA) has approved numerous health claims for the labeling of food products with information related to the health benefits of functional food (U.S. Food and Drug Administration, *A Food Labeling Guide* (2000)).

| Functional Food | Health Benefit |
| --- | --- |
| Potassium Diets low in sodium | Reduced risk of high blood pressure and stroke |
| Plant sterol and stanol esters Soy protein Fruits, vegetables, and grain products that contain fiber, particularly soluble fiber Diets low in dietary saturated fat and cholesterol | Reduced risk of coronary heart disease |
| Calcium | Reduced risk of osteoporosis |
| Fruits, vegetables, and fiber-containing grain products Diets low in dietary fat | Reduced risk of cancer |
| Folate | Reduced risk of neural tube birth defects |
| Dietary sugar alcohol | Reduced risk of dental caries (cavities) |

Although not yet approved by the FDA for the purposes of labeling, numerous other functional foods are believed to provide health benefits beyond those listed above, such as reduced inflammation.

Functional ingredients generally are classified into categories such as carotenoids, dietary fiber, fatty acids, flavonoids, isothiocyanates, phenols, plant sterols and stanols (phytosterols and phytostanols); polyols; prebiotics/probiotics; phytoestrogens; soy protein; sulfides/thiols; amino acids; proteins; vitamins; and minerals. Functional ingredients also may be classified based on their health benefits, such as cardiovascular, cholesterol-reducing, and anti-inflammatory.

Health trends also have promoted an increased use of non-caloric high-potency sweeteners in consumer diets. Although natural caloric sweetener compositions, such as sucrose, fructose, and glucose, provide the most desirable taste to consumers, they are caloric. Numerous natural and synthetic high-potency sweeteners are non-caloric; however, they exhibit sweet tastes that have different temporal profiles, maximal responses, flavor profiles, mouthfeels, and/or adaptation behaviors than that of sugar.

For example, the sweet tastes of natural and synthetic high-potency sweeteners are slower in onset and longer in duration than the sweet taste produced by sugar and thus change the taste balance of a food composition. Because of these differences, use of natural and synthetic high-potency sweeteners to replace a bulk sweetener, such as sugar, in a food or beverage, causes an unbalanced temporal profile and/or flavor profile. In addition to the difference in temporal profile, high-potency sweeteners generally exhibit (i) lower maximal response than sugar, (ii) off tastes including bitter, metallic, cooling, astringent, licorice-like taste, etc., and/or (iii) sweetness which diminishes on iterative tasting. It is well known to those skilled in the art of food/beverage formulation that changing the sweetener in a composition requires re-balancing of the flavor and other taste components (e.g., acidulants). If the taste profile of natural and synthetic high-potency sweeteners could be modified to impart specific desired taste characteristics to be more sugar-like, the type and variety of compositions that may be prepared with that sweetener would be expanded significantly. Accordingly, it would be desirable to selectively modify the taste characteristics of natural and synthetic high-potency sweeteners.

It also would be desirable to improve the taste of ingestible compositions that include functional ingredients to promote their use and the resulting health benefits.

SUMMARY OF THE INVENTION

Generally, this invention addresses the above described need by providing a functional sweetener composition having improved temporal profile and/or flavor profile and a method for improving the temporal profile and/or flavor profile of a functional sweetener composition. In another particular embodiment, this invention provides a functional sweetened composition comprising a sweetenable composition in combination with a functional sweetener composition having an improved temporal profile and/or flavor profile, and a method for improving the temporal profile and/or flavor profile of the functional sweetened composition. In particular, this invention improves the temporal profile and/or flavor profile by imparting a more sugar-like temporal profile and/or flavor profile. More particularly, this invention comprises a functional sweetener composition or a functional sweetened composition comprising at least one mineral; at least one high-potency sweetener; and at least one sweet taste improving composition.

Objects and advantages of the invention will be set forth in part in the following description, or may be obvious from the description, or may be learned through practice of the invention. Unless otherwise defined, all technical and scientific terms and abbreviations used herein have the same meaning as commonly understood by one of ordinary skill in the art to which this invention pertains. Although methods and compositions similar or equivalent to those described herein can be used in practice of the present invention, suitable methods and compositions are described without intending that any such methods and compositions limit the invention herein.

DETAILED DESCRIPTION OF THE INVENTION

Figure 1:
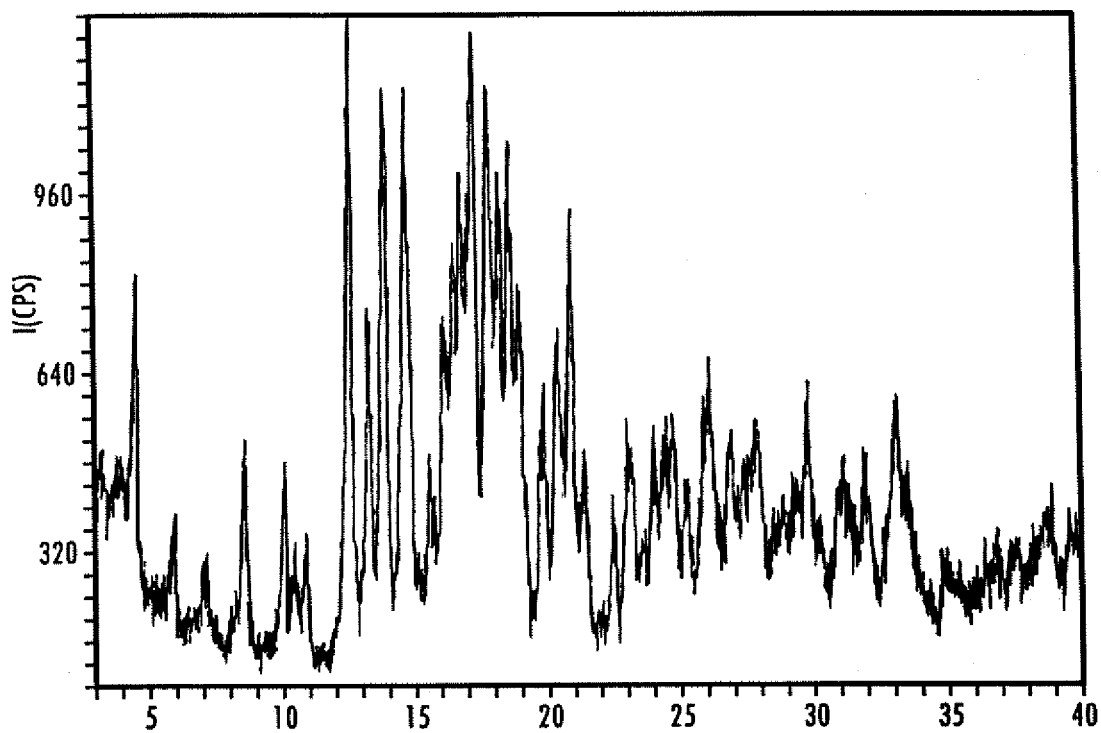
FIG. 1 is a powder x-ray diffraction scan of rebaudioside A polymorph Form 1 on a plot of the scattering intensity versus the scattering angle 2θ in accordance with an embodiment of this invention.

Reference now will be made in detail to the presently proffered embodiments of the invention. Each example is provided by way of explanation of embodiments of the invention, not limitation of the invention. In fact, it will be apparent to those skilled in the art that various modifications and variations can be made in the present invention without departing from the spirit or scope of the invention. For instance, features illustrated or described as part of one embodiment, can be used on another embodiment to yield a still further embodiment. Thus, it is intended that the present invention cover such modifications and variations within the scope of the appended claims and their equivalents.

Embodiments of this invention include functional sweetener compositions and functional sweetened compositions comprising at least one natural and/or synthetic high-potency sweetener, at least one sweet taste improving composition, and at least one functional ingredient. Also embodied in this invention are methods for making functional sweetener compositions and functional sweetened compositions.

I. Functional Ingredients

In a particular embodiment, a sweetener composition comprises at least one natural and/or synthetic high-potency sweetener, at least one sweet-taste improving composition, and at least one functional ingredient. The functional ingredient desirably comprises at least one mineral.

Minerals, in accordance with the teachings of this invention, comprise inorganic chemical elements required by living organisms. Minerals are comprised of a broad range of compositions (e.g., elements, simple salts, and complex silicates) and also vary broadly in crystalline structure. They may naturally occur in foods and beverages, may be added as a supplement, or may be consumed or administered separately from foods or beverages.

Minerals may be categorized as either bulk minerals, which are required in relatively large amounts, or trace minerals, which are required in relatively small amounts. Bulk minerals generally are required in amounts greater than or equal to about 100 mg per day and trace minerals are those that are required in amounts less than about 100 mg per day.

In particular embodiments of this invention, the at least one mineral comprises bulk minerals, trace minerals, or combinations thereof. Non-limiting examples of bulk minerals include calcium, chlorine, magnesium, phosphorous, potassium, sodium, and sulfur. Non-limiting examples of trace minerals include chromium, cobalt, copper, fluorine, iron, manganese, molybdenum, selenium, zinc, and iodine. Although iodine generally is classified as a trace mineral, it is required in larger quantities than other trace minerals and often is categorized as a bulk mineral.

In other particular embodiments of this invention, the at least one mineral may comprise other trace minerals that are believed to be necessary for human nutrition, non-limiting examples of which include bismuth, boron, lithium, nickel, rubidium, silicon, strontium, tellurium, tin, titanium, tungsten, and vanadium.

The minerals embodied herein may be in any form known to those of ordinary skill in the art. For example, in a particular embodiment the minerals may be in their ionic form, having either a positive or negative charge. In another particular embodiment the minerals may be in their molecular form. For example, sulfur and phosphorous often are found naturally as sulfates, sulfides, and phosphates.

Appropriate intake of dietary minerals is necessary to maintain health. Sodium, potassium, and chlorine largely regulate the fluid balance in the body. Sodium also is involved in the absorption of other nutrients, such as glucose and amino acids. In addition, sodium and potassium act as cofactors for some enzymes. Other minerals, such as calcium, magnesium, and phosphorous, are essential for the proper development of the skeletal system and serve important structural functions in the body. These minerals also are important for maintaining connective tissue and cell membranes.

Mineral deficiencies contribute to a number of health problems. For example, a sodium or potassium deficiency may cause abnormal nerve activity, cardiac arrhythmias or even cardiac arrest. Deficiencies of iodine, which is used by the body in synthesis of thyroid hormones, may lead to goiter and, in pregnant females, can lead to serious birth defects such as cretinism. Iron is an essential component of hemoglobin, and dietary iron deficiencies can cause anemia, resulting in tiredness and shortness of breath. Calcium deficiencies, which most often are caused by a deficiency in vitamin D, can lead to poor bone structure and osteoporosis. Manganese and zinc deficiencies can result in rashes on the skin of the upper torso, face, groin, hands, and feet.

Although mineral deficiencies can cause serious health problems, excessive mineral intake may also lead to illness. For example, potassium or magnesium toxicity in the body can lead to cardiac arrest. Generally, kidneys that function normally can regulate mineral concentrations within the body and excrete excess amounts of minerals; however, in some cases the body is unable to regulate mineral concentrations properly. This can occur if kidney function is abnormal or if mineral intake is highly excessive. In addition, excess mineral intake of one mineral can influence the absorption and metabolism of other minerals. For example, the presence of a large amount of zinc in the diet decreases the absorption of iron and copper and can lead to harmful deficiencies.

Because of the importance of obtaining an appropriate intake of minerals, people generally should eat a well-balanced diet. However, for many people, available food supply or dietary patterns can cause mineral imbalances or mineral deficiencies, falling short of the Recommended Dietary Allowances (RDAs) promulgated by the Food and Nutrition Board of the National Academy of Sciences. Accordingly, dietary mineral supplements and mineral fortification of foods and beverages are desirable and generally recommended by the Food and Nutrition Board. RDAs for males and females of commonly recognized dietary minerals are provided in the table below along with maximum safe levels of daily nutrient intake; however, this table should not be construed as limiting the scope of the invention. Mineral intake beyond the upper limits provided by the Food and Nutrition Board may be appropriate if prescribed by a physician. Note also that the RDAs in the table below are provided for adult males and adult females. Generally, lower dietary allowances are appropriate for infants and for children under the age of 18.

| Mineral | RDA (adult male, per day) | Upper Limit (adult male, per day) | RDA (adult female, per day) | Upper Limits (adult female, per day) |
|---|---|---|---|---|
| Calcium | 1,000 mg | 2,500 mg | 1,000 mg | 2,500 mg |
| Chloride | 2.3 g | 3.6 g | 2.3 g | 3.6 g |
| Chromium | 35 µg | Not determinable | 25 mg | Not determinable |
| Copper | 900 µg | 10,000 µg | 900 µg | 10,000 µg |
| Iodine | 150 µg | 1,100 µg | 150 µg | 1,100 µg |
| Iron | 8 mg | 45 mg | 18 mg | 45 mg |
| Magnesium | 350 mg* | 350 mg | 310 mg | 350 mg |
| Manganese | 2.3 mg | 11 mg | 1.8 mg | 11 mg |
| Molybdenum | 45 µg | 2,000 µg | 45 µg | 2,000 µg |
| Phosphorus | 700 mg | 4,000 mg | 700 mg | 4,000 mg |
| Potassium | 4.7 g | Not determinable | 4.7 g | Not determinable |
| Selenium | 55 µg | 400 µg | 55 µg | 400 µg |
| Sodium | 1.5 g | 2.3 g | 1.5 g | 2.3 g |
| Zinc | 11 mg | 40 mg | 8 mg | 40 mg |

*Note:
The dietary guidelines of the Food and Nutrition Board recommend 410 mg of magnesium per day for adult males, which is beyond the maximum safe limit promulgated by the Board. The Board's Upper Limit represents intake from a pharmacological agent only and does not include intake from food and water. Intake of magnesium beyond safe upper limits generally is not recommended without first consulting a physician.

According to particular embodiments of this invention, the sweetener compositions provided herein further may comprise at least one functional ingredient different than the minerals described above. According to particular embodiments of this invention, non-limiting examples of such functional ingredients include naturally nutrient-rich or medicinally active food, such as garlic, soybeans, antioxidants, fibers, glucosamine, chondroitin sulfate, ginseng, ginko, Echinacea, or the like; other nutrients that provide health benefits, such as amino acids, vitamins, carotenoids, dietary fiber, fatty acids such as omega-3 or omega-6 fatty acids, DHA, EPA, or ALA which can be derived from plant or animal sources (e.g., salmon and other cold-water fish or algae), flavonoids, phenols, polyols, prebiotics/probiotics, phytosterols and phytostanols and their esters, phytoestrogens, sulfides/thiols, policosanol, saponin, rubisco peptide, appetite suppressants, hydration agents, autoimmune agents, C-reactive protein reducing agents, or anti-inflammatory agents; or any other functional ingredient that is beneficial to the treatment of specific diseases or conditions, such as diabetes, osteoporosis, inflammation, or cholesterol.

II. Natural and/or Synthetic High-Potency Sweeteners

The sweetener compositions provided also comprise at least one natural and/or synthetic high-potency sweetener. As used herein the phrases "natural high-potency sweetener", "NHPS", "NHPS composition", and "natural high-potency sweetener composition" are synonymous. "NHPS" means any sweetener found in nature which may be in raw, extracted, purified, or any other form, singularly or in combination thereof and characteristically have a sweetness potency greater than sucrose, fructose, or glucose, yet have less calories. Non-limiting examples of NHPSs suitable for embodiments of this invention include rebaudioside A, rebaudioside B, rebaudioside C, rebaudioside D, rebaudioside E, rebaudioside F, dulcoside A, dulcoside B, rubusoside, stevia, stevioside, mogroside IV, mogroside V, Luo Han Guo sweetener, siamenoside, monatin and its salts (monatin SS, RR, RS, SR), curculin, glycyrrhizic acid and its salts, thaumatin, monellin, mabinlin, brazzein, hernandulcin, phyllodulcin, glycyphyllin, phloridzin, trilobatin, baiyunoside, osladin, polypodoside A, pterocaryoside A, pterocaryoside B, mukurozioside, phlomisoside I, periandrin I, abrusoside A, and cyclocarioside I.

NHPS also includes modified NHPSs. Modified NlPSs include NHPSs which have been altered naturally. For example, a modified NHPS includes, but is not limited to, NHPSs which have been fermented, contacted with enzyme, or derivatized or substituted on the NHPS. In one embodiment, at least one modified NHPS may be used in combination with at least one NHPS. In another embodiment, at least one modified NHPS may be used without a NHPS. Thus, modified NHPSs may be substituted for a NHPS or may be used in combination with NHPSs for any of the embodiments described herein. For the sake of brevity, however, in the description of embodiments of this invention, a modified NHPS is not expressly described as an alternative to an unmodified NHPS, but it should be understood that modified NHPSs can be substituted for NHPSs in any embodiment disclosed herein.

In one embodiment, extracts of a NHPS may be used in any purity percentage. In another embodiment, when a NHPS is used as a non-extract, the purity of the NHPS may range for example from about 25% to about 100%. According to other embodiments, the purity of the NHPS may range from about 50% to about 100%; from about 70% to about 100%; from about 80% to about 100%; from about 90% to about 100%; from about 95% to about 100%; from about 95% to about 99.5%; from about 96% to about 100%; from about 97% to about 100%; from about 98% to about 100%; and from about 99% to about 100%.

Purity, as used here, represents the weight percentage of a respective NHPS compound present in a NHPS extract, in raw or purified form. In one embodiment, a steviolglycoside extract comprises a particular steviolglycoside in a particular purity, with the remainder of the stevioglycoside extract comprising a mixture of other steviolglycosides.

To obtain a particularly pure extract of a NHPS, such as rebaudioside A, it may be necessary to purify the crude extract to a substantially pure form. Such methods generally are known to those of ordinary skill in the art.

An exemplary method for purifying a NHPS, such as rebaudioside A, is described in the co-pending patent application no. 60/805,216, entitled "Rebaudioside A Composition and Method for Purifying Rebaudioside A," filed on Jun. 19, 2006, by inventors DuBois, et al., the disclosure of which is incorporated herein by reference in its entirety.

Briefly described, substantially pure rebaudioside A is crystallized in a single step from an aqueous organic solution comprising at least one organic solvent and water in an amount from about 10% to about 25% by weight, more particularly from about 15% to about 20% by weight. Organic solvents desirably comprise alcohols, acetone, and acetonitrile. Non-limiting examples of alcohols include ethanol, methanol, isopranol, 1-propanol, 1-butanol, 2-butanol, tert-butanol, and isobutanol. Desirably, the at least one organic solvent comprises a mixture of ethanol and methanol present in the aqueous organic solution in a weight ratio ranging from about 20 parts to about 1 part ethanol to 1 part methanol, more desirably from about 3 parts to about 1 part ethanol to 1 part methanol.

Desirably, the weight ratio of the aqueous organic solvent and crude rebaudioside A ranges from about 10 to about 4 parts aqueous organic solvent to 1 part crude rebaudioside A, more particularly from about 5 to about 3 parts aqueous organic solvent to 1 part crude rebaudioside A.

In an exemplary embodiment, the method of purifying rebaudioside A is carried out at approximately room temperature. In another embodiment, the method of purifying rebaudioside A further comprises the step of heating the rebaudioside A solution to a temperature in a range from about 20° C. to about 40° C., or in another embodiment to a reflux temperature, for about 0.25 hours to about 8 hours. In another exemplary embodiment, wherein the method for purifying rebaudioside A comprises the step of heating the rebaudioside A solution, the method further comprises the step of cooling the rebaudioside A solution to a temperature in the range from about 4° C. to about 25° C. for about 0.5 hours to about 24 hours.

According to particular embodiments, the purity of rebaudioside A may range from about 50% to about 100%; from about 70% to about 100%; from about 80% to about 100%; from about 90% to about 100%; from about 95% to about 100%; from about 95% to about 99.5%; about 96% to about 100%; from about 97% to about 100%; from about 98% to about 100%; and from about 99% to about 100%. According to particularly desirable embodiments, upon crystallization of crude rebaudioside A, the substantially pure rebaudioside A composition comprises rebaudioside A in a purity greater than about 95% by weight up to about 100% by weight on a dry basis. In other exemplary embodiments, substantially pure rebaudioside A comprises purity levels of rebaudioside A greater than about 97% up to about 100% rebaudioside A by weight on a dry basis, greater than about 98% up to about 100% by weight on a dry basis, or greater than about 99% up to about 100% by weight on a dry basis. The rebaudioside A solution during the single crystallization step may be stirred or unstirred.

In an exemplary embodiment, the method of purifying rebaudioside A further comprises the step of seeding (optional step) the rebaudioside A solution at an appropriate temperature with high-purity crystals of rebaudioside A sufficient to promote crystallization of the rebaudioside A to form pure rebaudioside A. An amount of rebaudioside A sufficient to promote crystallization of substantially pure rebaudioside A comprises an amount of rebaudioside A from about 0.0001% to about 1% by weight of the rebaudioside A present in the solution, more particularly from about 0.01% to about 1% by weight. An appropriate temperature for the step of seeding comprises a temperature in a range from about 18° C. to about 35° C.

In another exemplary embodiment, the method of purifying rebaudioside A further comprises the steps of separating and washing the substantially pure rebaudioside A composition. The substantially pure rebaudioside A composition may be separated from the aqueous organic solution by a variety of solid-liquid separation techniques that utilize centrifugal force, that include, without limitation, vertical and horizontal perforated basket centrifuge, solid bowl centrifuge, decanter centrifuge, peeler type centrifuge, pusher type centrifuge, Heinkel type centrifuge, disc stack centrifuge and cyclone separation. Additionally, separation may be enhanced by any of pressure, vacuum, and gravity filtration methods, that include, without limitation, the use of belt, drum, nutsche type, leaf, plate, Rosenmund type, sparkler type, and bag filters and filter press. Operation of the rebaudioside A solid-liquid separation device may be continuous, semi-continuous or in batch mode. The substantially pure rebaudioside A composition also may be washed on the separation device using various aqueous organic solvents and mixtures thereof. The substantially pure rebaudioside A composition can be dried partially or totally on the separation device using any number of gases, including, without limitation, nitrogen and argon, to evaporate residual liquid solvent. The substantially pure rebaudioside A composition may be removed automatically or manually from the separation device using liquids, gases or mechanical means by either dissolving the solid or maintaining the solid form.

In still another exemplary embodiment, the method of purifying rebaudioside A further comprises the step of drying the substantially pure rebaudioside A composition using techniques well known to those skilled in the art, non-limiting examples of which include the use of a rotary vacuum dryer, fluid bed dryer, rotary tunnel dryer, plate dryer, tray dryer, Nauta type dryer, spray dryer, flash dryer, micron dryer, pan dryer, high and low speed paddle dryer and microwave dryer. In an exemplary embodiment, the step of drying comprises drying the substantially pure rebaudioside A composition using a nitrogen or argon purge to remove the residual solvent at a temperature in a range from about 40° C. to about 60° C. for about 5 hours to about 100 hours.

In yet another exemplary embodiment, wherein the crude rebaudioside A mixture comprises substantially no rebaudioside D impurity, the method of purifying rebaudioside A further comprises the step of slurrying the composition of substantially pure rebaudioside A with an aqueous organic solvent prior to the step of drying the substantially pure rebaudioside A composition. The slurry is a mixture comprising a solid and an aqueous organic or organic solvent, wherein the solid comprises the substantially pure rebaudioside A composition and is only sparingly soluble in the aqueous organic or organic solvent. In an embodiment, the substantially pure rebaudioside A composition and aqueous organic solvent are present in the slurry in a weight ratio ranging from about 15 parts to 1 part aqueous organic solvent to 1 part substantially pure rebaudioside A composition. In one embodiment, the slurry is maintained at room temperature. In another embodiment, the step of slurrying comprises heating the slurry to a temperature in a range from about 20 to about 40° C. The substantially pure rebaudioside A composition is slurried for about 0.5 hours to about 24 hours.

In still yet another exemplary embodiment, the method of purifying rebaudioside A further comprises the steps of separating the substantially pure rebaudioside A composition from the aqueous organic or organic solvent of the slurry and washing the substantially pure rebaudioside A composition followed by the step of drying the substantially pure rebaudioside A composition.

If further purification is desired, the method of purifying rebaudioside A described herein may be repeated or the substantially pure rebaudioside A composition may be purified further using an alternative purification method, such as the column chromatography.

It also is contemplated that other NHPSs may be purified using the purification method described herein, requiring only minor experimentation that would be obvious to those of ordinary skill in the art.

Figure 2:
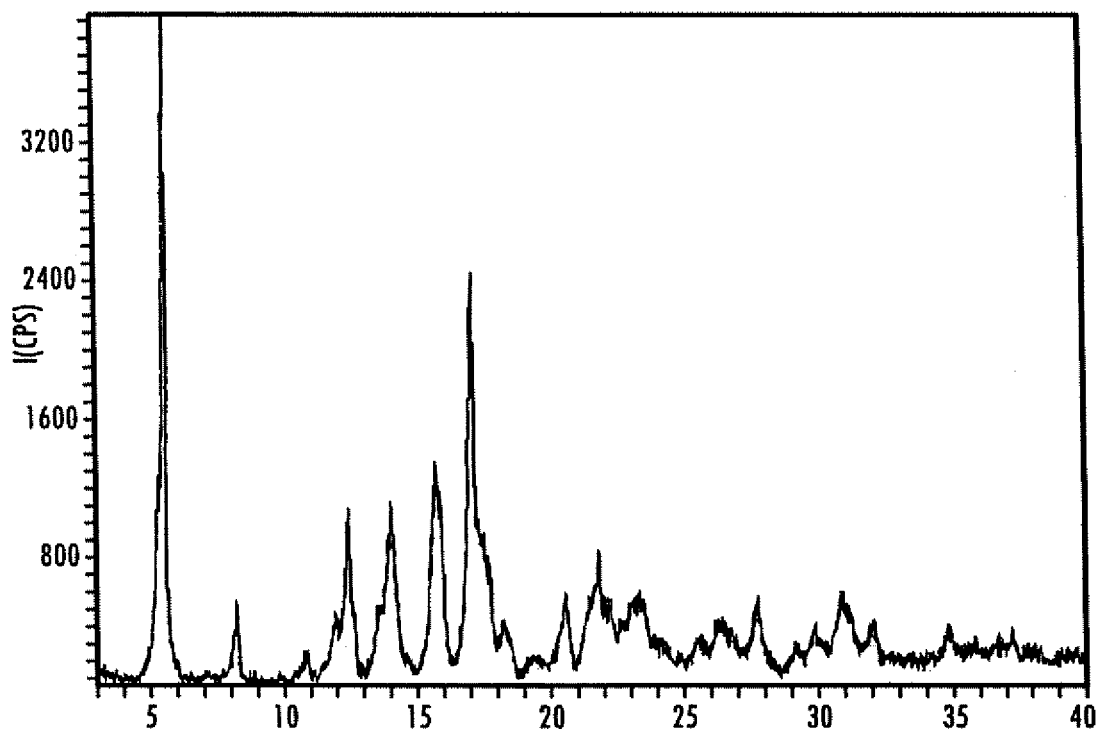
FIG. 2 is a powder x-ray diffraction scan of rebaudioside A polymorph Form 2 on a plot of the scattering intensity versus the scattering angle 2θ in accordance with an embodiment of this invention.
Figure 3:
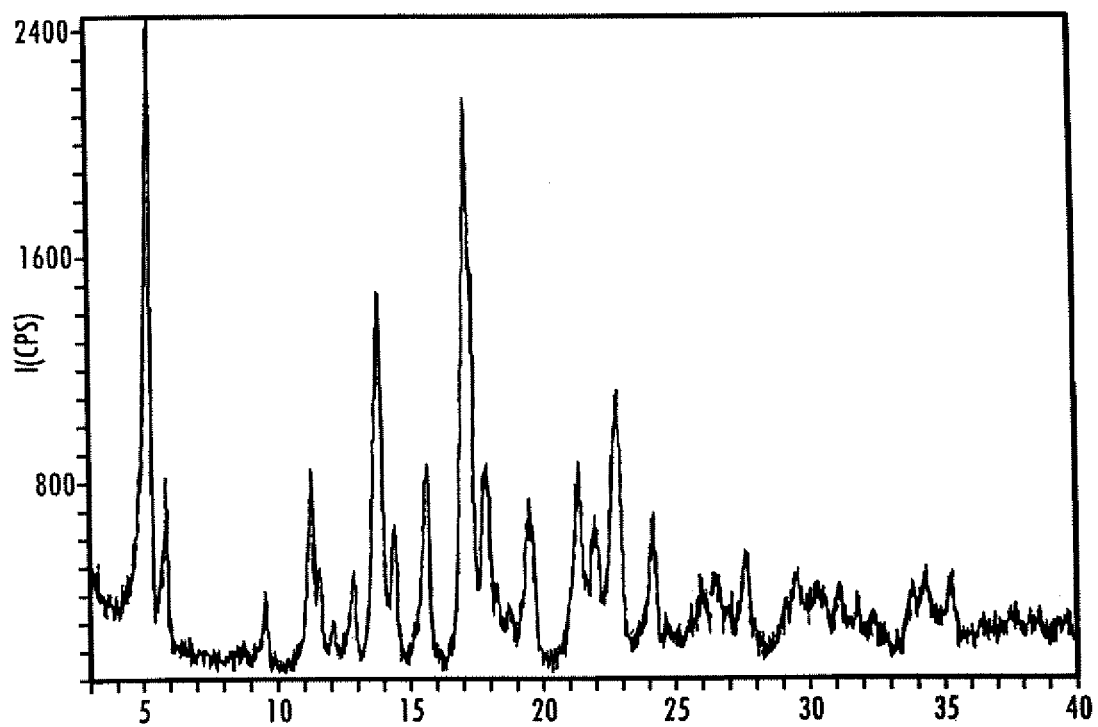
FIG. 3 is a powder x-ray diffraction scan of rebaudioside A polymorph Form 3A on a plot of the scattering intensity versus the scattering angle 2θ in accordance with an embodiment of this invention.
Figure 4:
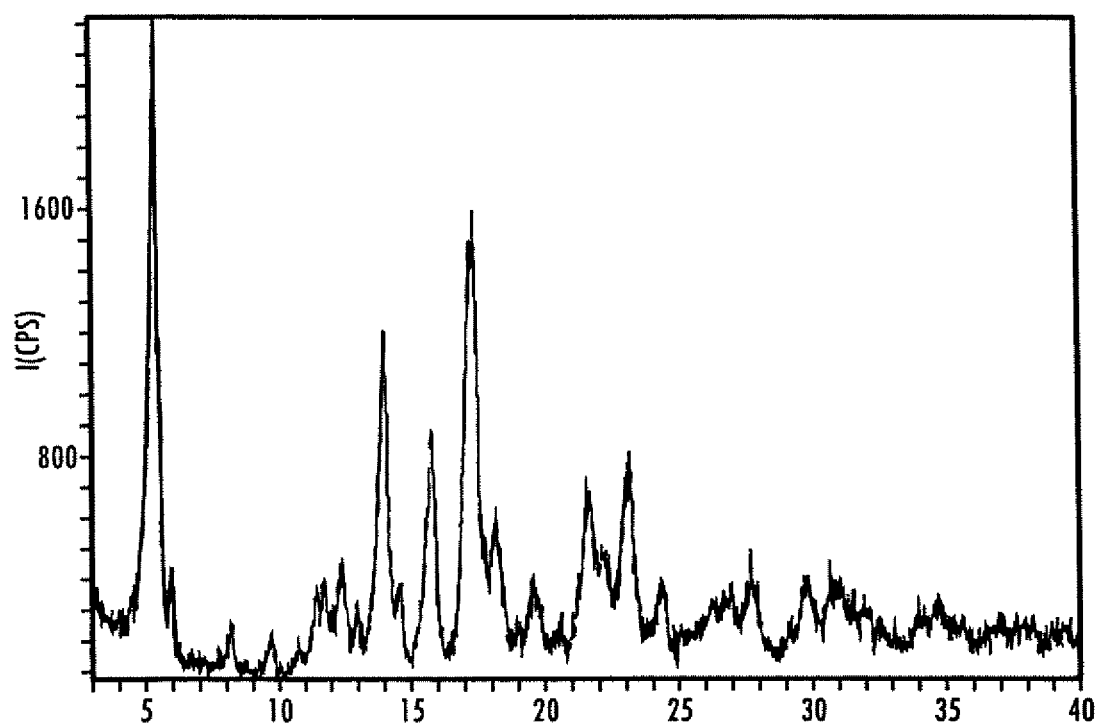
FIG. 4 is a powder x-ray diffraction scan of rebaudioside A polymorph Form 3B on a plot of the scattering intensity versus the scattering angle 2θ in accordance with an embodiment of this invention.
Figure 5:
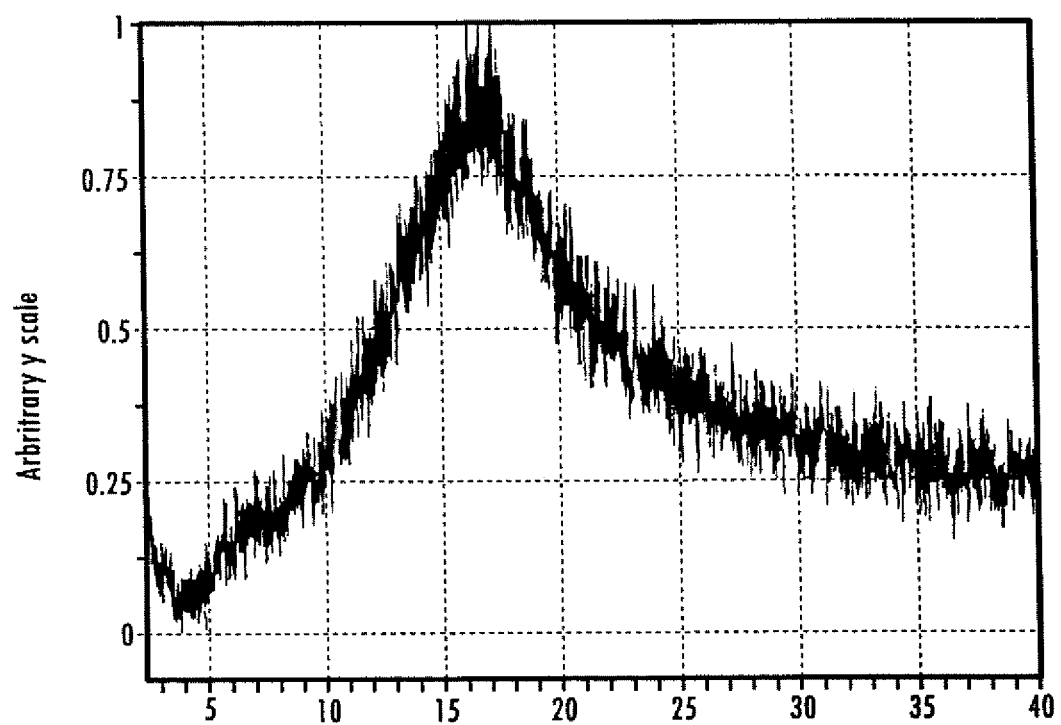
FIG. 5 is a powder x-ray diffraction scan of rebaudioside A polymorph Form 4 on a plot of the scattering intensity versus the scattering angle 2θ in accordance with an embodiment of this invention.

The purification of rebaudioside A by crystallization as described above results in the formation of at least three different polymorphs: Form 1: a rebaudioside A hydrate; Form 2: an anhydrous rebaudioside A; and Form 3: a rebaudioside A solvate. In addition to the at least three polymorph forms of rebaudioside A, the purification of rebaudioside A may result in the formation of an amorphous form of rebaudioside A, Form 4. The aqueous organic solution and temperature of the purification process influence the resulting polymorph and amorphous forms in the substantially pure rebaudioside A composition. FIGS. 1-5 are exemplary powder x-ray diffraction (XRPD) scans of the polymorph and amorphous forms of rebaudioside A: Form 1 (hydrate), Form 2 (anhydrate), Form 3A (methanol solvate), Form 3B (ethanol solvate), and Form 4 (amorphous), respectively.

The material properties of the three rebaudioside A polymorph and amorphous forms are summarized in the following table;

TABLE 1

| Rebaudioside A Polymorph and Amorphous Forms | | | | |
|---|---|---|---|---|
| | Form 1 Polymorph | Form 2 Polymorph | Form 3 Polymorph | Form 4 Amorphous |
| Rate of dissolution in H2O at 25° C. | Very low (<0.2%/ 60 minutes) | Intermediate (<30%/ 5 minutes) | High (>30%/5 minutes) | High (>35%/5 minutes) |
| Alcohol content | <0.5% | <1% | 1-3% | <0.05% |
| Moisture content | >5% | <1% | <3% | 6.74% |

The type of polymorph formed is dependent on the composition of the aqueous organic solution, the temperature of the crystallization step, and the temperature during the drying step. Form 1 and Form 3 are formed during the single crystallization step while Form 2 is formed during the drying step after conversion from Form 1 or Form 3.

Low temperatures during the crystallization step, in the range of about 20° C. to about 50° C., and a low ratio of water to the organic solvent in the aqueous organic solvent results in the formation of Form 3. High temperatures during the crystallization step, in the range of about 50° C. to about 80° C., and a high ratio of water to the organic solvent in the aqueous organic solvent results in the formation of the Form 1. Form 1 can be converted to Form 3 by slurrying in an anhydrous solvent at room temperature (2-16 hours) or at reflux for approximately (0.5-3 hours). Form 3 can be converted to Form 1 by slurrying the polymorph in water at room temperature for approximately 16 hours or at reflux for approximately 2-3 hours. Form 3 can be converted to the Form 2 during the drying process; however, increasing either the drying temperature above 70° C. or the drying time of a substantially pure rebaudioside A composition can result in decomposition of the rebaudioside A and increase the remaining rebaudioside B impurity in the substantially pure rebaudioside A composition. Form 2 can be converted to Form 1 with the addition of water.

Form 4 may be formed from Form 1, 2, 3, or combinations thereof, using methods well known to those of ordinary skill in the art. Non-limiting examples of such methods include melt-processing, ball milling, crystallization, lyophilization, cryo-grinding, and spray-drying. In a particular embodiment, Form 4 can be prepared from a substantially pure rebaudioside A composition obtained by the purification methods described hereinabove by spray-drying a solution of the substantially pure rebaudioside A composition.

As used herein, the phrase "synthetic sweetener" refers to any compositions which are not found in nature and characteristically have a sweetness potency greater than sucrose, fructose, or glucose, yet have less calories. Non-limiting examples of synthetic sweeteners suitable for embodiments of this invention include sucralose, potassium acesulfame, aspartame, alitame, saccharin, neohesperidin dihydrochalcone, cyclamate, neotame, N—[N-[3-(3-hydroxy-4-methoxyphenyl)propyl]-L-α-aspartyl]-L-phenylalanine 1-methyl ester, N—[N-[3-(3-hydroxy-4-methoxyphenyl)-3-methylbutyl]-L-α-aspartyl]-L-phenylalanine 1-methyl ester, N—[N-[3-(3-methoxy-4-hydroxyphenyl)propyl]-L-α-aspartyl]-L-phenylalanine 1-methyl ester, salts thereof, and the like.

The NHPS and synthetic sweeteners may be used individually or in combination with other NHPS and/or synthetic sweeteners. For example, the sweetener composition may comprise a single NHPS or a single synthetic sweetener; a single NHPS in combination with a single synthetic sweetener; one or more NHPSs in combination with a single synthetic sweetener; a single NHPS in combination with one or more synthetic sweeteners; or one or more NHPSs in combination with one or more synthetic sweeteners. A plurality of natural and/or synthetic high-potency sweeteners may be used as long as the combined effect does not adversely affect the taste of the sweetener composition or orally sweetened composition.

For example, particular embodiments comprise combinations of NHPSs, such as steviolglycosides. Non-limiting examples of suitable stevioglycosides which may be combined include rebaudioside A, rebaudioside B, rebaudioside C, rebaudioside D, rebaudioside E, rebaudioside F, dulcoside A, dulcoside B, rubusoside, stevioside, or steviolbioside. According to particularly desirable embodiments of the present invention, the combination of high-potency sweeteners comprises rebaudioside A in combination with rebaudioside B, rebaudioside C, rebaudioside E, rebaudioside F, stevioside, steviolbioside, dulcoside A, or combinations thereof.

Generally, according to a particular embodiment, rebaudioside A is present in the combination of high-potency sweeteners in an amount in the range of about 50 to about 99.5 weight percent of the combination of high-potency sweeteners, more desirably in the range of about 70 to about 90 weight percent, and still more desirably in the range of about 75 to about 85 weight percent.

In another particular embodiment, rebaudioside B is present in the combination of high-potency sweeteners in an amount in the range of about 1 to about 8 weight percent of the combination of high-potency sweeteners, more desirably in the range of about 2 to about 5 weight percent, and still more desirably in the range of about 2 to about 3 weight percent.

In another particular embodiment, rebaudioside C is present in the combination of high-potency sweeteners in an amount in the range of about 1 to about 10 weight percent of the combination of high-potency sweeteners, more desirably in the range of about 3 to about 8 weight percent, and still more desirably in the range of about 4 to about 6 weight percent.

In still another particular embodiment, rebaudioside E is present in the combination of high-potency sweeteners in an amount in the range of about 0.1 to about 4 weight percent of the combination of high-potency sweeteners, more desirably in the range of about 0.1 to about 2 weight percent, and still more desirably in the range of about 0.5 to about 1 weight percent.

In still another particular embodiment, rebaudioside F is present in the combination of high-potency sweeteners in an amount in the range of about 0.1 to about 4 weight percent of the combination of high-potency sweeteners, more desirably in the range of about 0.1 to about 2 weight percent, and still more desirably in the range of about 0.5 to about 1 weight percent.

In still yet another particular embodiment, dulcoside A is present in the combination of high-potency sweeteners in an amount in the range of about 0.1 to about 4 weight percent of the combination of high-potency sweeteners, more desirably in the range of about 0.1 to about 2 weight percent, and still more desirably in the range of about 0.5 to about 1 weight percent.

In yet another particular embodiment, dulcoside B is present in the combination of high-potency sweeteners in an amount in the range of about 0.1 to about 4 weight percent of the combination of high-potency sweeteners, more desirably in the range of about 0.1 to about 2 weight percent, and still more desirably in the range of about 0.5 to about 1 weight percent.

In another particular embodiment, stevioside is present in the combination of high-potency sweeteners in an amount in the range of about 0.5 to about 10 weight percent of the combination of high-potency sweeteners, more desirably in the range of about 1 to about 6 weight percent, and still more desirably in the range of about 1 to about 4 weight percent.

In still another particular embodiment, steviolbioside is present in the combination of high-potency sweeteners in an amount in the range of about 0.1 to about 4 weight percent of the combination of high-potency sweeteners, more desirably in the range of about 0.1 to about 2 weight percent, and still more desirably in the range of about 0.5 to about 1 weight percent.

According to a particularly desirable embodiment, the high-potency sweetener composition comprises a combination of rebaudioside A, stevioside, rebaudioside B, rebaudioside C, and rebaudioside F; wherein rebaudioside A is present in the combination of high-potency sweeteners in an amount in the range of about 75 to about 85 weight percent based on the total weight of the combination of high-potency sweeteners, stevioside is present in an amount in the range of about 1 to about 6 weight percent, rebaudioside B is present in an amount in the range of about 2 to about 5 weight percent, rebaudioside C is present in an amount in the range of about 3 to about 8 weight percent, and rebaudioside F is present in an amount in the range of about 0.1 to about 2 weight percent.

In addition, those of ordinary skill in the art should appreciate that the sweetener composition can be customized to obtain a desired calorie content. For example, a low-caloric or non-caloric NHPS may be combined with a caloric natural sweetener and/or other caloric additives to produce a sweetener composition with a preferred calorie content.

III. Sweet Taste Improving Compositions

The sweetener composition also comprises a sweet taste improving composition, non-limiting examples of which include carbohydrates, polyols, amino acids and their corresponding salts, polyamino acids and their corresponding salts, sugar acids and their corresponding salts, nucleotides, organic acids, inorganic acids, organic salts including organic acid salts and organic base salts, inorganic salts, bitter compounds, flavorants and flavoring ingredients, astringent compounds, proteins or protein hydrolysates, surfactants, emulsifiers, flavonoids, alcohols, polymers, other sweet taste improving taste additives imparting such sugar-like characteristics, and combinations thereof.

In one embodiment, a single sweet taste improving composition may be used in combination with a single natural and/or synthetic high-potency sweetener. In another embodiment of the present invention, a single sweet taste improving composition may be used in combination with one or more natural and/or synthetic high-potency sweeteners. In yet another embodiment, one or more sweet taste improving compositions may be used in combination with a single natural and/or synthetic high-potency sweetener. In a further embodiment, there may be a plurality of sweet taste improving combinations used in combination with one or more natural and/or synthetic high-potency sweeteners.

In a particular embodiment, combinations of at least one natural and/or synthetic high-potency sweetener and at least one sweet taste improving composition suppress, reduce, or eliminate undesirable taste and impart sugar-like characteristics to the sweetener. As used herein, the phrase "undesirable taste" includes any taste property which is not imparted by sugars, e.g. glucose, sucrose, fructose, or similar saccharides. Non-limiting examples of undesirable tastes include delayed sweetness onset, lingering sweet aftertaste, metallic taste, bitter taste, cooling sensation taste or menthol-like taste, licorice-like taste, and/or the like.

In one embodiment, a sweetener composition exhibits a more sugar-like temporal and/or sugar-like flavor profile than a sweetener composition comprising at least one natural and/or synthetic high-potency sweetener, but without a sweet taste improving composition is provided. As used herein, the phrases "sugar-like characteristic," "sugar-like taste," "sugar-like sweet," "sugary," and "sugar-like" are synonymous. Sugar-like characteristics include any characteristic similar to that of sucrose and include, but are not limited to, maximal response, flavor profile, temporal profile, adaptation behavior, mouthfeel, concentration/response function behavior, tastant and flavor/sweet taste interactions, spatial pattern selectivity, and temperature effects. These characteristics are dimensions in which the taste of sucrose is different from the tastes of natural and synthetic high-potency sweeteners. Whether or not a characteristic is more sugar-like is determined by expert sensory panel assessments of sugar and compositions comprising at least one natural and/or synthetic high-potency sweetener, both with and without a sweet taste improving composition. Such assessments quantify similarities of the characteristics of compositions comprising at least one natural and/or synthetic high-potency sweetener, both with and without a sweet taste improving composition, with those comprising sugar. Suitable procedures for determining whether a composition has a more sugar-like taste are well know in the art.

In a particular embodiment, a panel of assessors is used to measure the reduction of sweetness linger. Briefly described, a panel of assessors (generally 8 to 12 individuals) is trained to evaluate sweetness perception and measure sweetness at several time points from when the sample is initially taken into the mouth until 3 minutes after it has been expectorated. Using statistical analysis, the results are compared between samples containing additives and samples that do not contain additives. A decrease in score for a time point measured after the sample has cleared the mouth indicates there has been a reduction in sweetness perception.

The panel of assessors may be trained using procedures well known to those of ordinary skill in the art. In a particular embodiment, the panel of assessors may be trained using the Spectrum™ Descriptive Analysis Method (Meilgaard et al, *Sensory Evaluation Techniques*, 3$^{rd}$ edition, Chapter 11). Desirably, the focus of training should be the recognition of and the measure of the basic tastes; specifically, sweet. In order to ensure accuracy and reproducibility of results, each assessor should repeat the measure of the reduction of sweetness linger about three to about five times per sample, taking at least a five minute break between each repetition and/or sample and rinsing well with water to clear the mouth.

Generally, the method of measuring sweetness comprises taking a 10 mL sample into the mouth, holding the sample in the mouth for 5 seconds and gently swirling the sample in the mouth, rating the sweetness intensity perceived at 5 seconds, expectorating the sample (without swallowing following expectorating the sample), rinsing with one mouthful of water (e.g., vigorously moving water in mouth as if with mouth wash) and expectorating the rinse water, rating the sweetness intensity perceived immediately upon expectorating the rinse water, waiting 45 seconds and, while wating those 45 seconds, identifying the time of maximum perceived sweetness intensity and rating the sweetness intensity at that time (moving the mouth normally and swallowing as needed), rating the sweetness intensity after another 10 seconds, rating the sweetness intensity after another 60 seconds (cumulative 120 seconds after rinse), and rating the sweetness intensity after still another 60 seconds (cumulative 180 seconds after rinse). Between samples take a 5 minute break, rinsing well with water to clear the mouth.

As used herein, the term "carbohydrate" generally refers to aldehyde or ketone compounds substituted with multiple hydroxyl groups, of the general formula $(CH_2O)_n$, wherein n is 3-30, as well as their oligomers and polymers. The carbohydrates of the present invention can, in addition, be substituted or deoxygenated at one or more positions. Carbohydrates, as used herein, encompass unmodified carbohydrates, carbohydrate derivatives, substituted carbohydrates, and modified carbohydrates. As used herein, the phrases "carbohydrate derivatives", "substituted carbohydrate", and "modified carbohydrates" are synonymous. Modified carbohydrate means any carbohydrate wherein at least one atom has been added, removed, substituted, or combinations thereof. Thus, carbohydrate derivatives or substituted carbohydrates include substituted and unsubstituted monosaccharides, disaccharides, oligosaccharides, and polysaccharides. The carbohydrate derivatives or substituted carbohydrates optionally can be deoxygenated at any corresponding C-position, and/or substituted with one or more moieties such as hydrogen, halogen, haloalkyl, carboxyl, acyl, acyloxy, amino, amido, carboxyl derivatives, alkylamino, dialkylamino, arylamino, alkoxy, aryloxy, nitro, cyano, sulfo, mercapto, imino, sulfonyl, sulfenyl, sulfinyl, sulfamoyl, carboalkoxy, carboxamido, phosphonyl, phosphinyl, phosphoryl, phosphino, thioester, thioether, oximino, hydrazino, carbamyl, phospho, phosphonato, or any other viable functional group provided the carbohydrate derivative or substituted carbohydrate functions to improve the sweet taste of at least one natural and/or synthetic high-potency sweetener.

Non-limiting examples of carbohydrates in embodiments of this invention include tagatose, trehalose, galactose, rhamnose, cyclodextrin (e.g., α-cyclodextrin, β-cyclodextrin, and γ-cyclodextrin), maltodextrin (including resistant maltodextrins such as Fibersol-2™), dextran, sucrose, glucose, ribulose, fructose, threose, arabinose, xylose, tyxose, allose, altrose, mannose, idose, lactose, maltose, invert sugar, isotrehalose, neotrehalose, palatinose or isomaltulose, erythrose, deoxyribose, gulose, idose, talose, erythrulose, xylulose, psicose, turanose, cellobiose, amylopectin, glucosamine, mannosamine, fucose, glucuronic acid, gluconic acid, gluconolactone, abequose, galactosamine, beet oligosaccharides, isomalto-oligosaccharides (isomaltose, isomaltotriose, panose and the like), xylo-oligosaccharides (xylotriose, xylobiose and the like), gentio-oligoscaccharides (gentiobiose, gentiotriose, gentiotetraose and the like), sorbose, nigero-oligosaccharides, palatinose oligosaccharides, fructooligosaccharides (kestose, nystose and the like), maltotetraol, maltotriol, malto-oligosaccharides (maltotriose, maltotetraose, maltopentaose, maltohexaose, maltoheptaose and the like), lactulose, melibiose, raffinose, rhamnose, ribose, isomerized liquid sugars such as high fructose corn/starch syrup (e.g., HFCS55, HFCS42, or HFCS90), coupling sugars, soybean oligosaccharides, and glucose syrup. Additionally, the carbohydrates as used herein may be in either the D- or L-configuration.

The term "polyol", as used herein, refers to a molecule that contains more than one hydroxyl group. A polyol may be a diol, triol, or a tetraol which contain 2, 3, and 4 hydroxyl groups, respectively. A polyol also may contain more than four hydroxyl groups, such as a pentaol, hexaol, heptaol, or the like, which contain, 5, 6, or 7 hydroxyl groups, respectively. Additionally, a polyol also may be a sugar alcohol, polyhydric alcohol, or polyalcohol which is a reduced form of carbohydrate, wherein the carbonyl group (aldehyde or ketone, reducing sugar) has been reduced to a primary or secondary hydroxyl group.

Non-limiting examples of sweet taste improving polyol additives in embodiments of this invention include erythritol, maltitol, mannitol, sorbitol, lactitol, xylitol, inositol, isomalt, propylene glycol, glycerol (glycerine), threitol, galactitol, palatinose, reduced isomalto-oligosaccharides, reduced xylo-oligosaccharides, reduced gentio-oligosaccharides, reduced maltose syrup, reduced glucose syrup, and sugar alcohols or any other carbohydrates capable of being reduced which do not adversely affect the taste of the at least one natural and/or synthetic high-potency sweetener or the orally ingestible composition.

Suitable sweet taste improving amino acid additives for use in embodiments of this invention include, but are not limited to, aspartic acid, arginine, glycine, glutamic acid, proline, threonine, theanine, cysteine, cystine, alanine, valine, tyrosine, leucine, isoleucine, asparagine, serine, lysine, histidine, ornithine, methionine, carnitine, aminobutyric acid (alpha-, beta-, or gamma-isomers), glutamine, hydroxyproline, taurine, norvaline, sarcosine, and their salt forms such as sodium or potassium salts or acid salts. The sweet taste improving amino acid additives also may be in the D- or L-configuration and in the mono-, di-, or tri-form of the same or different amino acids. Additionally, the amino acids may be α-, β-, γ-, δ-, and ε-isomers if appropriate. Combinations of the foregoing amino acids and their corresponding salts (e.g., sodium, potassium, calcium, magnesium salts or other alkali or alkaline earth metal salts thereof, or acid salts) also are suitable sweet taste improving additives in embodiments of this invention. The amino acids may be natural or synthetic. The amino acids also may be modified. Modified amino acids refers to any amino acid wherein at least one atom has been added, removed, substituted, or combinations thereof (e.g., N-alkyl amino acid, N-acyl amino acid, or N-methyl amino acid). Non-limiting examples of modified amino acids include amino acid derivatives such as trimethyl glycine, N-methyl-glycine, and N-methyl-alanine. As used herein, amino acids encompass both modified and unmodified amino acids. As used herein, modified amino acid also may encompass peptides and polypeptides (e.g., dipeptides, tripeptides, tetrapeptides, and pentapeptides) such as glutathione and L-alanyl-L-glutamine.

Suitable sweet taste improving polyamino acid additives include poly-L-aspartic acid, poly-L-lysine (e.g., poly-L-α-lysine or poly-L-ε-lysine), poly-L-ornithine (e.g., poly-L-α-ornithine or poly-L-ε-ornithine), poly-L-arginine, other polymeric forms of amino acids, and salt forms thereof (e.g., magnesium, calcium, potassium, or sodium salts such as L-glutamic acid mono sodium salt). The sweet taste improving polyamino acid additives also may be in the D- or L-configuration. Additionally, the polyamino acids may be α-, β-, γ-, δ-, and ε-isomers if appropriate. Combinations of the foregoing polyamino acids and their corresponding salts (e.g., sodium, potassium, calcium, magnesium salts or other alkali or alkaline earth metal salts thereof or acid salts) also are suitable sweet taste improving additives in embodiments of this invention. The polyamino acids described herein also may comprise co-polymers of different amino acids. The polyamino acids may be natural or synthetic. The polyamino acids also may be modified, such that at least one atom has been added, removed, substituted, or combinations thereof (e.g., N-alkyl polyamino acid or N-acyl polyamino acid). As used herein, polyamino acids encompass both modified and unmodified polyamino acids. In accordance with particular embodiments, modified polyamino acids include, but are not limited to polyamino acids of various molecular weights (MW), such as poly-L-α-lysine with a MW of 1,500, MW of 6,000, MW of 25,200, MW of 63,000, MW of 83,000, or MW of 300,000.

Suitable sweet taste improving sugar acid additives for use in embodiments of this invention include, but are not limited to, aldonic, uronic, aldaric, alginic, gluconic, glucuronic, glucaric, galactaric, galacturonic, and their salts (e.g., sodium, potassium, calcium, magnesium salts or other physiologically acceptable salts), and combinations thereof.

Suitable sweet taste improving nucleotide additives for use in embodiments of this invention include, but are not limited to, inosine monophosphate ("IMP"), guanosine monophosphate ("GMP"), adenosine monophosphate ("AMP"), cytosine monophosphate (CMP), uracil monophosphate (UMP), inosine diphosphate, guanosine diphosphate, adenosine diphosphate, cytosine diphosphate, uracil diphosphate, inosine triphosphate, guanosine triphosphate, adenosine triphosphate, cytosine triphosphate, uracil triphosphate, and their alkali or alkaline earth metal salts, and combinations thereof. The nucleotides described herein also may comprise nucleotide-related additives, such as nucleosides or nucleic acid bases (e.g., guanine, cytosine, adenine, thymine, uracil).

Suitable sweet taste improving organic acid additives include any compound which comprises a —COOH moiety. Suitable sweet taste improving organic acid additives for use in embodiments of this invention include, but are not limited to, C2-CS30 carboxylic acids, substituted hydroxyl C1-C30 carboxylic acids, benzoic acid, substituted benzoic acids (e.g. 2,4-dihydroxybenzoic acid), substituted cinnamic acids, hydroxyacids, substituted hydroxybenzoic acids, substituted cyclohexyl carboxylic acids, tannic acid, lactic acid, tartaric acid, citric acid, gluconic acid, glucoheptonic acids, adipic acid, hydroxycitric acid, malic acid, fruitaric acid (a blend of malic, fumaric, and tartaric acids), fumaric acid, maleic acid, succinic acid, chlorogenic acid, salicylic acid, creatine, glucosamine hydrochloride, glucono delta lactone, caffeic acid, bile acids, acetic acid, ascorbic acid, alginic acid, erythorbic acid, polyglutamic acid, and their alkali or alkaline earth metal salt derivatives thereof. In addition, the sweet taste improving organic acid additives also may be in either the D- or L-configuration.

Suitable sweet taste improving organic acid salt additives include, but are not limited to, sodium, calcium, potassium, and magnesium salts of all organic acids, such as salts of citric acid, malic acid, tartaric acid, fumaric acid, lactic acid (e.g., sodium lactate), alginic acid (e.g., sodium alginate), ascorbic acid (e.g., sodium ascorbate), benzoic acid (e.g., sodium benzoate or potassium benzoate), and adipic acid. The examples of the sweet taste improving organic acid salt additives described optionally may be substituted with one or more of the following moiety selected from the group consisting of hydrogen, alkyl, alkenyl, alkynyl, halo, haloalkyl, carboxyl, acyl, acyloxy, amino, amido, carboxyl derivatives, alkylamino, dialkylamino, arylamino, alkoxy, aryloxy, nitro, cyano, sulfo, thiol, imine, sulfonyl, sulfenyl, sulfinyl, sulfamyl, carboxalkoxy, carboxamido, phosphonyl, phosphinyl, phosphoryl, phosphino, thioester, thioether, anhydride, oximino, hydrazino, carbamyl, phospho, phosphonato, and any other viable functional group, provided the substituted organic acid salt additive functions to improve the sweet taste of the at least one natural and/or synthetic high-potency sweetener.

Suitable sweet taste improving inorganic acid additives for use in embodiments of this invention include, but are not limited to, phosphoric acid, phosphorous acid, polyphosphoric acid, hydrochloric acid, sulfuric acid, carbonic acid, sodium dihydrogen phosphate, and their corresponding alkali or alkaline earth metal salts thereof (e.g., inositol hexaphosphate Mg/Ca).

Suitable sweet taste improving bitter compound additives for use in embodiments of this invention include, but are not limited to, caffeine, quinine, urea, bitter orange oil, naringin, quassia, and salts thereof.

Suitable sweet taste improving flavorant and flavoring ingredient additives for use in embodiments of this invention include, but are not limited to, vanillin, vanilla extract, mango extract, cinnamon, citrus, coconut, ginger, viridiflorol, almond, menthol (including menthol without mint), grape skin extract, and grape seed extract. "Flavorant" and "flavoring ingredient" are synonymous, and include natural or synthetic substances or combinations thereof. Flavorants also include any other substance which imparts flavor, and may include natural or non-natural (synthetic) substances which are safe for human or animals when used in a generally accepted range. Non-limiting examples of proprietary flavorants include Döhler™ Natural Flavoring Sweetness Enhancer K14323 (Döhler™, Darmstadt, Germany), Symrise™ Natural Flavor Mask for Sweeteners 161453 and 164126 (Symrise, Holzminde™, Germany), Natural Advantage™ Bitterness Blockers 1, 2, 9 and 10 (Natural Advantage™, Freehold, N.J., U.S.A.), and Sucramask™ (Creative Research Management, Stockton, Calif., U.S.A.).

Suitable sweet taste improving polymer additives for use in embodiments of this invention include, but are not limited to, chitosan, pectin, pectic, pectinic, polyuronic, polygalacturonic acid, starch, food hydrocolloid or crude extracts thereof (e.g., gum acacia senegal (Fibergum™), gum acacia seyal, carageenan), poly-L-lysine (e.g., poly-L-α-lysine or poly-L-γ-lysine), poly-L-ornithine (e.g., poly-L-α-ornithine or poly-L-γ-ornithine), polyarginine, polypropylene glycol, polyethylene glycol, poly(ethylene glycol methyl ether), polyaspartic acid, polyglutamic acid, polyethyleneimine, alginic acid, sodium alginate, propylene glycol alginate, sodium hexametaphosphate (SHMP) and its salts, and sodium polyethyleneglycolalginate and other cationic and anionic polymers.

Suitable sweet taste improving protein or protein hydrolysate additives for use in embodiments of this invention include, but are not limited to, bovine serum albumin (BSA), whey protein (including fractions or concentrates thereof such as 90% instant whey protein isolate, 34% whey protein, 50% hydrolyzed whey protein, and 80% whey protein concentrate), soluble rice protein, soy protein, protein isolates, protein hydrolysates, reaction products of protein hydrolysates, glycoproteins, and/or proteoglycans containing amino acids (e.g., glycine, alanine, serine, threonine, asparagine, glutamine, arginine, valine, isoleucine, leucine, norvaline, methionine, proline, tyrosine, hydroxyproline, and the like), collagen (e.g., gelatin), partially hydrolyzed collagen (e.g., hydrolyzed fish collagen), and collagen hydrolysates (e.g., porcine collagen hydrolysate).

Suitable sweet taste improving surfactant additives for use in embodiments of this invention include, but are not limited to, polysorbates (e.g., polyoxyethylene sorbitan monooleate (polysorbate 80), polysorbate 20, polysorbate 60), sodium dodecylbenzenesulfonate, dioctyl sulfosuccinate or dioctyl sulfosuccinate sodium, sodium dodecyl sulfate, cetylpyridinium chloride (hexadecylpyridinium chloride), hexadecyltrimethylammonium bromide, sodium cholate, carbamoyl, choline chloride, sodium glycocholate, sodium taurodeoxycholate, lauric arginate, sodium stearoyl lactylate, sodium taurocholate, lecithins, sucrose oleate esters, sucrose stearate esters, sucrose palmitate esters, sucrose laurate esters, and other emulsifiers, and the like.

Suitable sweet taste improving flavonoid additives for use in embodiments of this invention generally are classified as flavonols, flavones, flavanones, flavan-3-ols, isoflavones, or anthocyanidins. Non-limiting examples of flavonoid additives include catechins (e.g., green tea extracts such as Polyphenon™ 60, Polyphenon™ 30, and Polyphenon™ 25 (Mitsui Norin Co., Ltd., Japan), polyphenols, rutins (e.g., enzyme modified rutin Sanmelin™ AO (San-Ei Gen F.F.I., Inc., Osaka, Japan)), neohesperidin, naringin, neohesperidin dihydrochalcone, and the like.

Suitable sweet taste improving alcohol additives for use in embodiments of this invention include, but are not limited to, ethanol.

Suitable sweet taste improving astringent compound additives include, but are not limited to, tannic acid, europium chloride ($EuCl_3$), gadolinium chloride ($GdCl_3$), terbium chloride ($TbCl_3$), alum, tannic acid, and polyphenols (e.g., tea polyphenols).

Suitable sweet taste improving vitamins include nicotinamide (Vitamin B3) and pyridoxal hydrochloride (Vitamin B6), The sweet taste improving compositions also may comprise other natural and/or synthetic high-potency sweeteners. For example, wherein the functional sweetener composition comprises at least one NHPS, the at least one sweet taste improving composition may comprise a synthetic high-potency sweetener, non-limiting examples of which include sucralose, potassium acesulfame, aspartame, alitame, saccharin, neohesperidin dihydrochalcone, cyclamate, neotame, N—[N-[3-(3-hydroxy-4-methoxyphenyl)propyl]-L-α-aspartyl]-L-phenylalanine 1-methyl ester, N-[N-[3-(3-hydroxy-4-methoxyphenyl)-3-methylbutyl]-L-α-aspartyl]-L-phenylalanine 1-methyl ester, N—[N-[3-(3-methoxy-4-hydroxyphenyl)propyl]-L-α-aspartyl]-L-phenylalanine 1-methyl ester, salts thereof, and the like.

The sweet taste improving compositions also may be in salt form which may be obtained using standard procedures well known in the art. The term "salt" also refers to complexes that retain the desired chemical activity of the sweet taste improving compositions of the present invention and are safe for human or animal consumption in a generally acceptable range. Alkali metal (for example, sodium or potassium) or alkaline earth metal (for example, calcium or magnesium) salts also can be made. Salts also may include combinations of alkali and alkaline earth metals. Non-limiting examples of such salts are (a) acid addition salts formed with inorganic acids and salts formed with organic acids; (b) base addition salts formed with metal cations such as calcium, bismuth, barium, magnesium, aluminum, copper, cobalt, nickel, cadmium, sodium, potassium, and the like, or with a cation formed from ammonia, N,N-dibenzylethylenediamine, D-glucosamine, tetraethylammonium, or ethylenediamine; or (c) combinations of (a) and (b). Thus, any salt forms which may be derived from the sweet taste improving compositions may be used with the embodiments of the present invention as long as the salts of the sweet taste improving additives do not adversely affect the taste of the at least one natural and/or synthetic high-potency sweeteners or the orally ingestible compositions comprising the at least one natural and/or synthetic high-potency sweetener. The salt forms of the additives can be added to the natural and/or synthetic sweetener composition in the same amounts as their acid or base forms.

In particular embodiments, suitable sweet taste improving inorganic salts useful as sweet taste improving additives include, but are not limited to, sodium chloride, potassium chloride, sodium sulfate, potassium citrate, europium chloride ($EuCl_3$), gadolinium chloride ($GdCl_3$), terbium chloride ($TbCl_3$), magnesium sulfate, alum, magnesium chloride, mono-, di-, tri-basic sodium or potassium salts of phosphoric acid (e.g., inorganic phosphates), salts of hydrochloric acid (e.g., inorganic chlorides), sodium carbonate, sodium bisulfate, and sodium bicarbonate. Furthermore, in particular embodiments, suitable organic salts useful as sweet taste improving additives include, but are not limited to, choline chloride, alginic acid sodium salt (sodium alginate), glucoheptonic acid sodium salt, gluconic acid sodium salt (sodium gluconate), gluconic acid potassium salt (potassium gluconate), guanidine HCl, glucosamine HCl, amiloride HCl, monosodium glutamate (MSG), adenosine monophosphate salt, magnesium gluconate, potassium tartrate (monohydrate), and sodium tartrate (dihydrate).

It has been discovered that combinations of at least one natural and/or synthetic high-potency sweetener and at least one sweet taste improving composition improve the temporal profile and/or flavor profile, including the osmotic taste, to be more sugar-like. One of ordinary skill in the art, with the teachings of the present invention, may arrive at all the possible combinations of natural and/or synthetic high-potency sweeteners and sweet taste improving compositions. For example, non-limiting combinations of the natural and/or synthetic high-potency sweetener and sweet taste improving compositions include:
1. at least one natural and/or synthetic high-potency sweetener and at least one carbohydrate;
2. at least one natural and/or synthetic high-potency sweetener and at least one polyol;
3. at least one natural and/or synthetic high-potency sweetener and at least one amino acid;
4. at least one natural and/or synthetic high-potency sweetener and at least one other sweet taste improving additive;
5. at least one natural and/or synthetic high-potency sweetener, at least one carbohydrate, at least one polyol, at least one amino acid, and at least one other sweet taste improving additive;
6. at least one natural and/or synthetic high-potency sweetener, at least one carbohydrate, and at least one polyol;
7. at least one natural and/or synthetic high-potency sweetener, at least one carbohydrate, and at least one amino acid;
8. at least one natural and/or synthetic high-potency sweetener, at least one carbohydrate, and at least one other sweet taste improving additive;
9. at least one natural and/or synthetic high-potency sweetener, at least one polyol, and at least one amino acid;
10. at least one natural and/or synthetic high-potency sweetener, at least one polyol, and at least one other sweet taste improving additive;
11. at least one natural and/or synthetic high-potency sweetener, at least one amino acid, and at least one other sweet taste improving additive;
12. at least one natural and/or synthetic high-potency sweetener, at least one carbohydrate, at least one polyol, and at least one amino acid;
13. at least one natural and/or synthetic high-potency sweetener, at least one carbohydrate, at least one polyol, and at least one other sweet taste improving additive;
14. at least one natural and/or synthetic high-potency sweetener, at least one polyol, at least one amino acid, and at least one other sweet taste improving additive; and
15. at least one natural and/or synthetic high-potency sweetener, at least one carbohydrate, at least one amino acid, and at least one other sweet taste improving additive.

These fifteen major combinations further may be broken down into further combinations in order to improve the overall taste of the natural and/or synthetic high-potency sweetener or the orally ingestible compositions comprising the natural and/or synthetic high-potency sweetener.

As explained above, the sweet taste improving composition is selected from the group consisting of polyols, carbohydrates, amino acids, other sweet taste improving additives, and combinations thereof. The other sweet taste improving additives useful in embodiments of this invention are described hereinabove. In one embodiment, a single sweet taste improving composition may be used with a single natural or synthetic high-potency sweetener and at least one functional ingredient. In another embodiment of the present invention, a single sweet taste improving composition may be used with one or more natural and/or synthetic high-potency sweeteners and at least one functional ingredient. In yet another embodiment, one or more sweet taste improving compositions may be used with a single natural or synthetic high-potency sweetener and at least one functional ingredient. In a further embodiment, there may be a plurality of sweet taste improving compositions used in combination with one or more natural and/or synthetic high-potency sweeteners and at least one functional ingredient. Thus, non-limiting examples of sweet taste improving composition combinations for embodiments of this invention include:
i. at least one polyol, at least one carbohydrate, at least one amino acid, and at least one other sweet taste improving additive;
ii. at least one polyol, at least one carbohydrate, and at least one other sweet taste improving additive;
iii. at least one polyol and at least one other sweet taste improving additive;
iv. at least one polyol and at least one carbohydrate;
v. at least one carbohydrate and at least one other sweet taste improving additive;
vi. at least one polyol and at least one amino acid;
vii. at least one carbohydrate and at least one amino acid;
viii. at least one amino acid and at least one other sweet taste improving additive.

Other sweet taste improving composition combinations in accordance with embodiments of this invention include:
1. at least one polyol, at least one carbohydrate, and at least one amino acid;
2. at least one polyol, at least one carbohydrate, and at least one polyamino acid;
3. at least one polyol, at least one carbohydrate, and at least one sugar acid;
4. at least one polyol, at least one carbohydrate, and at least one nucleotide;
5. at least one polyol, at least one carbohydrate, and at least one organic acid;
6. at least one polyol, at least one carbohydrate, and at least one inorganic acid;
7. at least one polyol, at least one carbohydrate, and at least one bitter compound;
8. at least one polyol, at least one carbohydrate, and at least one flavorant or flavoring ingredient;
9. at least one polyol, at least one carbohydrate, and at least one polymer;
10. at least one polyol, at least one carbohydrate, and at least one protein or protein hydrolysate or protein or protein hydrolysate with low molecular weight amino acid;
11. at least one polyol, at least one carbohydrate, and at least one surfactant;
12. at least one polyol, at least one carbohydrate, and at least one flavonoid;
13. at least one polyol, at least one carbohydrate, and at least one alcohol;
14. at least one polyol, at least one carbohydrate, and at least one emulsifier;
15. at least one polyol, at least one carbohydrate, and at least one inorganic salt,
16. at least one polyol, at least one carbohydrate, and at least one organic salt,
17. at least one polyol, at least one carbohydrate, and at least one amino acid, and at least one other sweet taste improving additive;
18. at least one polyol, at least one carbohydrate, and at least one polyamino acid, and at least one other sweet taste improving additive;
19. at least one polyol, at least one carbohydrate, and at least one sugar acid, and at least one other sweet taste improving additive;

20. at least one polyol, at least one carbohydrate, and at least one nucleotide, and at least one other sweet taste improving additive;
21. at least one polyol, at least one carbohydrate, and at least one organic acid, and at least one other sweet taste improving additive.
22. at least one polyol, at least one carbohydrate, and at least one inorganic acid, and at least one other sweet taste improving additive;
23. at least one polyol, at least one carbohydrate, and at least one bitter compound, and at least one other sweet taste improving additive;
24. at least one polyol, at least one carbohydrate, and at least one flavorant or flavoring ingredient, and at least one other sweet taste improving additive;
25. at least one polyol, at least one carbohydrate, and at least one polymer, and at least one other sweet taste improving additive;
26. at least one polyol, at least one carbohydrate, and at least one protein or protein hydrolysate, and at least one other sweet taste improving additive;
27. at least one polyol, at least one carbohydrate, and at least one surfactant, and at least one other sweet taste improving additive;
28. at least one polyol, at least one carbohydrate, and at least one flavonoid, and at least one other sweet taste improving additive;
29. at least one polyol, at least one carbohydrate, and at least one alcohol, and at least one other sweet taste improving additive;
30. at least one polyol, at least one carbohydrate, at least one amino acid, and at least one polyamino acid;
31. at least one polyol, at least one carbohydrate, at least one amino acid, at least one polyamino acid, and at least one sugar acid;
32. at least one polyol, at least one carbohydrate, at least one amino acid, at least one polyamino acid, at least one sugar acid, and at least one nucleotide;
33. at least one polyol, at least one carbohydrate, at least one amino acid, at least one polyamino acid, at least one sugar acid, at least one nucleotide, and at least one organic acid;
34. at least one polyol, at least one carbohydrate, at least one amino acid, at least one polyamino acid, at least one sugar acid, at least one nucleotide, at least one organic acid, and at least one inorganic acid;
35. at least one polyol, at least one carbohydrate, at least one amino acid, at least one polyamino acid, at least one sugar acid, at least one nucleotide, at least one organic acid, at least one inorganic acid, and at least one bitter compound;
36. at least one polyol, at least one carbohydrate, at least one amino acid, at least one polyamino acid, at least one sugar acid, at least one nucleotide, at least one organic acid, at least one inorganic acid, at least one bitter compound, and at least one polymer;
37. at least one polyol, at least one carbohydrate, at least one amino acid, at least one polyamino acid, at least one sugar acid, at least one nucleotide, at least one organic acid, at least one inorganic acid, at least one bitter compound, at least one polymer, and at least one protein or protein hydrolysate;
38. at least one polyol, at least one carbohydrate, at least one amino acid, at least one polyamino acid, at least one sugar acid, at least one nucleotide, at least one organic acid, at least one inorganic acid, at least one bitter compound, at least one polymer, at least one protein or protein hydrolysate, and at least one surfactant;
39. at least one polyol, at least one carbohydrate, at least one amino acid, at least one polyamino acid, at least one sugar acid, at least one nucleotide, at least one organic acid, at least one inorganic acid, at least one bitter compound, at least one polymer, at least one protein or protein hydrolysate, at least one surfactant, and at least one flavonoid;
40. at least one polyol, at least one carbohydrate, at least one amino acid, at least one polyamino acid, at least one sugar acid, at least one nucleotide, at least one organic acid, at least one inorganic acid, at least one bitter compound, at least one polymer, at least one protein or protein hydrolysate, at least one surfactant, at least one flavonoid, and at least one alcohol;
41. at least one polyol, at least one carbohydrate, at least one amino acid, and at least one sugar acid;
42. at least one polyol, at least one carbohydrate, at least one amino acid, and at least one nucleotide;
43. at least one polyol, at least one carbohydrate, at least one amino acid, and at least one organic acid;
44. at least one polyol, at least one carbohydrate, at least one amino acid, and at least one inorganic acid;
45. at least one polyol, at least one carbohydrate, at least one amino acid, and at least one bitter compound;
46. at least one polyol, at least one carbohydrate, at least one amino acid, and at least one polymer;
47. at least one polyol, at least one carbohydrate, at least one amino acid, and at least one protein or protein hydrolysate;
48. at least one polyol, at least one carbohydrate, at least one amino acid, and at least one surfactant;
49. at least one polyol, at least one carbohydrate, at least one amino acid, and at least one flavonoid;
50. at least one polyol, at least one carbohydrate, at least one amino acid, and at least one alcohol;
51. at least one polyol, at least one carbohydrate, at least one polyamino acid, and at least one sugar acid;
52. at least one polyol, at least one carbohydrate, at least one polyamino acid, and at least one nucleotide;
53. at least one polyol, at least one carbohydrate, at least one polyamino acid, and at least one organic acid;
54. at least one polyol, at least one carbohydrate, at least one polyamino acid, and at least one inorganic acid;
55. at least one polyol, at least one carbohydrate, at least one polyamino acid, and at least one bitter compound;
56. at least one polyol, at least one carbohydrate, at least one polyamino acid, and at least one polymer;
57. at least one polyol, at least one carbohydrate, at least one polyamino acid, and at least one protein or protein hydrolysate;
58. at least one polyol, at least one carbohydrate, at least one polyamino acid, and at least one surfactant;
59. at least one polyol, at least one carbohydrate, at least one polyamino acid, and at least one flavonoid;
60. at least one polyol, at least one carbohydrate, at least one polyamino acid, and at least one alcohol;
61. at least one polyol, at least one carbohydrate, at least one sugar acid, and at least one nucleotide;
62. at least one polyol, at least one carbohydrate, at least one sugar acid, and at least one organic acid;
63. at least one polyol, at least one carbohydrate, at least one sugar acid, and at least one inorganic acid;
64. at least one polyol, at least one carbohydrate, at least one sugar acid, and at least one bitter compound;

65. at least one polyol, at least one carbohydrate, at least one sugar acid, and at least one polymer;
66. at least one polyol, at least one carbohydrate, at least one sugar acid, and at least one protein or protein hydrolysate;
67. at least one polyol, at least one carbohydrate, at least one sugar acid, and at least one surfactant;
68. at least one polyol, at least one carbohydrate, at least one sugar acid, and at least one flavonoid;
69. at least one polyol, at least one carbohydrate, at least one sugar acid, and at least one alcohol;
70. at least one polyol, at least one carbohydrate, at least one nucleotide, and at least one organic acid;
71. at least one polyol, at least one carbohydrate, at least one nucleotide, and at least one inorganic acid;
72. at least one polyol, at least one carbohydrate, at least one nucleotide, and at least one bitter compound;
73. at least one polyol, at least one carbohydrate, at least one nucleotide, and at least one polymer;
74. at least one polyol, at least one carbohydrate, at least one nucleotide, and at least one protein or protein hydrolysate;
75. at least one polyol, at least one carbohydrate, at least one nucleotide, and at least one surfactant;
76. at least one polyol, at least one carbohydrate, at least one nucleotide, and at least one flavonoid;
77. at least one polyol, at least one carbohydrate, at least one nucleotide, and at least one alcohol;
78. at least one polyol, at least one carbohydrate, at least one organic acid, and at least one inorganic acid;
79. at least one polyol, at least one carbohydrate, at least one organic acid, and at least one bitter compound;
80. at least one polyol, at least one carbohydrate, at least one organic acid, and at least one polymer;
81. at least one polyol, at least one carbohydrate, at least one organic acid, and at least one protein or protein hydrolysate;
82. at least one polyol, at least one carbohydrate, at least one organic acid, and at least one surfactant;
83. at least one polyol, at least one carbohydrate, at least one organic acid, and at least one flavonoid;
84. at least one polyol, at least one carbohydrate, at least one organic acid, and at least one alcohol;
85. at least one polyol, at least one carbohydrate, at least one inorganic acid, and at least one bitter compound;
86. at least one polyol, at least one carbohydrate, at least one inorganic acid, and at least one polymer;
87. at least one polyol, at least one carbohydrate, at least one inorganic acid, and at least one protein or protein hydrolysate;
88. at least one polyol, at least one carbohydrate, at least one inorganic acid, and at least one surfactant;
89. at least one polyol, at least one carbohydrate, at least one inorganic acid, and at least one flavonoid;
90. at least one polyol, at least one carbohydrate, at least one inorganic acid, and at least one alcohol;
91. at least one polyol, at least one carbohydrate, at least one bitter compound, and at least one polymer;
92 at least one polyol, at least one carbohydrate, at least one bitter compound, and at least one protein or protein hydrolysate;
93. at least one polyol, at least one carbohydrate, at least one bitter compound, and at least one surfactant;
94. at least one polyol, at least one carbohydrate, at least one bitter compound, and at least one flavonoid;
95. at least one polyol, at least one carbohydrate, at least one bitter compound, and at least one alcohol;
96. at least one polyol, at least one carbohydrate, at least one polymer, and at least one protein or protein hydrolysate;
97. at least one polyol, at least one carbohydrate, at least one polymer, and at least one surfactant;
98. at least one polyol, at least one carbohydrate, at least one polymer, and at least one flavonoid;
99. at least one polyol, at least one carbohydrate, at least one polymer, and at least one alcohol;
100. at least one polyol, at least one carbohydrate, at least one protein or protein hydrolysate, and at least one surfactant;
101. at least one polyol, at least one carbohydrate, at least one protein or protein hydrolysate, and at least one flavonoid;
102. at least one polyol, at least one carbohydrate, at least one surfactant, and at least one flavonoid;
103. at least one polyol, at least one carbohydrate, at least one surfactant, and at least one alcohol; and
104. at least one polyol, at least one carbohydrate, at least one flavonoid, and at least one alcohol.

Other sweet taste improving composition combinations in accordance with embodiments of this invention include:
1. at least one polyol and at least one amino acid;
2. at least one polyol and at least one polyamino acid;
3. at least one polyol and at least one sugar acid;
4. at least one polyol and at least one nucleotide;
5. at least one polyol and at least one organic acid;
6. at least one polyol and at least one inorganic acid;
7. at least one polyol and at least one bitter compound;
8. at least one polyol and at least one flavorant or flavoring ingredient;
9. at least one polyol and at least one polymer;
10. at least one polyol and at least one protein or protein hydrolysate;
11. at least one polyol and at least one surfactant;
12. at least one polyol and at least one flavonoid;
13. at least one polyol and at least one alcohol;
14. at least one polyol and at least one emulsifier;
15. at least one polyol and at least one inorganic salt;
16. at least one polyol and at least one organic salt;
17. at least one polyol and at least one protein or protein hydrolysate or mixture of low molecular weight amino acids;
18. at least one polyol, at least one amino acid, and at least one other sweet taste improving additive;
19. at least one polyol, at least one polyamino acid, and at least one other sweet taste improving additive;
20. at least one polyol, at least one sugar acid, and at least one other sweet taste improving additive;
21. at least one polyol, at least one nucleotide, and at least one other sweet taste improving additive;
22. at least one polyol, at least one organic acid, and at least one other sweet taste improving additive;
23. at least one polyol, at least one inorganic acid, and at least one other sweet taste improving additive;
24. at least one polyol, at least one bitter compound, and at least one other sweet taste improving additive;
25. at least one polyol, at least one flavorant or flavoring ingredient, and at least one other sweet taste improving additive;
26. at least one polyol, at least one polymer, and at least one other sweet taste improving additive;
27. at least one polyol, at least one protein or protein hydrolysate, and at least one other sweet taste improving additive;

28. at least one polyol, at least one surfactant, and at least one other sweet taste improving additive;
29. at least one polyol, at least one flavonoid, and at least one other sweet taste improving additive;
30. at least one polyol, at least one alcohol, and at least one other sweet taste improving additive;
31. at least one polyol, at least one amino acid, and at least one polyamino acid;
32. at least one polyol, at least one amino acid, at least one polyamino acid, and at least one sugar acid;
33. at least one polyol, at least one amino acid, at least one polyamino acid, at least one sugar acid, and at least one nucleotide;
34. at least one polyol, at least one amino acid, at least one polyamino acid, at least one sugar acid, at least one nucleotide, and at least one organic acid;
35. at least one polyol, at least one amino acid, at least one polyamino acid, at least one sugar acid, at least one nucleotide, at least one organic acid, and at least one inorganic acid;
36. at least one polyol, at least one amino acid, at least one polyamino acid, at least one sugar acid, at least one nucleotide, at least one organic acid, at least one inorganic acid, and at least one bitter compound;
37. at least one polyol, at least one amino acid, at least one polyamino acid, at least one sugar acid, at least one nucleotide, at least one organic acid, at least one inorganic acid, at least one bitter compound, and at least one polymer;
38. at least one polyol, at least one amino acid, at least one polyamino acid, at least one sugar acid, at least one nucleotide, at least one organic acid, at least one inorganic acid, at least one bitter compound, at least one polymer, and at least one protein or protein hydrolysate;
39. at least one polyol, at least one amino acid, at least one polyamino acid, at least one sugar acid, at least one nucleotide, at least one organic acid, at least one inorganic acid, at least one bitter compound, at least one polymer, at least one protein or protein hydrolysate, and at least one surfactant;
40. at least one polyol, at least one amino acid, at least one polyamino acid, at least one sugar acid, at least one nucleotide, at least one organic acid, at least one inorganic acid, at least one bitter compound, at least one polymer, at least one protein or protein hydrolysate, at least one surfactant, and at least one flavonoid;
41. at least one polyol, at least one amino acid, at least one polyamino acid, at least one sugar acid, at least one nucleotide, at least one organic acid, at least one inorganic acid, at least one bitter compound, at least one polymer, at least one protein or protein hydrolysate, at least one surfactant, at least one flavonoid, and at least one alcohol.
42. at least one polyol, at least one amino acid, and at least one sugar acid;
43. at least one polyol, at least one amino acid, and at least one nucleotide;
44. at least one polyol, at least one amino acid, and at least one organic acid;
45. at least one polyol, at least one amino acid, and at least one inorganic acid;
46. at least one polyol, at least one amino acid, and at least one bitter compound;
47. at least one polyol, at least one amino acid, and at least one polymer;
48. at least one polyol, at least one amino acid, and at least one protein or protein hydrolysate;
49. at least one polyol, at least one amino acid, and at least one surfactant;
50. at least one polyol, at least one amino acid, and at least one flavonoid;
51. at least one polyol, at least one amino acid, and at least one alcohol;
52. at least one polyol, at least one polyamino acid, and at least one sugar acid;
53. at least one polyol, at least one polyamino acid, and at least one nucleotide;
54. at least one polyol, at least one polyamino acid, and at least one organic acid;
55. at least one polyol, at least one polyamino acid, and at least one organic salt;
56. at least one polyol, at least one polyamino acid, and at least one inorganic acid;
57. at least one polyol, at least one polyamino acid, and at least one inorganic salt;
58. at least one polyol, at least one polyamino acid, and at least one bitter compound;
59. at least one polyol, at least one polyamino acid, and at least one polymer;
60. at least one polyol, at least one polyamino acid, and at least one protein or protein hydrolysate;
61. at least one polyol, at least one polyamino acid, and at least one surfactant;
62. at least one polyol, at least one polyamino acid, and at least one flavonoid;
63. at least one polyol, at least one polyamino acid, and at least one alcohol;
64. at least one polyol, at least one sugar acid, and at least one nucleotide;
65. at least one polyol, at least one sugar acid, and at least one organic acid;
66. at least one polyol, at least one sugar acid, and at least one inorganic acid;
67. at least one polyol, at least one sugar acid, and at least one bitter compound;
68. at least one polyol, at least one sugar acid, and at least one polymer;
69. at least one polyol, at least one sugar acid, and at least one protein or protein hydrolysate;
70. at least one polyol, at least one sugar acid, and at least one surfactant;
71. at least one polyol, at least one sugar acid, and at least one flavonoid;
72. at least one polyol, at least one sugar acid, and at least one alcohol;
73. at least one polyol, at least one nucleotide, and at least one organic acid;
74 at least one polyol, at least one nucleotide, and at least one inorganic acid;
75. at least one polyol, at least one nucleotide, and at least one bitter compound;
76. at least one polyol, at least one nucleotide, and at least one polymer;
77. at least one polyol, at least one nucleotide, and at least one protein or protein hydrolysate;
78. at least one polyol, at least one nucleotide, and at least one surfactant;
79. at least one polyol, at least one nucleotide, and at least one flavonoid;
80. at least one polyol, at least one nucleotide, and at least one alcohol;
81. at least one polyol, at least one organic acid, and at least one inorganic acid;

82. at least one polyol, at least one organic acid, and at least one bitter compound;
83. at least one polyol, at least one organic acid, and at least one polymer;
84. at least one polyol, at least one organic acid, and at least one protein or protein hydrolysate;
85. at least one polyol, at least one organic acid, and at least one surfactant;
86. at least one polyol, at least one organic acid, and at least one flavonoid;
87. at least one polyol, at least one organic acid, and at least one alcohol;
88. at least one polyol, at least one inorganic acid, and at least one bitter compound;
89. at least one polyol, at least one inorganic acid, and at least one polymer;
90. at least one polyol, at least one inorganic acid, and at least one protein or protein hydrolysate;
91. at least one polyol, at least one inorganic acid, and at least one surfactant;
92. at least one polyol, at least one inorganic acid, and at least one flavonoid;
93. at least one polyol, at least one inorganic acid, and at least one alcohol;
94. at least one polyol, at least one bitter compound, and at least one polymer;
95. at least one polyol, at least one bitter compound, and at least one protein or protein hydrolysate;
96. at least one polyol, at least one bitter compound, and at least one surfactant;
97. at least one polyol, at least one bitter compound, and at least one flavonoid;
98. at least one polyol, at least one bitter compound, and at least one alcohol;
99. at least one polyol, at least one polymer, and at least one protein or protein hydrolysate;
100. at least one polyol, at least one polymer, and at least one surfactant;
101. at least one polyol, at least one polymer, and at least one flavonoid;
102. at least one polyol, at least one polymer, and at least one alcohol;
103. at least one polyol, at least one protein or protein hydrolysate, and at least one surfactant;
104. at least one polyol, at least one protein or protein hydrolysate, and at least one flavonoid;
105. at least one polyol, at least one surfactant, and at least one flavonoid;
106. at least one polyol, at least one surfactant, and at least one alcohol;
107. at least one polyol, at least one flavonoid, and at least one alcohol;
108. at least one sweet taste improving additive and erythritol;
109. at least one sweet taste improving additive and maltitol;
110. at least one sweet taste improving additive and mannitol;
11. at least one sweet taste improving additive and sorbitol;
112. at least one sweet taste improving additive and lactitol;
113. at least one sweet taste improving additive and xylitol;
114. at least one sweet taste improving additive and isomalt;
115. at least one sweet taste improving additive and propylene glycol;
116. at least one sweet taste improving additive and glycerol;
117. at least one sweet taste improving additive and palatinose;
118. at least one sweet taste improving additive and reduced isomalto-oligosaccharides;
119. at least one sweet taste improving additive and reduced xylo-oligosaccharides;
120. at least one sweet taste improving additive and reduced gentio-oligosaccharides;
121. at least one sweet taste improving additive and reduced maltose syrup;
122. at least one sweet taste improving additive and reduced glucose syrup;
123. at least one sweet taste improving additive, erythritol, and at least one other polyol;
124. at least one sweet taste improving additive, maltitol, and at least one other polyol;
125. at least one sweet taste improving additive, mannitol, and at least one other polyol;
126. at least one sweet taste improving additive, sorbitol, and at least one other polyol;
127. at least one sweet taste improving additive, lactitol, and at least one other polyol;
128. at least one sweet taste improving additive, xylitol, and at least one other polyol;
129. at least one sweet taste improving additive, isomalt, and at least one other polyol;
130. at least one sweet taste improving additive, propylene glycol, and at least one other polyol;
131. at least one sweet taste improving additive, glycerol, and at least one other polyol;
132. at least one sweet taste improving additive, palatinose, and at least one other polyol;
133. at least one sweet taste improving additive, reduced isomalto-oligosaccharides, and at least one other polyol;
134. at least one sweet taste improving additive, reduced xylo-oligosaccharides, and at least one other polyol;
135. at least one sweet taste improving additive, reduced gentio-oligosaccharides, and at least one other polyol;
136. at least one sweet taste improving additive, reduced maltose syrup, and at least one other polyol; and
137. at least one sweet taste improving additive, reduced glucose syrup, and at least one other polyol.

Other sweet taste improving composition combinations in accordance with embodiments of this invention include:
1. at least one polyol and tagatose;
2. at least one polyol and trehalose;
3. at least one polyol and galactose;
4. at least one polyol and rhamnose;
5. at least one polyol and dextrin;
6. at least one polyol and cyclodextrin;
7. at least one polyol and α-cyclodextrin, β-cyclodextrin, or γ-cyclodextrin;
8. at least one polyol and maltodextrin;
9. at least one polyol and dextran;
10. at least one polyol and sucrose;
11. at least one polyol and glucose;
12. at least one polyol and fructose;
13. at least one polyol and threose;
14. at least one polyol and arabinose;
15. at least one polyol and xylose;
16. at least one polyol and lyxose;
17. at least one polyol and allose;
18. at least one polyol and altrose;
19. at least one polyol and mannose;
20. at least one polyol and idose;

21. at least one polyol and talose;
22. at least one polyol and lactose;
23. at least one polyol and maltose;
24. at least one polyol and invert sugar;
25. at least one polyol and trehalose;
26. at least one polyol and isotrehalose;
27. at least one polyol and neotrehalose;
28. at least one polyol and palatinose;
29. at least one polyol and galactose;
30. at least one polyol and beet oligosaccharides;
31. at least one polyol and isomalto-oligosaccharides;
32. at least one polyol and isomaltose;
33. at least one polyol and isomaltotriose;
34. at least one polyol and panose;
35. at least one polyol and xylo-oligosaccharides;
36. at least one polyol and xylotriose;
37. at least one polyol and xylobiose;
38. at least one polyol and gentio-oligosaccharides;
39. at least one polyol and gentiobiose.
40. at least one polyol and gentiotriose;
41. at least one polyol and gentiotetraose;
42. at least one polyol and sorbose;
43. at least one polyol and nigero-oligosaccharides;
44. at least one polyol and palatinose oligosaccharides;
45. at least one polyol and fucose;
46. at least one polyol and fructooligosaccharides;
47. at least one polyol and kestose;
48. at least one polyol and nystose;
49. at least one polyol and maltotetraol;
50. at least one polyol and maltotriol;
51. at least one polyol and malto-oligosaccharides;
52. at least one polyol and maltotriose;
53. at least one polyol and maltotetraose;
54. at least one polyol and maltopentaose;
55. at least one polyol and maltohexaose;
56. at least one polyol and maltoheptaose;
57. at least one polyol and lactulose;
58. at least one polyol and melibiose;
59. at least one polyol and raffinose;
60. at least one polyol and rhamnose;
61. at least one polyol and ribose;
62. at least one polyol and isomerized liquid sugars;
63. at least one polyol and high fructose corn syrup (e.g. HFCS55,HFCS42, or HFCS90) or starch syrup;
64. at least one polyol and coupling sugars;
65. at least one polyol and soybean oligosaccharides;
66. at least one polyol and glucose syrup;
67. at least one polyol, tagatose, and at least one other carbohydrate;
68. at least one polyol, trehalose, and at least one other carbohydrate;
69. at least one polyol, galactose, and at least one other carbohydrate;
70. at least one polyol, rhamnose, and at least one other carbohydrate;
71. at least one polyol, dextrin, and at least one other carbohydrate;
72. at least one polyol, cyclodextrin, and at least one other carbohydrate;
73. at least one polyol, β-cyclodextrin, and at least one other carbohydrate;
74. at least one polyol, maltodextrin, and at least one other carbohydrate;
75. at least one polyol, dextran, and at least one other carbohydrate;
76. at least one polyol, sucrose, and at least one other carbohydrate;
77. at least one polyol, glucose, and at least one other carbohydrate;
78. at least one polyol, fructose, and at least one other carbohydrate;
79. at least one polyol, threose, and at least one other carbohydrate;
80. at least one polyol, arabinose, and at least one other carbohydrate;
81. at least one polyol, xylose, and at least one other carbohydrate;
82. at least one polyol, lyxose, and at least one other carbohydrate;
83. at least one polyol, allose, and at least one other carbohydrate;
84. at least one polyol, altrose, and at least one other carbohydrate;
85. at least one polyol, mannose, and at least one other carbohydrate;
86. at least one polyol, idose, and at least one other carbohydrate;
87. at least one polyol, talose, and at least one other carbohydrate;
88. at least one polyol, lactose, and at least one other carbohydrate;
89. at least one polyol, maltose, and at least one other carbohydrate;
90. at least one polyol, invert sugar, and at least one other carbohydrate;
91. at least one polyol, trehalose, and at least one other carbohydrate;
92. at least one polyol, isotrehalose, and at least one other carbohydrate;
93. at least one polyol, neotrehalose, and at least one other carbohydrate;
94. at least one polyol, palatinose, and at least one other carbohydrate;
95. at least one polyol, galactose, and at least one other carbohydrate;
96. at least one polyol, beet oligosaccharides, and at least one other carbohydrate;
97. at least one polyol, isomalto-oligosaccharides, and at least one other carbohydrate;
98. at least one polyol, isomaltose, and at least one other carbohydrate;
99. at least one polyol, isomaltotriose, and at least one other carbohydrate;
100. at least one polyol, panose, and at least one other carbohydrate;
101. at least one polyol, xylo-oligosaccharides, and at least one other carbohydrate;
102. at least one polyol, xylotriose, and at least one other carbohydrate;
103. at least one polyol, xylobiose, and at least one other carbohydrate;
104. at least one polyol, gentio-oligoscacchorides, and at least one other carbohydrate;
105. at least one polyol, gentiobiose, and at least one other carbohydrate;
106. at least one polyol, gentiotriose, and at least one other carbohydrate;
107. at least one polyol, gentiotetraose, and at least one other carbohydrate;
108. at least one polyol, sorbose, and at least one other carbohydrate;
109. at least one polyol, nigero-oligosaccharides, and at least one other carbohydrate;

110. at least one polyol, palatinose oligosaccharides, and at least one other carbohydrate;
111. at least one polyol, fucose, and at least one other carbohydrate;
112. at least one polyol, fruetooligosaccharides, and at least one other carbohydrate;
113. at least one polyol, kestose, and at least one other carbohydrate;
114. at least one polyol, nystose, and at least one other carbohydrate;
115. at least one polyol, maltotetraol, and at least one other carbohydrate;
116. at least one polyol, maltotriol, and at least one other carbohydrate;
117. at least one polyol, malto-oligosaccharides, and at least one other carbohydrate;
118. at least one polyol, maltotriose, and at least one other carbohydrate;
119. at least one polyol, maltotetraose, and at least one other carbohydrate;
120. at least one polyol, maltopentaose, and at least one other carbohydrate;
121. at least one polyol, maltohexaose, and at least one other carbohydrate;
122. at least one polyol, maltoheptaose, and at least one other carbohydrate;
123. at least one polyol, lactulose, and at least one other carbohydrate;
124. at least one polyol, melibiose, and at least one other carbohydrate;
125. at least one polyol, raffinose, and at least one other carbohydrate;
126. at least one polyol, rhamnose, and at least one other carbohydrate;
127. at least one polyol, ribose, and at least one other carbohydrate;
128. at least one polyol, isomerized liquid sugars, and at least one other carbohydrate;
129. at least one polyol, high fructose corn syrup (e.g. HFCS55, HFCS42, or HFCS90) or starch syrup, and at least one other carbohydrate;
130. at least one polyol, coupling sugars, and at least one other carbohydrate;
131. at least one polyol, soybean oligosaccharides, and at least one other carbohydrate;
132. at least one polyol, glucose syrup, and at least one other carbohydrate;
133. at least one carbohydrate and erythritol;
134. at least one carbohydrate and maltitol;
135. at least one carbohydrate and mannitol;
136. at least one carbohydrate and sorbitol;
137. at least one carbohydrate and lactitol;
138. at least one carbohydrate and xylitol;
139. at least one carbohydrate and isomalt;
140. at least one carbohydrate and propylene glycol;
141. at least one carbohydrate and glycerol;
142. at least one carbohydrate and palatinose;
143. at least one carbohydrate and reduced isomalto-oligosaccharides;
144. at least one carbohydrate and reduced xylo-oligosaccharides;
145. at least one carbohydrate and reduced gentio-oligosaccharides;
146. at least one carbohydrate and reduced maltose syrup;
147. at least one carbohydrate and reduced glucose syrup;
148. at least one carbohydrate, erythritol, and at least one other polyol;
149. at least one carbohydrate, maltitol, and at least one other polyol;
150. at least one carbohydrate, mannitol, and at least one other polyol;
151. at least one carbohydrate, sorbitol, and at least one other polyol;
152. at least one carbohydrate, lactitol, and at least one other polyol;
153. at least one carbohydrate, xylitol, and at least one other polyol;
154. at least one carbohydrate, isomalt, and at least one other polyol;
155. at least one carbohydrate, propylene glycol, and at least one other polyol;
156. at least one carbohydrate, glycerol, and at least one other polyol;
157. at least one carbohydrate, palatinose, and at least one other polyol;
158. at least one carbohydrate, reduced isomalto-oligosaccharides, and at least one other polyol;
159. at least one carbohydrate, reduced xylo-oligosaccharides, and at least one other polyol;
160. at least one carbohydrate, reduced gentio-oligosaccharides, and at least one other polyol;
161. at least one carbohydrate, reduced maltose syrup, and at least one other polyol; and
162. at least one carbohydrate, reduced glucose syrup, and at least one other polyol.

Other sweet taste improving composition combinations in accordance with embodiments of this invention include, 1. at least one carbohydrate and at least one amino acid;
2. at least one carbohydrate and at least one polyamino acid;
3. at least one carbohydrate and at least one sugar acid;
4. at least one carbohydrate and at least one nucleotide;
5. at least one carbohydrate and at least one organic acid;
6. at least one carbohydrate and at least one inorganic acid;
7. at least one carbohydrate and at least one bitter compound;
8. at least one carbohydrate and at least one flavorant or flavoring ingredient;
9. at least one carbohydrate and at least one polymer:
10. at least one carbohydrate and at least one protein or protein hydrolysate;
11. at least one carbohydrate and at least one surfactant;
12, at least one carbohydrate and at least one flavonoid;
13. at least one carbohydrate and at least one alcohol;
14. at least one carbohydrate and at least one protein or protein hydrolysate or mixture of low molecular weight amino acids;
15. at least one carbohydrate and at least one emulsifier;
16. at least one carbohydrate and at least one inorganic salt;
17. at least one carbohydrate, at least one amino acid, and at least one other sweet taste improving additive;
18. at least one carbohydrate, at least one polyamino acid, and at least one other sweet taste improving additive;
19. at least one carbohydrate, at least one sugar acid, and at least one other sweet taste improving additive;
20. at least one carbohydrate, at least one nucleotide, and at least one other sweet taste improving additive;
21. at least one carbohydrate, at least one organic acid, and at least one other sweet taste improving additive;
22. at least one carbohydrate, at least one inorganic acid, and at least one other sweet taste improving additive;
23. at least one carbohydrate, at least one bitter compound, and at least one other sweet taste improving additive;

24. at least one carbohydrate, at least one flavorant or flavoring ingredient, and at least one other sweet taste improving additive;
25. at least one carbohydrate, at least one polymer, and at least one other sweet taste improving additive;
26. at least one carbohydrate, at least one protein or protein hydrolysate, and at least one other sweet taste improving additive;
27. at least one carbohydrate, at least one surfactant, and at least one other sweet taste improving additive;
28. at least one carbohydrate, at least one flavonoid, and at least one other sweet taste improving additive;
29. at least one carbohydrate, at least one alcohol, and at least one other sweet taste improving additive;
30. at least one carbohydrate, at least one amino acid, and at least one polyamino acid;
31. at least one carbohydrate, at least one amino acid, at least one polyamino acid, and at least one sugar acid;
32. at least one carbohydrate, at least one amino acid, at least one polyamino acid, at least one sugar acid, and at least one nucleotide;
33. at least one carbohydrate, at least one amino acid, at least one polyamino acid, at least one sugar acid, at least one nucleotide, and at least one organic acid;
34. at least one carbohydrate, at least one amino acid, at least one polyamino acid, at least one sugar acid, at least one nucleotide, at least one organic acid, and at least one inorganic acid;
35. at least one carbohydrate, at least one amino acid, at least one polyamino acid, at least one sugar acid, at least one nucleotide, at least one organic acid, at least one inorganic acid, and at least one bitter compound;
36. at least one carbohydrate, at least one amino acid, at least one polyamino acid, at least one sugar acid, at least one nucleotide, at least one organic acid, at least one inorganic acid, at least one bitter compound, and at least one polymer;
37. at least one carbohydrate, at least one amino acid, at least one polyamino acid, at least one sugar acid, at least one nucleotide, at least one organic acid, at least one inorganic acid, at least one bitter compound, at least one polymer, and at least one protein or protein hydrolysate;
38. at least one carbohydrate, at least one amino acid, at least one polyamino acid, at least one sugar acid, at least one nucleotide, at least one organic acid, at least one inorganic acid, at least one bitter compound, at least one polymer, at least one protein or protein hydrolysate, and at least one surfactant;
39. at least one carbohydrate, at least one amino acid, at least one polyamino acid, at least one sugar acid, at least one nucleotide, at least one organic acid, at least one inorganic acid, at least one bitter compound, at least one polymer, at least one protein or protein hydrolysate, at least one surfactant, and at least one flavonoid;
40. at least one carbohydrate, at least one amino acid, at least one polyamino acid, at least one sugar acid, at least one nucleotide, at least one organic acid, at least one inorganic acid, at least one bitter compound, at least one polymer, at least one protein or protein hydrolysate, at least one surfactant, at least one flavonoid, and at least one alcohol;
41. at least one carbohydrate, at least one amino acid, and at least one sugar acid;
42. at least one carbohydrate, at least one amino acid, and at least one nucleotide;
43. at least one carbohydrate, at least one amino acid, and at least one organic acid;
44. at least one carbohydrate, at least one amino acid, and at least one inorganic acid;
45. at least one carbohydrate, at least one amino acid, and at least one bitter compound;
46. at least one carbohydrate, at least one amino acid, and at least one polymer;
47. at least one carbohydrate, at least one amino acid, and at least one protein or protein hydrolysate;
48. at least one carbohydrate, at least one amino acid, and at least one surfactant;
49. at least one carbohydrate, at least one amino acid, and at least one flavonoid;
50. at least one carbohydrate, at least one amino acid, and at least one alcohol;
51. at least one carbohydrate, at least one polyamino acid, and at least one sugar acid;
52. at least one carbohydrate, at least one polyamino acid, and at least one nucleotide;
53. at least one carbohydrate, at least one polyamino acid, and at least one organic acid;
54. at least one carbohydrate, at least one polyamino acid, and at least one inorganic acid;
55. at least one carbohydrate, at least one polyamino acid, and at least one bitter compound;
56. at least one carbohydrate, at least one polyamino acid, and at least one polymer;
57. at least one carbohydrate, at least one polyamino acid, and at least one protein or protein hydrolysate;
58. at least one carbohydrate, at least one polyamino acid, and at least one surfactant;
59. at least one carbohydrate, at least one polyamino acid, and at least one flavonoid;
60. at least one carbohydrate, at least one polyamino acid, and at least one alcohol;
61. at least one carbohydrate, at least one sugar acid, and at least one nucleotide;
62. at least one carbohydrate, at least one sugar acid, and at least one organic acid;
63. at least one carbohydrate, at least one sugar acid, and at least one inorganic acid;
64. at least one carbohydrate, at least one sugar acid, and at least one bitter compound;
65. at least one carbohydrate, at least one sugar acid, and at least one polymer;
66. at least one carbohydrate, at least one sugar acid, and at least one protein or protein hydrolysate;
67. at least one carbohydrate, at least one sugar acid, and at least one surfactant;
68. at least one carbohydrate, at least one sugar acid, and at least one flavonoid;
69. at least one carbohydrate, at least one sugar acid, and at least one alcohol;
70. at least one carbohydrate, at least one nucleotide, and at least one organic acid;
71. at least one carbohydrate, at least one nucleotide, and at least one inorganic acid;
72. at least one carbohydrate, at least one nucleotide, and at least one bitter compound;
73. at least one carbohydrate, at least one nucleotide, and at least one polymer;
74. at least one carbohydrate, at least one nucleotide, and at least one protein or protein hydrolysate;
75. at least one carbohydrate, at least one nucleotide, and at least one surfactant;
76. at least one carbohydrate, at least one nucleotide, and at least one flavonoid;

77. at least one carbohydrate, at least one nucleotide, and at least one alcohol;
78. at least one carbohydrate, at least one organic acid, and at least one inorganic acid;
79. at least one carbohydrate, at least one organic acid, and at least one bitter compound;
80. at least one carbohydrate, at least one organic acid, and at least one polymer;
81. at least one carbohydrate, at least one organic acid, and at least one protein or protein hydrolysate;
82. at least one carbohydrate, at least one organic acid, and at least one surfactant;
83. at least one carbohydrate, at least one organic acid, and at least one flavonoid;
84. at least one carbohydrate, at least one organic acid, and at least one alcohol;
85. at least one carbohydrate, at least one inorganic acid, and at least one bitter compound;
86. at least one carbohydrate, at least one inorganic acid, and at least one polymer;
87. at least one carbohydrate, at least one inorganic acid, and at least one protein or protein hydrolysate;
88. at least one carbohydrate, at least one inorganic acid, and at least one surfactant;
89. at least one carbohydrate, at least one inorganic acid, and at least one flavonoid;
90. at least one carbohydrate, at least one inorganic acid, and at least one alcohol;
91. at least one carbohydrate, at least one bitter compound, and at least one polymer;
92. at least one carbohydrate, at least one bitter compound, and at least one protein or protein hydrolysate;
93. at least one carbohydrate, at least one bitter compound, and at least one surfactant;
94. at least one carbohydrate, at least one bitter compound, and at least one flavonoid;
95. at least one carbohydrate, at least one bitter compound, and at least one alcohol;
96. at least one carbohydrate, at least one polymer, and at least one protein or protein hydrolysate;
97. at least one carbohydrate, at least one polymer, and at least one surfactant;
98. at least one carbohydrate, at least one polymer, and at least one flavonoid;
99. at least one carbohydrate, at least one polymer, and at least one alcohol;
100. at least one carbohydrate, at least one protein or protein hydrolysate, and at least one surfactant;
101. at least one carbohydrate, at least one protein or protein hydrolysate, and at least one flavonoid;
102. at least one carbohydrate, at least one surfactant, and at least one flavonoid;
103. at least one carbohydrate, at least one surfactant, and at least one alcohol;
104. at least one carbohydrate, at least one flavonoid, and at least one alcohol;
105. at least one sweet taste improving additive and D-tagatose;
106. at least one sweet taste improving additive and trehalose;
107. at least one sweet taste improving additive and D-galactose;
108. at least one sweet taste improving additive and rhamnose;
109. at least one sweet taste improving additive and dextrin;
110. at least one sweet taste improving additive and cyclodextrin;
111. at least one sweet taste improving additive and β-cyclodextrin;
112. at least one sweet taste improving additive and maltodextrin;
113. at least one sweet taste improving additive and dextran;
114. at least one sweet taste improving additive and sucrose;
115. at least one sweet taste improving additive and glucose;
116. at least one sweet taste improving additive and fructose;
117. at least one sweet taste improving additive and threose;
118. at least one sweet taste improving additive and arabinose;
119. at least one sweet taste improving additive and xylose;
120. at least one sweet taste improving additive and lyxose;
121. at least one sweet taste improving additive and allose;
122. at least one sweet taste improving additive and altrose;
123. at least one sweet taste improving additive and mannose;
124. at least one sweet taste improving additive and idose;
125. at least one sweet taste improving additive and talose;
126. at least one sweet taste improving additive and lactose;
127. at least one sweet taste improving additive and maltose;
128. at least one sweet taste improving additive and invert sugar;
129. at least one sweet taste improving additive and trehalose;
130. at least one sweet taste improving additive and isotrehalose;
131. at least one sweet taste improving additive and neotrehalose;
132. at least one sweet taste improving additive and palatinose;
133. at least one sweet taste improving additive and galactose;
134. at least one sweet taste improving additive and beet oligosaccharides;
135. at least one sweet taste improving additive and isomalto-oligosaccharides;
136. at least one sweet taste improving additive and isomaltose;
137. at least one sweet taste improving additive and isomaltotriose;
138. at least one sweet taste improving additive and panose;
139. at least one sweet taste improving additive and xylo-oligosaccharides;
140. at least one sweet taste improving additive and xylotriose;
141. at least one sweet taste improving additive and xylobiose;
142. at least one sweet taste improving additive and gentio-oligoscaccharides;
143. at least one sweet taste improving additive and gentiobiose;
144. at least one sweet taste improving additive and gentiotriose;
145. at least one sweet taste improving additive and gentiotetraose;

146. at least one sweet taste improving additive and sorbose;
147. at least one sweet taste improving additive and nigero-oligosaccharides;
148. at least one sweet taste improving additive and palatinose oligosaccharides;
149. at least one sweet taste improving additive and fucose;
150. at least one sweet taste improving additive and fructooligosaccharides;
151. at least one sweet taste improving additive and kestose;
152. at least one sweet taste improving additive and nystose;
153. at least one sweet taste improving additive and maltotetraol;
154. at least one sweet taste improving additive and maltotriol;
155. at least one sweet taste improving additive and malto-oligosaccharides;
156. at least one sweet taste improving additive and maltotriose;
157. at least one sweet taste improving additive and maltotetraose;
158. at least one sweet taste improving additive and maltopentaose;
159. at least one sweet taste improving additive and maltohexaose;
160. at least one sweet taste improving additive and maltoheptaose;
161. at least one sweet taste improving additive and lactulose;
162. at least one sweet taste improving additive and melibiose;
163. at least one sweet taste improving additive and raffinose;
164. at least one sweet taste improving additive and rhamnose;
165. at least one sweet taste improving additive and ribose;
166. at least one sweet taste improving additive and isomerized liquid sugars;
167. at least one sweet taste improving additive and high fructose corn syrup (e.g., HFCS55, HFCS42, or HFCS90) or starch syrup;
168. at least one sweet taste improving additive and coupling sugars;
169. at least one sweet taste improving additive and soybean oligosaccharides;
170. at least one sweet taste improving additive and glucose syrup;
171. at least one sweet taste improving additive, D-tagatose, and at least one other carbohydrate;
172. at least one sweet taste improving additive, trehalose, and at least one other carbohydrate;
173. at least one sweet taste improving additive, D-galactose, and at least one other carbohydrate;
174. at least one sweet taste improving additive, rhamnose, and at least one other carbohydrate;
175. at least one sweet taste improving additive, dextrin, and at least one other carbohydrate;
176. at least one sweet taste improving additive, cyclodextrin, and at least one other carbohydrate;
177. at least one sweet taste improving additive, β-cyclodextrin, and at least one other carbohydrate;
178. at least one sweet taste improving additive, maltodextrin, and at least one other carbohydrate;
179. at least one sweet taste improving additive, dextran, and at least one other carbohydrate;
180. at least one sweet taste improving additive, sucrose, and at least one other carbohydrate;
181. at least one sweet taste improving additive, glucose, and at least one other carbohydrate;
182. at least one sweet taste improving additive, fructose, and at least one other carbohydrate;
183. at least one sweet taste improving additive, threose, and at least one other carbohydrate;
184. at least one sweet taste improving additive, arabinose, and at least one other carbohydrate;
185. at least one sweet taste improving additive, xylose, and at least one other carbohydrate;
186. at least one sweet taste improving additive, lyxose, and at least one other carbohydrate;
187. at least one sweet taste improving additive, allose, and at least one other carbohydrate.
188. at least one sweet taste improving additive, altrose, and at least one other carbohydrate;
189. at least one sweet taste improving additive, mannose, and at least one other carbohydrate;
190. at least one sweet taste improving additive, idose, and at least one other carbohydrate;
191. at least one sweet taste improving additive, talose, and at least one other carbohydrate;
192. at least one sweet taste improving additive, lactose, and at least one other carbohydrate;
193. at least one sweet taste improving additive, maltose, and at least one other carbohydrate;
194. at least one sweet taste improving additive, invert sugar, and at least one other carbohydrate;
195. at least one sweet taste improving additive, trehalose, and at least one other carbohydrate;
196. at least one sweet taste improving additive, isotrehalose, and at least one other carbohydrate;
197. at least one sweet taste improving additive, neotrehalose, and at least one other carbohydrate;
198. at least one sweet taste improving additive, palatinose, and at least one other carbohydrate;
199. at least one sweet taste improving additive, galactose, and at least one other carbohydrate;
200. at least one sweet taste improving additive, beet oligosaccharides, and at least one other carbohydrate;
201. at least one sweet taste improving additive, isomaltooligosaccharides, and at least one other carbohydrate;
202. at least one sweet taste improving additive, isomaltose, and at least one other carbohydrate;
203. at least one sweet taste improving additive, isomaltotriose, and at least one other carbohydrate;
204. at least one sweet taste improving additive, panose, and at least one other carbohydrate;
205. at least one sweet taste improving additive, xylooligosaccharides, and at least one other carbohydrate;
206. at least one sweet taste improving additive, xylotriose, and at least one other carbohydrate;
207. at least one sweet taste improving additive, xylobiose, and at least one other carbohydrate;
208. at least one sweet taste improving additive, gentiooligoscaccharides, and at least one other carbohydrate;
209. at least one sweet taste improving additive, gentiobiose, and at least one other carbohydrate;
210. at least one sweet taste improving additive, gentiotriose, and at least one other carbohydrate;
211. at least one sweet taste improving additive, gentiotetraose, and at least one other carbohydrate;
212. at least one sweet taste improving additive, sorbose, and at least one other carbohydrate;

213. at least one sweet taste improving additive, nigero-oligosaccharides, and at least one other carbohydrate;
214. at least one sweet taste improving additive, palatinose oligosaccharides, and at least one other carbohydrate;
215. at least one sweet taste improving additive, fucose, and at least one other carbohydrate;
216. at least one sweet taste improving additive, fructooligosaccharides, and at least one other carbohydrate;
217. at least one sweet taste improving additive, kestose, and at least one other carbohydrate;
218. at least one sweet taste improving additive, nystose, and at least one other carbohydrate;
219. at least one sweet taste improving additive, maltotetraol, and at least one other carbohydrate;
220. at least one sweet taste improving additive, maltotriol, and at least one other carbohydrate;
221. at least one sweet taste improving additive, malto-oligosaccharides, and at least one other carbohydrate;
222. at least one sweet taste improving additive, maltotriose, and at least one other carbohydrate;
223. at least one sweet taste improving additive, maltotetraose, and at least one other carbohydrate;
224. at least one sweet taste improving additive, maltopentaose, and at least one other carbohydrate;
225. at least one sweet taste improving additive, maltohexaose, and at least one other carbohydrate;
226. at least one sweet taste improving additive, maltoheptaose, and at least one other carbohydrate;
227. at least one sweet taste improving additive, lactulose, and at least one other carbohydrate;
228. at least one sweet taste improving additive, melibiose, and at least one other carbohydrate;
229. at least one sweet taste improving additive, raffinose, and at least one other carbohydrate;
230. at least one sweet taste improving additive, rhamnose, and at least one other carbohydrate;
231. at least one sweet taste improving additive, ribose, and at least one other carbohydrate;
232. at least one sweet taste improving additive, isomerized liquid sugars, and at least one other carbohydrate;
233. at least one sweet taste improving additive, high fructose corn syrup (e.g. HFCS55, HFCS42, or HFCS90) or starch syrup, and at least one other carbohydrate;
234. at least one sweet taste improving additive, coupling sugars, and at least one other carbohydrate;
235. at least one sweet taste improving additive, soybean oligosaccharides, and at least one other carbohydrate; and
236. at least one sweet taste improving additive, glucose syrup, and at least one other carbohydrate.

In another embodiment, the functional sweetener composition comprises at least one natural and/or synthetic high-potency sweetener and at least one functional ingredient in combination with a plurality of sweet taste improving additives, desirably 3 or more sweet taste improving additives, and even more desirably 4 or more sweet taste improving additives, wherein each sweet taste improving additive is present in an amount such that no one sweet taste improving additive imparts a substantial off taste to the functional sweetener composition. In other words, the amounts of the sweet taste improving additives in the functional sweetener composition are balanced so that no one sweet taste improving additive imparts a substantial off taste to the functional sweetener composition.

According to a particular embodiment of this invention, the functional sweetener composition provided herein comprises at least one sweet taste improving composition in the functional sweetener composition in an amount effective for the functional sweetener composition to impart an osmolarity of at least 10 mOsmoles/L to an aqueous solution of the functional sweetener composition, wherein the at least one natural and/or synthetic high-potency sweetener is present in the aqueous solution in an amount sufficient to impart a maximum sweetness intensity equivalent to that of a 10% aqueous solution of sucrose by weight. As used herein, "mOsmoles/L" refers to milliosmoles per liter. According to another embodiment, the functional sweetener composition comprises at least one sweet taste improving composition in an amount effective for the functional sweetener composition to impart an osmolarity of 10 to 500 mOsmoles/L, preferably 25 to 500 mOsmoles/L preferably, more preferably 100 to 500 mOsmoles/L, more preferably 200 to 500 mOsmoles/L, and still more preferably 300 to 500 mOsmoles/L to an aqueous solution of the functional sweetener composition, wherein the at least one natural and/or synthetic high-potency sweetener is present in the aqueous solution in an amount sufficient to impart a maximum sweetness intensity equivalent to that of a 10% aqueous solution of sucrose by weight. Wherein a plurality of sweet taste improving compositions are combined with at least one natural and/or synthetic high-potency sweetener and at least one functional ingredient, the osmolarity imparted is that of the total combination of the plurality of sweet taste improving compositions.

Osmolarity refers to the measure of osmoles of solute per liter of solution, wherein osmole is equal to the number of moles of osmotically active particles in an ideal solution (e.g., a mole of glucose is one osmole), whereas a mole of sodium chloride is two osmoles (one mole of sodium and one mole of chloride). Thus, in order to improve in the quality of taste of the functional sweetener composition, the osmotically active compounds or the compounds which impart osmolarity must not introduce significant off taste to the formulation.

In one embodiment, suitable sweet taste improving carbohydrate additives for the present invention have a molecular weight less than or equal to 500 and desirably have a molecular weight from 50 to 500. In particular embodiments, suitable carbohydrates with a molecular weight less than or equal to 500 include, but are not limited to, sucrose, fructose, glucose, maltose, lactose, mannose, galactose, and tagatose. Generally, in accordance with desirable embodiments of this invention, a sweet taste improving carbohydrate additive is present in the functional sweetener compositions in an amount from about 1,000 to about 100,000 ppm. (Throughout this specification, the term ppm means parts per million by weight or volume. For example, 500 ppm means 500 mg in a liter.) In accordance with other desirable embodiments of this invention, a sweet taste improving carbohydrate additive is present in the sweetened compositions in an amount from about 2,500 to about 10,000 ppm. In another embodiment, suitable sweet taste improving carbohydrate additives for imparting osmolarities ranging from about 10 mOsmoles/mL to about 500 mOsmoles/L to a sweetenable composition include, but are not limited to, sweet taste improving carbohydrate additives with a molecular weight ranging from about 50 to about 500.

In one embodiment, suitable sweet taste improving polyol additives have a molecular weight less than or equal to 500 and desirably have a molecular weight from 76 to 500. In particular embodiments, suitable sweet taste improving polyol additives with a molecular weight less than or equal to 500 include, but are not limited to, erythritol, glycerol, and propylene glycol. Generally, in accordance with desirable embodiments of this invention, a sweet taste improving polyol additive is present in the functional sweetener compositions in an amount from about 100 ppm to about 80,000 ppm. In accordance with other desirable embodiments of this invention, a sweet taste improving polyol additive is present in sweetened compositions in an amount from about 400 to about 80,000 ppm. In a sub-embodiment, suitable sweet taste improving polyol additives for imparting osmolarities ranging from about 10 mOsmoles/L to about 500 mOsmoles/L to a sweetenable composition include, but are not limited to, sweet taste improving polyol additives with a molecular weight ranging from about 76 to about 500.

In accordance with still other desirable embodiments of this invention, a sweet taste improving polyol additive is present in sweetener compositions in an amount from about 400 to about 80,000 ppm of the total sweetener composition, more particularly from about about 5,000 to about 40,000 ppm, and still more particularly from about 10,000 to about 35,000 ppm. Desirably, the at least one natural and/or synthetic high-potency sweetener and at least one sweet taste improving polyol additive are present in the sweetener composition in a ratio from about 1:4 to about 1:800, respectively; more particularly from about 1:20 to about 1:600; even more particularly from about 1:50 to about 1:300; and still more particularly from about 1:75 to about 1:150.

Generally, in accordance with another embodiment of this invention, a suitable sweet taste improving alcohol additive is present in the functional sweetener compositions in an amount from about 625 to about 10,000 ppm. In another embodiment, suitable sweet taste improving alcohol additives for imparting osmolarities ranging from about 10 mOsmoles/L to about 500 mOsmoles/L to a sweetenable composition include, but are not limited to, sweet taste improving alcohol additives with a molecular weight ranging from about 46 to about 500. A non-limiting example of sweet taste improving alcohol additive with a molecular weight ranging from about 46 to about 500 includes ethanol.

In one embodiment, suitable sweet taste improving amino acid additives have a molecular weight of less than or equal to 250 and desirably have a molecular weight from 75 to 250. In particular embodiments, suitable sweet taste improving amino acid additives with a molecular weight less than or equal to 250 include, but are not limited to, glycine, alanine, serine, valine, leucine, isoleucine, proline, theanine, and threonine. Preferred sweet taste improving amino acid additives include those which are sweet tasting at high concentrations, but desirably are present in embodiments of this invention at amounts below or above their sweetness taste detection threshold. Even more preferred are mixtures of sweet taste improving amino acid additives at amounts below or above their sweetness taste detection threshold. Generally, in accordance with desirable embodiments of this invention, a sweet taste improving amino acid additive is present in the functional sweetener compositions in an amount from about 100 ppm to about 25,000 ppm, more particularly from about 1,000 to about 10,000 ppm, and still more particularly from about 2,500 to about 5,000 ppm. In accordance with other desirable embodiments of this invention, a sweet taste improving amino acid additive is present in the sweetened compositions in an amount from about 250 ppm to about 7,500 ppm. In a sub-embodiment, suitable sweet taste improving amino acid additives for imparting osmolarities ranging from about 10 mOsmoles/L to about 500 mOsmoles/L to a sweetenable composition include, but are not limited to, sweet taste improving amino acid additives with a molecular weight ranging from about 75 to about 250.

Generally, in accordance with yet another embodiment of this invention, a suitable sweet taste improving amino acid salt additive is present in the functional sweetener compositions in an amount from about 25 to about 10,000 ppm, more particularly from about 1,000 to about 7,500 ppm, and still more particularly from about 2,500 to about 5,000 ppm. In another embodiment, suitable sweet taste improving amino acid salt additives for imparting osmolarities ranging from about 10 mOsmoles/L to about 500 mOsmoles/L to a sweetenable composition include, but are not limited to, sweet taste improving amino acid salt additives with a molecular weight ranging from about 75 to about 300. Non-limiting examples of sweet taste improving amino acid salt additives with a molecular weight ranging from about 75 to about 300 include salts of glycine, alanine, serine, theanine, and threonine.

Generally, in accordance with still another embodiment of this invention, a suitable sweet taste improving protein or protein hydroyslate additive is present in the functional sweetener compositions in an amount from about 200 to about 50,000 ppm. In another embodiment, suitable sweet taste improving protein or protein hydrolysate additives for imparting osmolarities ranging from about 10 mOsmoles/L to about 500 mOsmoles/l to a sweetenable composition include, but are not limited to, sweet taste improving protein or protein hydrolysate additives with a molecular weight ranging from about 75 to about 300. Non-limiting examples of sweet taste improving protein or protein hydrolysate additives with a molecular weight ranging from about 75 to about 300 include proteins or protein hydrolysates containing glycine, alanine, serine, and threonine.

Generally, in accordance with another embodiment of this invention, a suitable sweet taste improving inorganic acid additive is present in the functional sweetener compositions in an amount from about 25 to about 5,000 ppm. In another embodiment, suitable sweet taste improving inorganic acid additives for imparting osmolarities ranging from about 10 mOsmoles/L to about 500 mOsmoles/L to a sweetenable composition include, but are not limited to, phosphoric acid, HCl, and $H_2SO_4$ and any other inorganic acid additives which are safe for human or animal consumption when used in a generally acceptable range. In a sub-embodiment, suitable sweet taste improving inorganic acid additives for imparting osmolarities ranging from about 10 mOsmoles/L to about 500 mOsmoles/L to a sweetenable composition include, but are not limited to, sweet taste improving inorganic acid additives with a molecular weight range from about 36 to about 98.

Generally, in accordance with still another embodiment of this invention, a suitable sweet taste improving inorganic acid salt additive is present in the functional sweetener compositions in an amount from about 25 to about 5,000 ppm. In another embodiment, suitable sweet taste improving inorganic acid salt additives for imparting osmolarities ranging from about 10 mOsmoles/L to about 500 mOsmoles/L to a sweetenable composition include, but are not limited to, salts of inorganic acids, for example sodium, potassium, calcium, and magnesium salts of phosphoric acid, and any other alkali or alkaline earth metal salts of other inorganic acids (e.g., sodium bisulfate) which are safe for human or animal consumption when used in a generally acceptable range. In a sub-embodiment, suitable suitable sweet taste improving inorganic acid salt additives for imparting osmolarities ranging from about 10 mOsmoles/L to about 500 mOsmoles/L to a sweetenable composition include, but are not limited to, sweet taste improving inorganic acid salt additives with a molecular weight range from about 58 to about 120.

Generally, in accordance with still another embodiment of this invention, a suitable sweet taste improving organic acid additive is present in the functional sweetener compositions in an amount from about 10 to about 5,000 ppm. In another embodiment, suitable sweet taste improving organic acid additives for imparting osmolarities ranging from about 10 mOsmoles/L to about 500 mOsmoles/L to a sweetenable composition include, but are not limited to, creatine, citric acid, malic acid, succinic acid, hydroxycitric acid, tartaric acid, fumaric acid, gluconic acid, glutaric acid, adipic acid, and any other sweet taste improving organic acid additives which are safe for human or animal consumption when used in a generally acceptable range. In one embodiment, the sweet taste improving organic acid additive comprises a molecular weight range from about 60 to about 208.

Generally, in accordance with still another embodiment of this invention, a suitable sweet taste improving organic acid salt additive is present in the functional sweetener compositions in an amount from about 20 to about 10,000 ppm. In another embodiment, suitable sweet taste improving organic acid salt additives for imparting osmolarities ranging from about 10 mOsmoles/L to about 500 mOsmoles/L to a sweetenable composition include, but are not limited to, salts of sweet taste improving organic acid additives, such as sodium, potassium, calcium, magnesium, and other alkali or alkaline metal salts of citric acid, malic acid, tartaric acid, fumaric acid, gluconic acid, glutaric acid, adipic acid, hydroxycitric acid, succinic acid, and salts of any other sweet taste improving organic acid additives which are safe for human or animal consumption when used in a generally acceptable range. In one embodiment, the sweet taste improving organic acid salt additive comprises a molecular weight range from about 140 to about 208.

Generally, in accordance with yet another embodiment of this invention, a suitable sweet taste improving organic base salt additive is present in the functional sweetener compositions in an amount from about 10 to about 5,000 ppm. In another embodiment, suitable sweet taste improving organic base salt additives for imparting osmolarities ranging from about 10 mOsmoles/L to about 500 mOsmoles/L to a sweetenable composition include, but are not limited to, inorganic and organic acid salts of organic bases such as glucosamine salts, choline salts, and guanidine salts.

Generally, in accordance with yet another embodiment of this invention, a suitable sweet taste improving astringent additive is present in the functional sweetener compositions in an amount from about 25 to about 1,000 ppm. In another embodiment, suitable sweet taste improving astringent additives for imparting osmolarities ranging from about 10 mOsmoles/L to about 500 mOsmoles/L to a sweetenable composition include, but are not limited to, tannic acid, tea polyphenols, catechins, aluminum sulfate, $AlNa(SO_4)_2$, $AlK(SO_4)_2$ and other forms of alum.

Generally, in accordance with yet another embodiment of this invention, a suitable sweet taste improving nucleotide additive is present in the functional sweetener compositions in an amount from about 5 to about 1,000 ppm. In another embodiment, suitable sweet taste improving nucleotide additives for imparting osmolarities ranging from about 10 mOsmoles/L to about 500 mOsmoles/L to a sweetenable composition include, but are not limited to, adenosine monophosphate.

Generally, in accordance with yet another embodiment of this invention, a suitable sweet taste improving polyamino acid additive is present in the functional sweetener compositions in an amount from about 30 to about 2,000 ppm. In another embodiment, suitable sweet taste improving polyamino acid additives for imparting osmolarities ranging from about 10 mOsmoles/L to about 500 mOsmoles/L to a sweetenable composition include, but are not limited to, poly-L-lysine (e.g., poly-L-α-lysine or poly-L-ε-lysine), poly-L-ornithine (e.g., poly-L-α-ornithine or poly-L-ε-ornithine), and poly-L-arginine.

Generally, in accordance with yet another embodiment of this invention, a suitable sweet taste improving polymer additive is present in the functional sweetener compositions in an amount from about 30 to about 2,000 ppm. In another embodiment, suitable sweet taste improving polymer additives for imparting osmolarities ranging from about 10 mOsmoles/L to about 500 mOsmoles/L to a sweetenable composition include, but are not limited to, chitosan, sodium hexametaphosphate and its salts, pectin, hydrocolloids such as gum acacia senegal, propylene glycol, polyethylene glycol, and poly(ethylene glycol methyl ether).

Generally, in accordance with yet another embodiment of this invention, a suitable sweet taste improving surfactant additive is present in the functional sweetener compositions in an amount from about 1 to about 5,000 ppm. In another embodiment, suitable sweet taste improving surfactant additives for imparting osmolarities ranging from about 10 mOsmoles/L to about 500 mOsmoles/L to a sweetenable composition include, but are not limited to, polysorbates, choline chloride, sodium taurocholate, lecithins, sucrose oleate esters, sucrose stearate esters, sucrose palmitate esters, and sucrlose laurate esters.

Generally, in accordance with yet another embodiment of this invention, a suitable sweet taste improving flavonoid additive is present in the functional sweetener compositions in an amount from about 0.1 to about 1,000 ppm. In another embodiment, suitable sweet taste improving flavonoid additives for imparting osmolarities ranging from about 10 mOsmoles/L to about 500 mOsmoles/L to a sweetenable composition include, but are not limited to, naringin, catechins, rutins, neohesperidin, and neohesperidin dihydrochalcone.

In a preferred embodiment, non-limiting examples of sweet taste improving compositions enhancing the natural and/or synthetic high-potency sweetener's osmotic taste to be more sugar-like include sweet taste improving carbohydrate additives, sweet taste improving alcohol additives, sweet taste improving polyol additives, sweet taste improving amino acid additives, sweet taste improving amino acid salt additives, sweet taste improving inorganic acid salt additives, sweet taste improving polymer additives, and sweet taste improving protein or protein hydrolysate additives.

In another embodiment, suitable sweet taste improving carbohydrate additives for improving the osmotic taste of the natural and/or synthetic high-potency sweetener to be more sugar-like include, but are not limited to, sweet taste improving carbohydrate additives with a molecular weight ranging from about 50 to about 500. Non-limiting examples of sweet taste improving carbohydrate additives with a molecular weight ranging from about 50 to about 500 include sucrose, fructose, glucose, maltose, lactose, mannose, galactose, ribose, rhamnose, trehalose, HFCS, and tagatose.

In another embodiment, suitable sweet taste improving polyol additives for improving the osmotic taste of natural and/or synthetic high-potency sweetener to be more sugar-like include, but are not limited to, sweet taste improving polyol additives with a molecular weight ranging from about 76 to about 500. Non-limiting examples of sweet taste improving polyol additives with a molecular weight ranging from about 76 to about 500 include erythritol, glycerol, and propylene glycol. In a sub-embodiment, other suitable sweet taste improving polyol additives include sugar alcohols.

In another embodiment, suitable sweet taste improving alcohol additives for improving the osmotic taste of natural and/or synthetic high-potency sweetener to be more sugar-like include, but are not limited to, sweet taste improving alcohol additives with a molecular weight ranging from about 46 to about 500. A non-limiting example of sweet taste improving alcohol additive with a molecular weight ranging from about 46 to about 500 includes ethanol.

In another embodiment, suitable sweet taste improving amino acid additives for improving the osmotic taste of natural and/or synthetic high-potency sweetener to be more sugar-like include, but are not limited to, sweet taste improving amino acid additives with a molecular weight ranging from about 75 to about 250. Non-limiting examples of sweet taste improving amino acid additives with a molecular weight ranging from about 75 to about 250 include glycine, alanine, serine, leucine, valine, isoleucine, proline, hydroxyproline, glutamine, theanine, and threonine.

In another embodiment, suitable sweet taste improving amino acid salt additives for improving the osmotic taste of natural and/or synthetic high-potency sweetener to be more sugar-like include, but are not limited to, sweet taste improving amino acid salt additives with a molecular weight ranging from about 75 to about 300. Non-limiting examples of sweet taste improving amino acid salt additives with a molecular weight ranging from about 75 to about 300 include salts of glycine, alanine, serine, leucine, valine, isoleucine, proline, hydroxyproline, glutamine, theanine, and threonine.

In another embodiment, suitable sweet taste improving protein or protein hydrolysate additives for improving the osmotic taste of natural and/or synthetic high-potency sweetener to be more sugar-like include, but are not limited to, sweet taste improving protein or protein hydrolysate additives with a molecular weight ranging from about 75 to about 300. Non-limiting examples of sweet taste improving protein or protein hydrolysate additives with a molecular weight ranging from about 75 to about 300 include protein or protein hydrolysates containing glycine, alanine, serine, leucine, valine, isoleucine, proline, and threonine.

In another embodiment, suitable sweet taste improving inorganic acid salt additives for improving the osmotic taste of natural and/or synthetic high-potency sweetener to be more sugar-like include, but are not limited to, sodium chloride, potassium chloride, magnesium chloride, $KH_2PO_4$ and $NaH_2PO_4$. Suitable sweet taste improving inorganic acid salt additives for improving the osmotic taste may comprise a molecular weight from about 58 to about 120.

In another embodiment, suitable sweet taste improving bitter additives for improving the osmotic taste of the natural and/or synthetic high-potency sweetener to be more sugar-like include, but are not limited to, caffeine, quinine, urea, quassia, tannic acid, and naringin.

In one embodiment, a functional sweetener composition is provided comprising at least one functional ingredient and at least one natural and/or synthetic high-potency sweetener in combination with at least one sweet taste improving nucleotide additive chosen from inosine monophosphate ("IMP"), guanosine monophosphate ("GMP"), adenosine monophosphate ("AMP"), cytosine monophosphate (CMP), uracil monophosphate (UMP), inosine diphosphate, guanosine diphosphate, adenosine diphosphate, cytosine diphosphate, uracil diphosphate, inosine triphosphate, guanosine triphosphate, adenosine triphosphate, cytosine triphosphate, uracil triphosphate, nucleosides thereof, nucleic acid bases thereof, or salts thereof.

In one embodiment, a functional sweetener composition is provided comprising at least one functional ingredient and at least one natural and/or synthetic high-potency sweetener in combination with at least one sweet taste improving carbohydrate additive chosen from tagatose, trehalose, galactose, rhamnose, cyclodextrin (e.g., α-cyclodextrin, β-cyclodextrin, and γ-cyclodextrin), maltodextrin (including resistant maltodextrins such as Fibersol-2™), dextran, sucrose, glucose, ribulose, fructose, threose, arabinose, xylose, lyxose, allose, altrose, mannose, idose, lactose, maltose, invert sugar, isotrehalose, neotrehalose, palatinose or isomaltulose, erythrose, deoxyribose, gulose, idose, talose, erythrulose, xylulose, psicose, turanose, cellobiose, amylopectin, glucosamine, mannosamine, fucose, glucuronic acid, gluconic acid, glucono-lactone, abequose, galactosamine, beet oligosaccharides, isomalto-oligosaccharides (isomaltose, isomaltotriose, panose and the like), xylo-oligosaccharides (xylotriose, xylobiose and the like), gentio-oligoscaccharides (gentiobiose, gentiotriose, gentiotetraose and the like), sorbose, nigero-oligosaccharides, palatinose oligosaccharides, fucose, fructooligosaccharides (kestose, nystose and the like), maltotetraol, maltotriol, malto-oligosaccharides (maltotriose, maltotetraose, maltopentaose, maltohexaose, maltoheptaose and the like), lactulose, melibiose, raffinose, rhamnose, ribose, isomerized liquid sugars such as high fructose corn/starch syrup (e.g., HFCS55, HFCS42, or HFCS90), coupling sugars, soybean oligosaccharides, or glucose syrup.

In another embodiment, a functional sweetener composition is provided comprising at least one functional ingredient and at least one natural and/or synthetic high-potency sweetener in combination with at least one sweet taste improving polyol additive chosen from erythritol, maltitol, mannitol, sorbitol, lactitol, xylitol, inositol, isomalt, propylene glycol, glycerol (glycerine), threitol, galactitol, palatinose, reduced isomalto-oligosaccharides, reduced xylo-oligosaccharides, reduced gentio-oligosaccharides, reduced maltose syrup, or reduced glucose syrup.

In another embodiment, a functional sweetener composition is provided comprising at least one functional ingredient and at least one natural and/or synthetic high-potency sweetener in combination with at least one sweet taste improving amino acid additive chosen from aspartic acid, arginine, glycine, glutamic acid, proline, threonine, theanine, cysteine, cystine, alanine, valine, tyrosine, leucine, isoleucine, asparagine, serine, lysine, histidine, ornithine, methionine, camitine, aminobutyric acid (alpha-, beta-, and gamma-isomers), glutamine, hydroxyproline, taurine, norvaline, sarcosine, or salts thereof.

In another embodiment, a functional sweetener composition is provided comprising at least one functional ingredient and at least one natural and/or synthetic high-potency sweetener in combination with at least one sweet taste improving polyamino acid additive chosen from poly-L-aspartic acid, poly-L-lysine (e.g., poly-L-α-lysine or poly-L-ϵ-lysine), poly-L-ornithine (e.g., poly-L-α-ornithine or poly-L-ϵ-ornithine), poly-L-arginine, other polymeric forms of amino acids, or salts thereof.

In another embodiment, a functional sweetener composition is provided comprising at least one functional ingredient and at least one natural and/or synthetic high-potency sweetener in combination with at least one sweet taste improving sugar acid additive chosen from aldonic, uronic, aldaric, alginic, gluconic, glucuronic, glucaric, galactaric, galacturonic, or salts thereof.

In another embodiment, a functional sweetener composition is provided comprising at least one functional ingredient and at least one natural and/or synthetic high-potency sweetener in combination with at least one sweet taste improving organic acid additive chosen from C2-C30 carboxylic acids, substituted hydroxyl C1-C30 carboxylic acids, benzoic acid, substituted benzoic acids (e.g., 2,4-dihydroxybenzoic acid), substituted cinnamic acids, hydroxyacids, substituted hydroxybenzoic acids, substituted cyclohexyl carboxylic acids, tannic acid, lactic acid, tartaric acid, citric acid, gluconic acid, glucoheptonic acids, glutaric acid, creatine, adipic acid, hydroxycitric acid, malic acid, fruitaric acid, fumaric acid, maleic acid, succinic acid, chlorogenic acid, salicylic acid, caffeic acid, bile acids, acetic acid, ascorbic acid, alginic acid, erythorbic acid, polyglutamic acid, or salts thereof.

In another embodiment, a functional sweetener composition is provided comprising at least one functional ingredient and at least one natural and/or synthetic high-potency sweetener in combination with at least one sweet taste improving inorganic acid additive chosen from phosphoric acid, phosphorous acid, polyphosphoric acid, hydrochloric acid, sulfuric acid, carbonic acid, sodium dihydrogen phosphate, or salts thereof.

In another embodiment, a functional sweetener composition is provided comprising at least one functional ingredient and at least one natural and/or synthetic high-potency sweetener in combination with at least one sweet taste improving bitter compound additive chosen from caffeine, quinine, urea, bitter orange oil, naringin, quassia, or salts thereof.

In another embodiment, a functional sweetener composition is provided comprising at least one functional ingredient and at least one natural and/or synthetic high-potency sweetener in combination with at least one sweet taste improving flavorant additive chosen from vanillin, vanilla extract, mango extract, cinnamon, citrus, coconut, ginger, viridiflorol, almond, menthol, grape skin extract, or grape seed extract. In another particular embodiment, the at least one sweet taste improving flavorant additive comprises a proprietary sweetener chosen from Döhler™ Natural Flavoring Sweetness Enhancer K14323 (Döhler™, Darmstadt, Germany), Symrise™ Natural Flavor Mask for Sweeteners 161453 or 164126 (Symrise™, Iolzminden, Germany), Natural Advantage™ Bitterness Blockers 1, 2, 9 or 10 (Natural Advantage™, Freehold, N.J., U.S.A.), or Sucramask™ (Creative Research Management, Stockton, Calif., U.S.A.)

In another embodiment, a functional sweetener composition is provided comprising at least one functional ingredient and at least one natural and/or synthetic high-potency sweetener in combination with at least one sweet taste improving polymer additive chosen from chitosan, pectin, pectic, pectinic, polyuronic, polygalacturonic acid, starch, food hydrocolloid or crude extracts thereof (e.g., gum acacia senegal, gum acacia seyal, carageenan), poly-L-lysine (e.g., poly-L-α-lysine or poly-L-β-lysine), poly-L-ornithine (e.g., poly-L-α-ornithine or poly-L-ε-ornithine), polypropylene glycol, polyethylene glycol, poly(ethylene glycol methyl ether), polyarginine, polyaspartic acid, polyglutamic acid, polyethyleneimine, alginic acid, sodium alginate, propylene glycol alginate, sodium polyethyleneglycolalginate, sodium hexametaphosphate and its salts, or other cationic and anionic polymers.

In another embodiment, a functional sweetener composition is provided comprising at least one functional ingredient and at least one natural and/or synthetic high-potency sweetener in combination with at least one sweet taste improving protein hydrolysate additive chosen from bovine serum albumin (BSA), whey protein (including fractions or concentrates thereof such as 90% instant whey protein isolate, 34% whey protein, 50% hydrolyzed whey protein, and 80% whey protein concentrate), soluble rice protein, soy protein, protein isolates, protein hydrolysates, reaction products of protein hydrolysates, glycoproteins, and/or proteoglycans containing amino acids (e.g., glycine, alanine, serine, threonine, theanine, asparagine, glutamine, arginine, valine, isoleucine, leucine, norvaline, methionine, proline, tyrosine, hydroxyproline, or the like).

In another embodiment, a functional sweetener composition is provided comprising at least one functional ingredient and at least one natural and/or synthetic high-potency sweetener in combination with at least one sweet taste improving surfactant additive chosen from polysorbates (e.g., polyoxyethylene sorbitan monooleate (polysorbate 80), polysorbate 20, polysorbate 60), sodium dodecylbenzenesulfonate, dioctyl sulfosuccinate or dioctyl sulfosuccinate sodium, sodium dodecyl sulfate, cetylpyridinium chloride, hexadecyltrimethylammonium bromide, sodium cholate, carbamoyl, choline chloride, sodium glycocholate, sodium taurocholate, sodium taurodeoxycholate, lauric arginate, sodium stearoyl lactylate, lecithins, sucrose oleate esters, sucrose stearate esters, sucrose palmitate esters, sucrose laurate esters, and other emulsifiers, or the like.

In another embodiment, a functional sweetener composition is provided comprising at least one functional ingredient and at least one natural and/or synthetic high-potency sweetener in combination with at least one sweet taste improving flavonoid additive chosen from catechins, polyphenols, rutins, neohesperidin, naringin, neohesperidin dihydrochalcone, or the like.

In another embodiment, a functional sweetener composition is provided comprising at least one functional ingredient and at least one natural and/or synthetic high-potency sweetener in combination with ethanol.

In another embodiment, a functional sweetener composition is provided comprising at least one functional ingredient and at least one natural and/or synthetic high-potency sweetener in combination with at least one sweet taste improving astringent compound additive chosen from tannic acid, europium chloride ($EuCl_3$), gadolinium chloride ($GdCl_3$), terbium chloride ($TbCl_3$), alum, tannic acid, and polyphenols (e.g., tea polyphenol), In another embodiment, a functional sweetener composition is provided comprising at least one functional ingredient and at least one natural and/or synthetic high-potency sweetener in combination with at least one sweet taste improving inorganic salt additive chosen from sodium chloride, potassium chloride, sodium dihydrogen phosphate, sodium sulfate, potassium citrate, europium chloride ($EuCl_3$), gadolinium chloride ($GdCl_3$), terbium chloride ($TbCl_3$), magnesium sulfate, magnesium phosphate, alum, magnesium chloride, mono-, di-, tri-basic sodium or potassium salts of phosphoric acid, salts of hydrochloric acid, sodium carbonate, sodium bisulfate, or sodium bicarbonate.

In another embodiment, a functional sweetener composition is provided comprising at least one functional ingredient and at least one natural and/or synthetic high-potency sweetener in combination with at least one sweet taste improving organic salt additive chosen from choline chloride, gluconic acid sodium salt, gluconic acid potassium salt, guanidine MCl, amiloride HCl, glucosamine HCl, monosodium glutamate (MSC), adenosine monophosphate salt, magnesium gluconate, potassium tartrate, and sodium tartrate.

In another embodiment, a functional sweetener composition is provided comprising at least one functional ingredient and at least one natural and/or synthetic high-potency sweetener in combination with at least one sweet taste improving nucleotide additive, at least one sweet taste improving carbohydrate additive, and at least one sweet taste improving amino acid additive; wherein the at least one nucleotide additive is chosen from inosine monophosphate ("IMP"), guanosine monophosphate ("GMP"), adenosine monophosphate ("AMP"), cytosine monophosphate (CMP), uracil monophosphate (UMP), inosine diphosphate, guanosine diphosphate, adenosine diphosphate, cytosine diphosphate, uracil diphosphate, inosine triphosphate, guanosine triphosphate, adenosine triphosphate, cytosine triphosphate, uracil triphosphate, nucleosides thereof, nucleic acid bases thereof; or salts thereof; wherein the at least one carbohydrate additive is chosen from tagatose, trehalose, galactose, rhamnose, cyclodextrin (e.g., α-cyclodextrin, β-cyclodextrin, and γ-cyclodextrin), maltodextrin (including resistant maltodextrins such as Fibersol-2™), dextran, sucrose, glucose, ribulose, fructose, threose, arabinose, xylose, lyxose, allose, altrose, mannose, idose, lactose, maltose, invert sugar, isotrehalose, neotrehalose, palatinose or isomaltulose, erythrose, deoxyribose, gulose, idose, talose, erythrulose, xylulose, psicose, turanose, cellobiose, amylopectin, glucosamine, mannosamine, fucose, glucuronic acid, gluconic acid, glucono-lactone, abequose, galactosamine, beet oligosaccharides, isomalto-oligosaccharides (isomaltose, isomaltotriose, panose and the like), xylo-oligosaccharides (xylotriose, xylobiose and the like), gentio-oligosaccharides (gentiobiose, gentiotriose, gentiotetraose and the like), sorbose, nigero-oligosaccharides, palatinose oligosaccharides, fucose, fructooligosaccharides (kestose, nystose and the like), maltotetraol, maltotriol, malto-oligosaccharides (maltotriose, maltotetraose, maltopentaose, maltohexaose, maltoheptaose and the like), lactulose, melibiose, raffinose, rhamnose, ribose, isomerized liquid sugars such as high fructose corn/starch syrup (e.g., HFCS55, UFCS42, or HFCS90), coupling sugars, soybean oligosaccharides, or glucose syrup; and wherein the at least one amino acid additive is chosen from aspartic acid, arginine, glycine, glutamic acid, proline, threonine, theanine, cysteine, cystine, alanine, valine, tyrosine, leucine, isoleucine, asparagine, serine, lysine, histidine, ornithine, methionine, carnitine, aminobutyric acid (alpha-, beta-, and gamma-isomers), glutamine, hydroxyproline, taurine, norvaline, sarcosine, or salts thereof.

In another embodiment, a functional sweetener composition is provided comprising at least one functional ingredient and at least one natural and/or synthetic high-potency sweetener in combination with at least one sweet taste improving nucleotide additive and at least one sweet taste improving carbohydrate additive; wherein the at least one nucleotide additive is chosen from inosine monophosphate ("IMP"), guanosine monophosphate ("GMP"), adenosine monophosphate ("AMP"), cytosine monophosphate (CMP), uracil monophosphate (UMP), inosine diphosphate, guanosine diphosphate, adenosine diphosphate, cytosine diphosphate, uracil diphosphate, inosine triphosphate, guanosine triphosphate, adenosine triphosphate, cytosine triphosphate, uracil triphosphate, nucleosides thereof, nucleic acid bases thereof, or salts thereof; and wherein the at least one carbohydrate additive is chosen from tagatose, trehalose, galactose, rhamnose, cyclodextrin (e.g., α-cyclodextrin, β-cyclodextrin, and γ-cyclodextrin), maltodextrin (including resistant maltodextrins such as Fibersol-2™), dextran, sucrose, glucose, ribulose, fructose, threose, arabinose, xylose, lyxose, allose, altrose, mannose, idose, lactose, maltose, invert sugar, isotrehalose, neotrehalose, palatinose or isomaltulose, erythrose, deoxyribose, gulose, idose, talose, erythrulose, xylulose, psicose, turanose, cellobiose, amylopectin, glucosamine, mannosamine, fucose, glucuronic acid, gluconic acid, glucono-lactone, abequose, galactosamine, beet oligosaccharides, isomalto-oligosaccharides (isomaltose, isomaltotriose, panose and the like), xylo-oligosaccharides (xylotriose, xylobiose and the like), gentio-oligosaccharides (gentiobiose, gentiotriose, genetiotetraose and the like), sorbose, nigero-oligosaccharides, palatinose oligosaccharides, fucose, fructooligosaccharides (kestose, nystose and the like), maltotetraol, maltotriol, malto-oligosaccharides (maltotriose, maltotetraose, maltopentaose, maltohexaose, maltoheptaose and the like), lactulose, melibiose, raffinose, rhamnose, ribose, isomerized liquid sugars such as high fructose corn/starch syrup (e.g., HFCS55, HFCS42, or HFCS90), coupling sugars, soybean oligosaccharides, or glucose syrup.

In another embodiment, a functional sweetener composition is provided comprising at least one functional ingredient and at least one natural and/or synthetic high-potency sweetener in combination with at least one sweet taste improving nucleotide additive and at least one sweet taste improving polyol additive; wherein the at least one nucleotide additive is chosen from inosine monophosphate ("IMP"), guanosine monophosphate ("GMP"), adenosine monophosphate ("AMP"), cytosine monophosphate (CMP), uracil monophosphate (UMP), inosine diphosphate, guanosine diphosphate, adenosine diphosphate, cytosine diphosphate, uracil diphosphate, inosine triphosphate, guanosine triphosphate, adenosine triphosphate, cytosine triphosphate, uracil triphosphate, nucleosides thereof, nucleic acid bases thereof, or salts thereof; and wherein the at least one polyol additive is chosen from erythritol, maltitol, mannitol, sorbitol, lactitol, xylitol, inositol, isomalt, propylene glycol, glycerol (glycerine), threitol, galactitol, palatinose, reduced isomalto-oligosaccharides, reduced xylo-oligosaccharides, reduced gentio-oligosaccharides, reduced maltose syrup, or reduced glucose syrup.

In another embodiment, a functional sweetener composition is provided comprising at least one functional ingredient and at least one natural and/or synthetic high-potency sweetener in combination with at least one sweet taste improving nucleotide additive and at least one sweet taste improving amino acid; wherein the at least one nucleotide additive is chosen from inosine monophosphate ("IMP"), guanosine monophosphate ("GMP"), adenosine monophosphate ("AMP"), cytosine monophosphate (CMP), uracil monophosphate (UMP), inosine diphosphate, guanosine diphosphate, adenosine diphosphate, cytosine diphosphate, uracil diphosphate, inosine triphosphate, guanosine triphosphate, adenosine triphosphate, cytosine triphosphate, uracil triphosphate, nucleosides thereof, nucleic acid bases thereof, or salts thereof; and wherein the at least one amino acid additive is chosen from aspartic acid, arginine, glycine, glutamic acid, proline, threonine, theanine, cysteine, cystine, alanine, valine, tyrosine, leucine, isoleucine, asparagine, serine, lysine, histidine, ornithine, methionine, carnitine, aminobutyric acid (alpha-, beta-, and gamma-isomers), glutamine, hydroxyproline, taurine, norvaline, sarcosine, or salts thereof.

In another embodiment, a functional sweetener composition is provided comprising at least one functional ingredient and at least one natural and/or synthetic high-potency sweetener in combination with at least one sweet taste improving carbohydrate additive, at least one sweet taste improving polyol additive, and at least one sweet taste improving amino acid additive; wherein the at least one carbohydrate additive is chosen from tagatose, trehalose, galactose, rhamnose, cyclodextrin (e.g., α-cyclodextrin, β-cyclodextrin, and γ-cyclodextrin), maltodextrin (including resistant maltodextrins such as Fibersol-2 μm), dextran, sucrose, glucose, ribulose, fructose, threose, arabinose, xylose, lyxose, allose, altrose, mannose, idose, lactose, maltose, invert sugar, isotrehalose, neotrehalose, palatinose or isomaltulose, erythrose, deoxyribose, gulose, idose, talose, erythrulose, xylulose, psicose, turanose, cellobiose, amylopectin, glucosamine, mannosamine, fucose, glucuronic acid, gluconic acid, glucono-lactone, abequose, galactosamine, beet oligosaccharides, isomalto-oligosaccharides (isomaltose, isomaltotriose, panose and the like), xylo-oligosaccharides (xylotriose, xylobiose and the like), gentio-oligoscaccharides (gentiobiose, gentiotriose, gentiotetraose and the like), sorbose, nigero-oligosaccharides, palatinose oligosaccharides, fucose, fructooligosaccharides (kestose, nystose and the like), maltotetraol, maltotriol, malto-oligosaccharides (maltotriose, maltotetraose, maltopentaose, maltohexaose, maltoheptaose and the like), lactulose, melibiose, raffinose, rhamnose, ribose, isomerized liquid sugars such as high fructose corn/starch syrup (e.g., HFCS55, HFCS42, or HFCS90), coupling sugars, soybean oligosaccharides, or glucose syrup; wherein the at least one polyol additive is chosen from erythritol, maltitol, mannitol, sorbitol, lactitol, xylitol, inositol, isomalt, propylene glycol, glycerol (glycerine), threitol, galactitol, palatinose, reduced isomalto-oligosaccharides, reduced xylo-oligosaccharides, reduced gentio-oligosaccharides, reduced maltose syrup, or reduced glucose syrup; and wherein the at least one amino acid additive is chosen from aspartic acid, arginine, glycine, glutamic acid, proline, threonine, theanine, cysteine, cystine, alanine, valine, tyrosine, leucine, isoleucine, asparagine, serine, lysine, histidine, ornithine, methionine, carnitine, aminobutyric acid (alpha-, beta-, and gamma-isomers), glutamine, hydroxyproline, taurine, norvaline, sarcosine, or salts thereof.

In another embodiment, a functional sweetener composition is provided comprising at least one functional ingredient and at least one natural and/or synthetic high-potency sweetener in combination with at least one sweet taste improving carbohydrate additive and at least one sweet taste improving polyol additive; wherein the at least one carbohydrate additive is chosen from tagatose, trehalose, galactose, rhamnose, cyclodextrin (e.g., α-cyclodextrin, β-cyclodextrin, and γ-cyclodextrin), maltodextrin (including resistant maltodextrins such as Fibersol-2™), dextran, sucrose, glucose, ribulose, fructose, threose, arabinose, xylose, lyxose, allose, altrose, mannose, idose, lactose, maltose, invert sugar, isotrehalose, neotrehalose, palatinose or isomaltulose, erythrose, deoxyribose, gulose, idose, talose, erythrulose, xylulose, psicose, turanose, cellobiose, amylopectin, glucosamine, mannosamine, fucose, glucuronic acid, gluconic acid, gluconolactone, abequose, galactosamine, beet oligosaccharides, isomalto-oligosaccharides (isomaltose, isomaltotriose, panose and the like), xylo-oligosaccharides (xylotriose, xylobiose and the like), gentio-oligoscaccharides (gentiobiose, gentiotriose, gentiotetraose and the like), sorbose, migero-oligosaccharides, palatinose oligosaccharides, fucose, fructooligosaccharides (kestose, nystose and the like), maltotetraol, maltotriol, malto-oligosaccharides (maltotriose, maltotetraose, maltopentaose, maltohexaose, maltoheptaose and the like), lactulose, melibiose, raffinose, rhamnose, ribose, isomerized liquid sugars such as high fructose corn/starch syrup (e.g., HFCS55, HFCS42, or HFCS90), coupling sugars, soybean oligosaccharides, or glucose syrup; and wherein the at least one polyol additive is chosen from erythritol, maltitol, mannitol, sorbitol, lactitol, xylitol, inositol, isomalt, propylene glycol, glycerol (glycerine), threitol, galactitol, palatinose, reduced isomalto-oligosaccharides, reduced xylo-oligosaccharides, reduced gentio-oligosaccharides, reduced maltose syrup, or reduced glucose syrup.

In another embodiment, a functional sweetener composition is provided comprising at least one functional ingredient and at least one natural and/or synthetic high-potency sweetener in combination with at least one sweet taste improving carbohydrate additive and at least one sweet taste improving amino acid additive; wherein the at least one carbohydrate additive is chosen from tagatose, trehalose, galactose, rhamnose, cyclodextrin (e.g., α-cyclodextrin, β-cyclodextrin, and γ-cyclodextrin), maltodextrin (including resistant maltodextrins such as Fibersol-2™), dextran, sucrose, glucose, ribulose, fructose, threose, arabinose, xylose, lyose, allose, altrose, mannose, idose, lactose, maltose, invert sugar, isotrehalose, neotrehalose, palatinose or isomaltulose, erythrose, deoxyribose, gulose, idose, talose, erythrulose, xylulose, psicose, turanose, cellobiose, amylopectin, glucosamine, mannosamine, fucose, glucuronic acid, gluconic acid, gluconolactone, abequose, galactosamine, beet oligosaccharides, isomalto-oligosaccharides (isomaltose, isomaltotriose, panose and the like), xylo-oligosaccharides (xylotriose, xylobiose and the like), gentio-oligoscaccharides (gentiobiose, gentiotriose, gentiotetraose and the like), sorbose, nigero-oligosaccharides, palatinose oligosaccharides, fucose, fructooligosaccharides (kestose, nystose and the like), maltotetraol, maltotriol, malto-oligosaccharides (maltotriose, maltotetraose, maltopentaose, maltohexaose, maltoheptaose and the like), lactulose, melibiose, raffinose, rhamnose, ribose, isomerized liquid sugars such as high fructose corn/starch syrup (e.g., HFCS55, HFCS42, or HFCS90), coupling sugars, soybean oligosaccharides, or glucose syrup; and wherein the at least one amino acid additive is chosen from aspartic acid, arginine, glycine, glutamic acid, proline, threonine, theanine, cysteine, cystine, alanine, valine, tyrosine, leucine, isoleucine, asparagine, serine, lysine, histidine, ornithine, methionine, carnitine, aminobutyric acid (alpha-, beta-, and gamma-isomers), glutamine, hydroxyproline, taurine, norvaline, sarcosine, or salts thereof.

In another embodiment, a functional sweetener composition is provided comprising at least one functional ingredient and at least one natural and/or synthetic high-potency sweetener in combination with at least one sweet taste improving polyol additive and at least one sweet taste improving amino acid additive; wherein the at least one polyol additive is chosen from erythritol, maltitol, mannitol, sorbitol, lactitol, xylitol, inositol, isomalt, propylene glycol, glycerol (glycerin), threitol, galactitol, palatinose, reduced isomalto-oligosaccharides, reduced xylo-oligosaccharides, reduced gentio-oligosaccharides, reduced maltose syrup, or reduced glucose syrup; and wherein the at least one amino acid additive is chosen from aspartic acid, arginine, glycine, glutamic acid, proline, threonine, theanine, cysteine, cystine, alanine, valine, tyrosine, leucine, isoleucine, asparagine, serine, lysine, histidine, ornithine, methionine, carnitine, aminobutyric acid (alpha-, beta-, and gamma-isomers), glutamine, hydroxyproline, taurine, norvaline, sarcosine, or salts thereof.

In another embodiment, a functional sweetener composition is provided comprising at least one functional ingredient and at least one natural and/or synthetic high-potency sweetener in combination with at least one sweet taste improving polyol additive and at least one sweet taste improving inorganic salt additive; wherein the at least one polyol additive is chosen from erythritol, maltitol, mannitol, sorbitol, lactitol, xylitol, inositol, isomalt, propylene glycol, glycerol (glycerin), threitol, galactitol, palatinose, reduced isomalto-oligosaccharides, reduced xylo-oligosaccharides, reduced gentio-oligosaccharides, reduced maltose syrup, or reduced glucose syrup; and wherein the at least one inorganic salt additive is chosen from sodium chloride, potassium chloride, sodium dihydrogen phosphate, sodium sulfate, potassium citrate, europium chloride (EuCl$_3$), gadolinium chloride (GdCl$_3$), terbium chloride (TbCl$_3$), magnesium sulfate, alum, magnesium chloride, potassium chloride, mono-, di-, tri-basic sodium or potassium salts of phosphoric acid, salts of hydrochloric acid, sodium carbonate, sodium bisulfate, or sodium bicarbonate.

In another embodiment, a functional sweetener composition is provided comprising at least one functional ingredient and at least one natural and/or synthetic high-potency sweetener in combination with at least one sweet taste improving carbohydrate additive and at least one sweet taste improving inorganic salt additive; wherein the at least one carbohydrate additive is chosen from tagatose, trehalose, galactose, rhamnose, cyclodextrin (e.g., α-cyclodextrin, β-cyclodextrin, and γ-cyclodextrin), maltodextrin (including resistant maltodextrins such as Fibersol-2™), dextran, sucrose, glucose, ribulose, fructose, threose, arabinose, xylose, lyxose, allose, altrose, mannose, idose, lactose, maltose, invert sugar, isotrehalose, neotrehalose, palatinose or isomaltulose, erythrose, deoxyribose, gulose, idose, talose, erythrulose, xylulose, psicose, turanose, cellobiose, amylopectin, glucosamine, cmannosamine, fucose, glucuronic acid, gluconic acid, gluconolactone, abequose, galactosamine, beet oligosaccharides, isomalto-oligosaccharides (isomaltose, isomaltotriose, panose and the like), xylo-oligosaccharides (xylotriose, xylobiose and the like), gentio-oligoscaccharides (gentiobiose, gentiotriose, gentiotetraose and the like), sorbose, nigero-oligosaccharides, palatinose oligosaccharides, fucose, fructooligosaccharides (kestose, nystose and the like), maltotetraol, maltotriol, malto-oligosaccharides (maltotriose, maltotetraose, maltopentaose, maltohexaose, maltoheptaose and the like), lactulose, melibiose, raffinose, rhamnose, ribose, isomerized liquid sugars such as high fructose corn/starch syrup (e.g., HFCS55, HFCS42, or HFCS90), coupling sugars, soybean oligosaccharides, or glucose syrup; and wherein the at least one inorganic salt additive is chosen from sodium chloride, potassium chloride, sodium dihydrogen phosphate, sodium sulfate, potassium citrate, europium chloride (EuCl$_3$), gadolinium chloride (GdCl$_3$), terbium chloride (TbCl$_3$), magnesium phosphate, magnesium sulfate, alum, magnesium chloride, potassium chloride, mono-, di-, tri-basic sodium or potassium salts of phosphoric acid, salts of hydrochloric acid, sodium carbonate, sodium bisulfate, or sodium bicarbonate.

In another embodiment, a functional sweetener composition is provided comprising at least one functional ingredient and at least one natural and/or synthetic high-potency sweetener in combination with at least one sweet taste improving carbohydrate additive, at least one sweet taste improving amino acid additive, and at least one sweet taste improving inorganic salt additive; wherein the at least one carbohydrate additive is chosen from tagatose, trehalose, galactose, rhamnose, cyclodextrin (e.g., α-cyclodextrin, β-cyclodextrin, and γ-cyclodextrin), maltodextrin (including resistant maltodextrins such as Fibersol-2™), dextran, sucrose, glucose, ribulose, fructose, threose, arabinose, xylose, lyxose, allose, altrose, mannose, idose, lactose, maltose, invert sugar, isotrehalose, neotrehalose, palatinose or isomaltulose, erythrose, deoxyribose, gulose, idose, talose, erythrulose, xylulose, psicose, turanose, cellobiose, amylopectin, glucosamine, mannosamine, fucose, glucuronic acid, gluconic acid, gluconolactone, abequose, galactosamine, beet oligosaccharides, isomalto-oligosaccharides (isomaltose, isomaltotriose, panose and the like), xylo-oligosaccharides (xylotriose, xylobiose and the like), gentio-oligoscaccharides (gentiobiose, gentiotriose, gentiotetraose and the like), sorbose, nigero-oligosaccharides, palatinose oligosaccharides, fucose, fructooligosaccharides (kestose, nystose and the like), maltotetraol, maltotriol, malto-oligosaccharides (maltotriose, maltotetraose, maltopentaose, maltohexaose, maltoheptaose and the like), lactulose, melibiose, raffinose, rhamnose, ribose, isomerized liquid sugars such as high fructose corn/starch syrup (e.g., HFCS55, HFCS42, or HFCS90), coupling sugars, soybean oligosaccharides, or glucose syrup; wherein the at least one amino acid additive is chosen from aspartic acid, arginine, glycine, glutamic acid, proline, threonine, theanine, cysteine, cystine, alanine, valine, tyrosine, leucine, isoleucine, asparagine, serine, lysine, histidine, ornithine, methionine, carnitine, aminobutyric acid (alpha-, beta-, and gamma-isomers), glutamine, hydroxyproline, taurine, norvaline, sarcosine, or salts thereof; and wherein the at least one inorganic salt additive is chosen from sodium chloride, potassium chloride, sodium sulfate, potassium citrate, europium chloride (EuCl$_3$), gadolinium chloride (GdCl$_3$), terbium chloride (TbCl$_3$), magnesium phosphate, magnesium sulfate, alum, magnesium chloride, potassium chloride, mono-, di-, tri-basic sodium or potassium salts of phosphoric acid, salts of hydrochloric acid, sodium carbonate, sodium bisulfate, or sodium bicarbonate.

In another embodiment, a functional sweetener composition is provided comprising at least one functional ingredient and at least one natural and/or synthetic high-potency sweetener in combination with at least one sweet taste improving polyol additive and at least one sweet taste improving polyamino acid additive; wherein the at least one polyol additive is chosen from erythritol, maltitol, mannitol, sorbitol, lactitol, xylitol, inositol, isomalt, propylene glycol, glycerol (glycerin), threitol, galactitol, palatinose, reduced isomalto-oligosaccharides, reduced xylo-oligosaccharides, reduced gentio-oligosaccharides, reduced maltose syrup, or reduced glucose syrup; and wherein the at least one polyamino acid additive is chosen from poly-L-aspartic acid, poly-L-lysine (e.g., poly-L-α-lysine or poly-L-ε-lysine), poly-L-ornithine (e.g., poly-L-α-ornithine or poly-L-ε-ornithine), poly-L-arginine, and other polymeric forms of amino acids, or salts thereof.

In another embodiment, a functional sweetener composition is provided comprising at least one functional ingredient and at least one natural and/or synthetic high-potency sweetener in combination with at least one sweet taste improving protein or protein hydrolysate additive and at least one sweet taste improving inorganic salt additive; wherein the at least one sweet taste improving protein or protein hydrolysate additive is chosen from bovine serum albumin (BSA), whey protein (including fractions or concentrates thereof such as 90% instant whey protein isolate, 34% whey protein, 50% hydrolyzed whey protein, and 80% whey protein concentrate), soluble rice protein, soy protein, protein isolates, protein hydrolysates, reaction products of protein hydrolysates, glycoproteins, and/or proteoglycans containing amino acids (e.g., glycine, alanine, serine, threonine, theanine, asparagine, glutamine, arginine, valine, isoleucine, leucine, norvaline, methionine, proline, tyrosine, hydroxyproline, or the like), collagen (e.g., gelatin), partially hydrolyzed collagen (e.g., hydrolyzed fish collagen), and collagen hydrolysates (e.g., porcine collagen hydrolysate); and wherein the at least one sweet taste improving inorganic salt additive is chosen from sodium chloride, potassium chloride, sodium sulfate, potassium citrate, europium chloride (EuCl$_3$), gadolinium chloride (GdCl$_3$), terbium chloride (TbCl$_3$), magnesium phosphate, magnesium sulfate, alum, magnesium chloride, potassium chloride, mono-, di-, tri-basic sodium or potassium salts of phosphoric acid, salts of hydrochloric acid, sodium carbonate, sodium bisulfate, or sodium bicarbonate.

In another embodiment, a functional sweetener composition is provided comprising at least one functional ingredient and rebaudioside A in combination with at least one natural and/or synthetic high-potency sweetener other than rebaudioside-A and at least one sweet taste improving composition.

In another particular embodiment, a functional sweetener composition is provided comprising at least one functional ingredient and rebaudioside A in combination with at least one synthetic high-potency sweetener, wherein the at least one synthetic high-potency sweetener functions as a sweet taste improving composition. Non-limiting examples of suitable sweet taste improving synthetic sweetener additives include sucralose, potassium acesulfame, aspartame, alitame, saccharin, neohesperidin dihydrochalcone, cyclamate, neotame, N—[N-[3-(3-hydroxy-4-methoxyphenyl)propyl]-L-α-aspartyl]-L-phenylalanine 1-methyl ester, N—[N-[3-(3-hydroxy-4-methoxyphenyl)-3-methylbutyl]-L-α-aspartyl]-L-phenylalanine 1-methyl ester, N—[N-[3-(3-methoxy-4-hydroxyphenyl)propyl]-L-α-aspartyl]-L-phenylalanine 1-methyl ester, salts thereof, and the like.

In one embodiment, a functional sweetener composition comprising at least one functional ingredient and a sweetener comprising rebaudioside-A (REBA), stevia, stevioside, mogroside IV, mogroside V, Luo Han Guo sweetener, monatin, curculin, sucralose, cyclamate, saccharin, aspartame, acesulfame potassium or other salts, or neotame, in combination with at least one sweet taste improving amino acid additive and at least one sweet taste improving polyol additive is provided. In a particular embodiment, the at least one sweet taste improving amino acid additive is present in an amount from about 100 ppm to about 25,000 ppm of the composition, and the at least one sweet taste improving polyol additive is present in an amount from about 400 to about 80,000 ppm of the composition. In a still more particular embodiment, the at least one sweet taste improving amino acid additive is glycine or alanine, and the at least one sweet taste improving polyol additive is erythritol.

In one embodiment, a functional sweetener composition comprising at least one functional ingredient and a sweetener comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with at least one sweet taste improving amino acid additive and at least one sweet taste improving protein or protein hydrolysate additive is provided. In a particular embodiment, the at least one sweet taste improving amino acid additive is present in an amount from about 100 to about 15,000 ppm of the composition, and the at least one sweet taste improving protein or protein hydrolysate additive is present in an amount from about 200 ppm to about 50,000 ppm of the composition. In a still more particular embodiment, the at least one sweet taste improving amino acid additive is glycine or lysine, and the at least one sweet taste improving protein or protein hydrolysate additive is a protein, a hydrolysate, or a reaction product of a hydrolysate of a protein containing glycine, alanine, serine, leucine, valine, isoleucine, proline, or threonine.

In one embodiment, a functional sweetener composition comprising at least one functional ingredient and a sweetener comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with at least one sweet taste improving protein or protein hydrolysate additive and at least one sweet taste improving polyol additive is provided. In a particular embodiment, the at least one sweet taste improving protein or protein hydrolysate additive is present in an amount from about 200 ppm to about 50,000 ppm of the composition, and at least one sweet taste improving polyol additive is present in an amount from about 400 to about 80,000 ppm of the composition. In a still more particular embodiment, the at least one sweet taste improving protein or protein hydrolysate additive is a protein, a hydrolysate, or a reaction product of a hydrolysate of proteins containing glycine, alanine, serine, leucine, valine, isoleucine, proline, or threonine, and the at least one sweet taste improving polyol additive is erythritol.

In one embodiment, a functional sweetener composition comprising at least one functional ingredient and a sweetener comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with at least one sweet taste improving carbohydrate additive is provided. In a particular embodiment, the at least one sweet taste improving carbohydrate additive is present in an amount from about 1,000 to about 100,000 ppm of the composition. In a still more particular embodiment, the composition comprises REBA and glucose, sucrose, HFCS, or D-fructose in an amount from about 10,000 ppm to about 80,000 ppm of the composition.

In one embodiment, a functional sweetener composition comprising at least one functional ingredient and a sweetener comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with at least one sweet taste improving polyol additive is provided. In a particular embodiment, the at least one sweet taste improving polyol additive is present in an amount from about 400 to about 80,000 ppm of the composition. In another particular embodiment, the at least one sweet taste improving polyol additive is present in an amount from about 5,000 to about 60,000 ppm of the functional sweetener composition. Non-limiting examples include at least one functional ingredient and a sweetener comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with propylene glycol, erythritol, or combinations thereof.

In one embodiment, a functional sweetener composition comprising rebaudioside-A (REBA) (with at least 50% REBA in a steviol glycoside mixture) in combination with at least one sweet taste improving polyol additive is provided. Desirably, the at least one sweet taste improving polyol additive comprises erythritol. In a particular embodiment of the functional sweetener composition, rebaudioside A is present in an amount from about 100 to about 3,000 ppm and the erythritol is present in an amount from about 400 to about 80,000 ppm of the total sweetener composition. In another embodiment of the functional sweetener composition, rebaudioside A is present in an amount from about 100 to about 3,000 ppm and the erythritol is present in an amount from about 5,000 to about 40,000 ppm of the total sweetener composition. In still another embodiment of the functional sweetener composition, rebaudioside A is present in an amount from about 100 to about 3,000 ppm and the erythritol is present in an amount from about 10,000 to about 35,000 ppm of the total sweetener composition. In another particular embodiment of the functional sweetener composition, rebaudioside A and erythritol are present in the sweetener composition in a ratio from about 1:4 to about 1:800, respectively. In yet another particular embodiment of the functional sweetener composition, rebaudioside A and erythritol are present in the sweetener composition in a ratio from about 1:20 to about 1:600, respectively; more particularly from about 1:50 to about 1.300; and still more particularly from about 1:75 to about 1:150.

In another embodiment, a functional sweetener composition comprising at least one functional ingredient and a sweetener composition comprising rebaudioside-A (REBA), stevia, stevioside, mogroside IV, mogroside V, Luo Han Guo sweetener, monatin, or curculin, in combination with at least one sweet taste improving synthetic sweetener additive is provided. In a particular embodiment, the functional sweetener composition comprises at least one functional ingredient and a sweetener comprising rebaudioside-A (REBA) in combination with saccharin or acesulfame potassium or other salts in an amount from about 10 ppm to about 100 ppm of the composition.

In one embodiment, a functional sweetener composition comprising at least one functional ingredient and a sweetener comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with at least one sweet taste improving carbohydrate additive and at least one sweet taste improving polyol additive is provided. In a particular embodiment, the at least one sweet taste improving carbohydrate additive is present in an amount from about 1,000 to about 100,000 ppm of the composition and at least one sweet taste improving polyol additive is present in an amount from about 400 to about 80,000 ppm of the composition. Non-limiting examples include at least one functional ingredient and a sweetener comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with tagatose, fructose or sucrose and erythritol.

In one embodiment, a functional sweetener composition comprising at least one functional ingredient and a sweetener comprising rebaudioside-A (REBA), stevia, stevioside, mogroside IV, mogroside V, Luo Han Quo sweetener, monatin, curculin, sucralose, saccharin, cyclamate, aspartame, acesulfame potassium or other salts, or neotame, in combination with at least one sweet taste improving inorganic salt additive is provided. Non-limiting examples include at least one functional ingredient and a sweetener comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with NaCl, KCl, $NaHSO_4 \cdot H_2O$, $NaH_2PO_4$, $MgSO_4$, $KAl(SO_4)_2$ (alum), magnesium phosphate, magnesium chloride, KCl and $KH_2PO_4$, or other combinations thereof. A particularly desirable embodiment comprises the at least one functional ingredient and a sweetener comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with a mixture of inorganic salt additives, such as chlorides, phosphates, and sulfates of sodium, magnesium, potassium, and calcium (e.g., sodium chloride and potassium chloride; potassium phosphate and potassium chloride; sodium chloride and sodium phosphate; calcium phosphate and calcium sulfate; magnesium chloride and magnesium phosphate; and calcium phosphate, calcium sulfate, and potassium sulfate).

In a particular embodiment, a functional sweetener composition comprising at least one functional ingredient and a sweetener comprises aspartame, acesulame potassium or other salts, and sucralose in combination with at least one sweet taste improving inorganic salt additive. In a particular embodiment, the at least one sweet taste improving inorganic salt additive is present in an amount in the range of about 25 to about 5,000 ppm of the composition. Non-limiting examples include at least one functional ingredient and a sweetener comprising aspartame, acesulfame potassium, and sucralose in combination with magnesium chloride; at least one functional ingredient and a sweetener comprising aspartame, acesulfame potassium, and sucralose in combination with magnesium sulfate; or at least one functional ingredient and a sweetener comprising aspartame, acesulfame potassium, and sucralose in combination with magnesium sulfate and sodium chloride.

In one embodiment, a functional sweetener composition comprising at least one functional ingredient and a sweetener comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with at least one sweet taste improving organic acid salt additive is provided. Non-limiting examples include at least one functional ingredient and a sweetener comprising rebaudioside-A (REBA), stevia, stevioside, mogroside IV, mogroside V, Luo Han Quo sweetener, monatin, curculin, sucralose, saccharin, cyclamate, aspartame, acesulfame potassium or other salts, or neotame, in combination with choline chloride in citrate buffer, D-gluconic acid sodium salt, guanidine HCl, D-glucosamine HCl, amiloride HCl, or combinations thereof.

In one embodiment, a functional sweetener composition comprising at least one functional ingredient and a sweetener comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with at least one sweet taste improving organic acid additive is provided. Non-limiting examples include at least one functional ingredient and a sweetener comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with fumaric acid, malic acid, tartaric acid, citric acid, adipic acid, ascorbic acid, tannic acid, succinic acid, glutaric acid, or combinations thereof.

In one embodiment, a functional sweetener composition comprising at least one functional ingredient and a sweetener comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with at least one sweet taste improving amino acid additive is provided. In a particular embodiment, the at least one sweet taste improving amino acid additive is present in an amount from about 100 to about 25,000 ppm of the composition. Non-limiting examples include at least one functional ingredient and a sweetener comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with glycine, L-alanine, L-serine, L-threonine, β-alanine, aminobutyric acid (alpha-, beta-, or gamma-isomers), L-aspartic acid, L-glutamic acid, L-lysine, glycine and L-alanine mixture, salt derivatives or combinations thereof.

In one embodiment, a functional sweetener composition comprising at least one functional ingredient and a sweetener comprising rebaudioside-A (EBA), stevia, stevioside, mogroside IV, mogroside V, Luo Han Guo sweetener, monatin, curculin, sucralose, saccharin, cyclamate, aspartame, acesulfame potassium or other salts, or neotame, in combination with at least one sweet taste improving surfactant additive is provided. Non-limiting examples include at least one functional ingredient and a sweetener comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with dioctyl sulfosuccinate sodium, cetylpyridinium chloride, hexadecyltrimethylammonium bromide, sucrose oleate, polysorbate 20, polysorbate 80, lecithin, or combinations thereof.

In one embodiment, a functional sweetener composition comprising at least one functional ingredient and a sweetener comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with at least one sweet taste improving polymer additive is provided. Non-limiting examples include at least one functional ingredient and a sweetener comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with cationic polymer such as polyethyleneimine, poly-L-lysine (e.g., poly-L-α-lysine or poly-L-ϵ-lysine), poly-L-ornithine (e.g., poly-L-α-ornithine or poly-L-ϵ-ornithine), chitosan, or combinations thereof.

In one embodiment, a functional sweetener composition comprising at least one functional ingredient and a sweetener comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with at least one sweet taste improving polymer additive and at least one sweet taste improving polyol additive is provided. In a particular embodiment, the at least one sweet taste improving polymer additive is present in an amount from about 30 to about 2,000 ppm of the composition, and the at least one sweet taste improving polyol additive is present in an amount from about 400 to about 80,000 ppm of the composition. Non-limiting examples include at least one functional ingredient and a sweetener comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with a hydrocolloid, such as a gum acacia seyal, and erythritol.

In one embodiment, a functional sweetener composition comprising at least one functional ingredient and a sweetener comprising rebaudioside-A (REBA), stevia, stevioside, mogroside TV, mogroside V, Luo Han Guo sweetener, monatin, curculin, sucralose, saccharin, cyclamate, aspartame, acesulfame potassium or other salts, or neotame, in combination with at least one sweet taste improving protein or protein hydrolysate additive is provided. Non-limiting examples include at least one functional ingredient and a sweetener comprising rebaudioside-A (REBA), stevia, stevioside, mogroside IV, mogroside V, Luo Han Quo sweetener, monatin, curculin, sucralose, saccharin, cyclamate, aspartame, acesulfame potassium or other salts, or neotame, in combination with bovine serum albumin (BSA), whey protein or combinations thereof.

In one embodiment, a functional sweetener composition comprising at least one functional ingredient and a sweetener comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with at least one sweet taste improving amino acid additive and at least one sweet taste improving inorganic acid salt additive is provided. In a particular embodiment, the at least one sweet taste improving amino acid additive is present in an amount from about 100 to about 25,000 ppm of the composition and the at least one sweet taste improving inorganic acid salt additive is present in an amount from about 25 to about 5,000 ppm of the composition. Non-limiting examples include at least one functional ingredient and a sweetener comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with glycine and alum; rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with glycine and potassium chloride; rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with glycine and sodium chloride; REBA in combination with glycine, potassium dihydrogen phosphate, and potassium chloride; and rebaudioside-A (REBA), stevia, stevioside, morgroside IV, morgroside V, Lo Han Guo, monatin, curculin, sucralose, saccharin, aspartame, acesulfame potassium or other salts, or neotame, in combination with glycine, sodium chloride, and potassium chloride.

In another embodiment, a functional sweetener composition comprising at least one functional ingredient and a sweetener comprising rebaudioside-A (REBA), stevia, stevioside, mogroside IV, mogroside V, Luo Han Quo sweetener, monatin, curculin, sucralose, saccharin, cyclamate, aspartame, acesulfame potassium or other salts, or neotame, in combination with at least one sweet taste improving carbohydrate additive and at least one sweet taste improving inorganic acid salt additive is provided. In a particular embodiment, the at least one sweet taste improving carbohydrate additive is present in an amount from about 1,000 to about 100,000 ppm of the composition and the at least one sweet taste improving inorganic acid salt additive is present in an amount from about 25 ppm to about 5,000 ppm. Non-limiting examples include at least one functional ingredient and a sweetener comprising rebaudioside-A (REBA), stevia, stevioside, mogroside IV, mogroside V, Luo Han Quo sweetener, monatin, curculin, sucralose, saccharin, cyclamate, aspartame, acesulfame potassium or other salts, or neotame, in combination with fructose, sucrose, or glucose and alum; at least one functional ingredient and a sweetener comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with fructose, sucrose, or glucose and potassium chloride; at least one functional ingredient and a sweetener comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with fructose, sucrose, or glucose and sodium chloride; at least one functional ingredient and a sweetener comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with fructose, sucrose, or glucose, potassium phosphate, and potassium chloride; and at least one functional ingredient and a sweetener comprising rebaudioside-A (EBA), stevia, stevioside, mogroside IV, mogroside V, Luo Han Guo sweetener, monatin, curculin, sucralose, saccharin, cyclamate, aspartame, acesulfame potassium or other salts, or neotame, in combination with fructose, sucrose, or glucose, sodium chloride, and potassium chloride.

In another embodiment, a functional sweetener composition comprising at least one functional ingredient and a sweetener comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with at least one sweet taste improving bitter additive and at least one sweet taste improving inorganic salt additive is provided. A non-limiting example include at least one functional ingredient and a sweetener comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with urea and sodium chloride.

In another embodiment, a functional sweetener composition comprising at least one functional ingredient and a sweetener comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with at least one sweet taste improving amino acid additive and at least one sweet taste improving polyamino acid additive is provided. In a particular embodiment, the at least one sweet taste improving amino acid additive is present in an amount from about 100 to about 25,000 ppm of the composition and the at least one sweet taste improving polyamino acid additive is present in an amount from about 30 to about 2,000 ppm of the composition. Non-limiting examples include at least one functional ingredient and a sweetener comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with glycine and poly-L-α-lysine; and at least one functional ingredient and a sweetener comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with glycine and poly-L-ε-lysine.

In another embodiment, a functional sweetener composition comprising at least one functional ingredient and a sweetener comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with at least one sweet taste improving amino acid additive and at least one sweet taste improving organic acid additive is provided. In a particular embodiment, the at least one sweet taste improving amino acid additive is present in an amount from about 100 to about 25,000 ppm of the composition and the at least one sweet taste improving organic acid additive is present in an amount from about 10 to about 5,000 ppm of the composition. A non-limiting example includes at least one functional ingredient and a sweetener comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with glycine and sodium gluconate.

In another embodiment, a functional sweetener composition comprising at least one functional ingredient and a sweetener comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with at least one sweet taste improving amino acid additive and at least one sweet taste improving carbohydrate additive is provided. In a particular embodiment, the at least one sweet taste improving amino acid additive is present in an amount from about 100 to about 25,000 ppm of the composition and the at least one sweet taste improving carbohydrate additive is present in an amount from about 1,000 to about 100,000 ppm of the composition. A non-limiting example includes at least one functional ingredient and a sweetener comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with L-alanine and fructose.

In another embodiment, a functional sweetener composition comprising at least one functional ingredient and a sweetener comprising rebaudioside-A (REBA), stevia, stevioside, mogroside IV, mogroside V, Luo Han Quo sweetener, monatin, curculin, sucralose, saccharin, cyclamate, aspartame, acesulfame potassium or other salts, or neotame, in combination with at least one sweet taste improving amino acid additive, at least one sweet taste improving polyol additive, at least one sweet taste improving inorganic salt additive, and at least one sweet taste improving organic acid salt additive is provided. In a particular embodiment, the at least one sweet taste improving amino acid additive is present in an amount from about 100 to about 25,000 ppm of the composition, the at least one sweet taste improving polyol additive is present in an amount from about 400 to about 80,000 ppm of the composition, the at least one sweet taste improving inorganic salt additive is present in an amount from about 50 to about 5,000 ppm of the composition, and the at least one sweet taste improving organic acid salt additive is present in an amount from about 20 to about 10,000 ppm of the composition. A non-limiting example includes at least one functional ingredient and a sweetener comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with erythritol, glycine, KCl, $KH_2PO_4$, and choline chloride.

In another embodiment, a functional sweetener composition comprising at least one functional ingredient and a sweetener comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with at least one sweet taste improving amino acid additive, at least one sweet taste improving carbohydrate additive, and at least one sweet taste improving polyol additive is provided. In a particular embodiment, the at least one sweet taste improving amino acid additive is present in an amount from about 100 to about 25,000 ppm of the composition, the at least one sweet taste improving carbohydrate additive is present in an amount from about 1,000 to about 100,000 ppm of the composition, and the at least one sweet taste improving polyol additive is present in an amount from about 400 to about 80,000 ppm of the composition. A non-limiting example includes at least one functional ingredient and a sweetener comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with L-alanine, fructose, and erythritol.

In another embodiment, a functional sweetener composition comprising at least one functional ingredient and a sweetener comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with at least one sweet taste improving amino acid additive, at least one sweet taste improving polyol additive, and at least one sweet taste improving inorganic acid salt additive is provided. In a particular embodiment, the at least one sweet taste improving amino acid additive is present in an amount from about 100 to about 25,000 ppm of the composition, the at least one sweet taste improving polyol additive is present in an amount from about 400 to about 80,000 ppm of the composition, and the at least one sweet taste improving inorganic acid salt additive is present in an amount from about 25 to about 5,000 ppm of the composition. A non-limiting example includes at least one functional ingredient and a sweetener comprising rebaudioside-A (REBA), stevia, stevioside, mogroside IV, mogroside V, Luo Han Guo sweetener, monatin, curculin, sucralose, saccharin, cyclamate, aspartame, acesulfame potassium or other salts, or neotame, in combination with erythritol, glycine, KCl, and $KH_2PO_4$.

In another embodiment, a functional sweetener composition comprising at least one functional ingredient and a sweetener comprising rebaudioside-A (REBA), stevia, stevioside, mogroside IV, mogroside V, Luo Han Guo sweetener, monatin, curculin, glycyrrihizin such as mono-ammonium glycyrrhizic acid salt hydrate, sucralose, saccharin, cyclamate, aspartame, acesulfame potassium or other salts, or neotame, in combination with a sweet taste improving inorganic acid salt additive is provided, A non-limiting example includes at least one functional ingredient and a sweetener comprising rebaudioside-A (REBA), stevia, stevioside, mogroside IV, mogroside V, Luo Han Guo sweetener, monatin, curculin, glycyrrihizin such as mono-ammonium glycyrrhizic acid salt hydrate, sucralose, saccharin, cyclamate, aspartame, acesulfame potassium or other salts, or neotame, in combination with sodium chloride.

The desired weight ratio of the natural and/or synthetic high-potency sweetener to sweet taste improving composition(s) in the functional sweetener composition will depend on the particular natural and/or synthetic high-potency sweetener, and the sweetness and other characteristics desired in the final product or orally ingestible composition. Natural and/or synthetic high-potency sweeteners vary greatly in their potency, ranging from about 30 times more potent than sucrose to about 8,000 times more potent than sucrose on a weight basis. In general, the weight ratio of the natural and/or synthetic high-potency sweetener to sweet taste improving composition may for example range from range between 10,000:1 and 1:10,000; a further non-limiting example may range from about 9,000:1 to about 1:9,000; yet another example may range from about 8,000:1 to about 1:8,000; a further example may range from about 7,000:1 to about 1:7,000; another example may range from about 6,000:1 to about 1:6000; in yet another example may range from about 5,000:1 to about 1:5,000; in yet another example may range from about 4,000:1 to about 1:4,000; in yet another example may range from about 3,000:1 to about 1:3,000; in yet another example may range from about 2,000:1 to about 1:2,000; in yet another example may range from about 1,500:1 to about 1:1,500; in yet another example may range from about 1,000:1 to about 1:1,000; in yet another example may range from about 900:1 to about 1:900; in yet another example may range from about 800:1 to about 1:800; in yet another example may range from about 700:1 to about 1:700; in yet another example may range from about 600:1 to about 1:600; in yet another example may range from about 500:1 to about 1:500; in yet another example may range from about 400:1 to about 1:400; in yet another example may range from about 300:1 to about 1:300; in yet another example may range from about 200:1 to about 1:200; in yet another example may range from about 150:1 to about 1:150; in yet another example may range from about 100:1 to about 1:1010 in yet another example may range from about 90:1 to about 1:90; in yet another example may range from about 80:1 to about 1:80; in yet another example may range from about 70:1 to about 1:70; in yet another example may range from about 60:1 to about 1:60; in yet another example may range from about 50:1 to about 1:50; in yet another example may range from about 40:1 to about 1:40; in yet another example may range from about 30:1 to about 1:30; in yet another example may range from about 20:1 to about 1:20; in yet another example may range from about 15:1 to about 1:15; in yet another example may range from about 10:1 to about 1:10; in yet another example may range from about 9:1 to about 1:9; in yet another example may range from about 8:1 to about 1:8; in yet another example may range from about 7:1 to about 1:7; in yet another example may range from about 6:1 to about 1:6; in yet another example may range from about 5:1 to about 1:5; in yet another example may range from about 4:1 to about 1:4; in yet another example may range from about 3:1 to about 1:3; in yet another example may range from about 2:1 to about 1:2; and in yet another example may be about 1:1; depending on the particular natural and/or synthetic high-potency sweetener selected.

It is contemplated that the combination of at least one natural and/or synthetic high-potency sweetener to at least one sweet taste improving composition may be carried out in any pH range that does not materially or adversely affect the taste of the functional sweetener composition or the functional sweetened composition. A non-limiting example of the pH range may be from about 2 to about 8. A further example includes a pH range from about 2 to about 5.

One of ordinary skill in the art may combine at least one natural and/or synthetic high-potency sweetener, at least one sweet taste improving composition, and at least one functional ingredient in any manner. For example, at least one natural and/or synthetic high-potency sweetener and at least one functional ingredient may be added to the functional sweetener composition before the at least one sweet taste improving composition. In another example, at least one natural and/or synthetic high-potency sweetener and at least one functional ingredient may be added to the functional sweetener composition after the at least one sweet taste improving composition. In yet another example, at least one natural and/or synthetic high-potency sweetener and at least one functional ingredient may be added to the functional sweetener composition simultaneously with the at least one sweet taste improving composition. In another example, at least one natural and/or synthetic high-potency sweetener may be added to the functional sweetener composition before the at least one sweet taste improving composition and at least one functional ingredient. In yet another example, at least one natural and/or synthetic high-potency sweetener may be added to the functional sweetener composition after the at least one sweet taste improving composition and at least one functional ingredient.

In yet another embodiment, at least one natural and/or synthetic high-potency sweetener may be combined with the at least one sweet taste improving composition and at least one functional ingredient prior to being added to a orally ingestible composition. For example, the at least one natural and/or synthetic high-potency sweetener may be in a pure, diluted, or concentrated form as a liquid (e.g., solution), solid (e.g., powder, chunk, pellet, grain, block, crystalline, or the like), suspension, gas state, or combinations thereof may be contacted with the at least one sweet taste improving composition which may be in a pure, diluted, or concentrated form as a liquid (e.g., solution), solid (e.g., powder, chunk, pellet, grain, block, crystalline, or the like), suspension, gas state, or combinations thereof and with the at least one functional ingredient which may be in pure, diluted, or concentrated form as a liquid (e.g., solution), solid (e.g., powder, chunk, pellet, grain, block, crystalline, or the like), suspension, gas state, or combinations thereof before all are contacted with an orally ingestible composition. In yet another embodiment, when there are more than one natural and/or synthetic high-potency sweetener, more than one sweet taste improving composition, or more than one functional ingredient, each component of the functional sweetener composition may be added simultaneously, in an alternating pattern, in a random pattern, or any other pattern.

IV. Tabletop Functional Sweetener Compositions

In a particular embodiment of the present invention, the functional sweetener compositions comprise a tabletop functional sweetener composition comprising at least one natural and/or synthetic high-potency sweetener in combination with: (i) at least one functional ingredient; (ii) at least one bulking agent; and (iii) optionally at least one sweet taste improving composition and/or anti-caking agent with improved temporal and/or flavor profile. In accordance with particular embodiments, suitable "bulking agents" include maltodextrin (10 DE, 18 DE, or 5 DE), corn syrup solids (20 or 36 DE), sucrose, fructose, glucose, invert sugar, sorbitol, xylose, ribulose, mannose, xylitol, mannitol, galactitol, erythritol, maltitol, lactitol, isomalt, maltose, tagatose, lactose, inulin, glycerol, propylene glycol, polyols, polydextrose, fructooligosaccharides, cellulose and cellulose derivatives, and the like, and mixtures thereof. Additionally, in accordance with still other embodiments of the invention, granulated sugar (sucrose) or other caloric sweeteners such as crystalline fructose, other carbohydrates, or sugar alcohols can be used as a bulking agent due to their provision of good content uniformity without the addition of significant calories. In one embodiment, a bulking agent may be used as a sweet taste improving composition.

As used herein the phrase "anti-caking agent" and "flow agent" refer to any composition which prevents, reduces, inhibits, or suppresses at least one natural and/or synthetic high-potency sweetener molecule from attaching, binding, or contacting to another natural and/or synthetic high-potency sweetener molecule. Alternatively, anti-caking agent may refer to any composition which assists in content uniformity and uniform dissolution. In accordance with particular embodiments, non-limiting examples of anti-caking agents include cream of tartar, calcium silicate, silicon dioxide, microcrystalline cellulose (Avicel, FMC BioPolymer, Philadelphia, Pa.), and tricalcium phosphate. In one embodiment, the anti-caking agents are present in the tabletop functional sweetener composition in an amount from about 0.001 to about 3% by weight of the tabletop functional sweetener composition.

Tabletop functional sweetener compositions are embodied and packaged in numerous different forms and it is intended that the tabletop functional sweetener compositions of the present invention may be of any form known in the art. In accordance with particular embodiments, non-limiting examples include powder form, granular form, packets, tablets, sachets, pellets, cubes, solids, and liquids.

In an embodiment, a tabletop functional sweetener composition comprises a single-serving (portion control) packet comprising a dry-blend of a functional sweetener formulation. Dry-blend formulations generally may comprise powder or granules. Although the tabletop functional sweetener packet may be of any size, an illustrative non-limiting example of conventional portion control tabletop sweetener packets are approximately 2.5 by 1.5 inches and hold approximately 1 gram of a sweetener composition having a sweetness equivalent to 2 teaspoons of granulated sugar (~8 g). The amount of natural and/or synthetic high-potency sweetener in a dry-blend tabletop functional sweetener formulation will vary due to the varying potency of different natural and/or synthetic high-potency sweeteners. In a particular embodiment, a dry-blend tabletop functional sweetener formulation may comprise a natural and/or synthetic high-potency sweetener in an amount from about 1% (w/w) to about 10% (w/w) of the tabletop functional sweetener composition.

Solid tabletop functional sweetener embodiments include cubes and tablets. A non-limiting example of conventional cubes are equivalent in size to a standard cube of granulated sugar, which is approximately $2.2 \times 2.2 \times 2.2$ $cm^3$ and weigh approximately 8 g. In one embodiment, a solid tabletop sweetener is in the form of a tablet or any other form known to those skilled in the art.

A tabletop functional sweetener composition may also be embodied in the form of a liquid, wherein the NHPS is combined with a liquid carrier. Suitable non-limiting examples of carrier agents for liquid tabletop functional sweeteners include water, alcohol, polyol, glycerin base or citric acid base dissolved in water, and mixtures thereof. Due to the varying potencies of the different high-potency sweeteners, the amount of high-potency sweetener in a liquid tabletop functional sweetener formulation will also vary. The sweetness equivalent of a tabletop functional sweetener composition for any of the forms described herein or known in the art may be varied to obtain a desired sweetness profile. For example, a tabletop functional sweetener composition may comprise a sweetness comparable to that of an equivalent amount of standard sugar. In another embodiment, the tabletop functional sweetener composition may comprise a sweetness of up to 100 times that of an equivalent amount of sugar. In another embodiment, the tabletop functional sweetener composition may comprise a sweetness of up to 90 times, 80 times, 70 times, 60 times, 50 times, 40 times, 30 times, 20 times, 10 times, 9 times, 8 times, 7 times, 6 times, 5 times, 4 times, 3 times, and 2 times that of an equivalent amount of sugar.

In one embodiment, the tabletop functional sweetener composition may also be formulated for targeted uses, for example, in beverage, food, pharmaceutical, cosmetics, herbal/vitamins, tobacco, and in any other products which may be sweetened. For example, a tabletop functional sweetener composition for baking may be formulated having additional protecting agents such as encapsulants. Other forms will be readily apparent to those skilled in the tabletop sweetener art.

Commonly used methods for making powder or granulated functional sweetener formulations for packets include fluid bed agglomeration processes. Other methods for making tabletop sweetener compositions are well known to those of ordinary skill in the art.

Those skilled in the art appreciate that the amount of natural and/or synthetic high-potency sweetener and amount and types of sweet taste improving composition, bulking agent, and/or anti-caking agent can be modified in order to tailor the taste of the tabletop sweetener composition to a desired profile and end use.

Specific embodiments of tabletop sweetener compositions and methods of making tabletop functional sweetener compositions are disclosed in U.S. Provisional Application No. 60/805,209, filed on Jun. 19, 2006, by DuBois, et al., the disclosure of which is incorporated herein by reference in its entirety.

V. Orally Ingestible Compositions

As used herein, "orally ingestible composition" and "sweetenable composition" are synonymous and mean substances which are contacted with the mouth of man or animal, including substances which are taken into and subsequently ejected from the mouth and substances which are drunk, eaten, swallowed or otherwise ingested, and are safe for human or animal consumption when used in a generally acceptable range. These compositions include food, beverage, pharmaceutical, tobacco, nutraceutical, oral hygienic/cosmetic products, and the like. Non-limiting examples of these products include non-carbonated and carbonated beverages such as colas, ginger ales, root beers, ciders, fruit-flavored soft drinks (e.g., citrus-flavored soft drinks such as lemon-lime or orange), powdered soft drinks, and the like; fruit juices originating in fruits or vegetables, fruit juices including squeezed juices or the like, fruit juices containing fruit particles, fruit beverages, fruit juice beverages, beverages containing fruit juices, beverages with fruit flavorings, vegetable juices, juices containing vegetables, and mixed juices containing fruits and vegetables; sport drinks, energy drinks, near water and the like drinks (e.g., water with natural or synthetic flavorants); tea type or favorite type beverages such as coffee, cocoa, black tea, green tea, oolong tea and the like; beverages containing milk components such as milk beverages, coffee containing milk components, café au lait, milk tea, fruit milk beverages, drinkable yogurt, lactic acid bacteria beverages or the like; dairy products; bakery products; desserts such as yogurt, jellies, drinkable jellies, puddings, Bavarian cream, blancmange, cakes, brownies, mousse and the like, sweetened food products eaten at tea time or following meals; frozen foods; cold confections, e.g. types of ice cream such as ice cream, ice milk, lacto-ice and the like (food products in which sweeteners and various other types of raw materials are added to milk products, and the resulting mixture is agitated and frozen), and ice confections such as sherbets, dessert ices and the like (food products in which various other types of raw materials are added to a sugary liquid, and the resulting mixture is agitated and frozen); ice cream; general confections, e.g., baked confections or steamed confections such as cakes, crackers, biscuits, buns with beanjam filling and the like; rice cakes and snacks; table top products; general sugar confections such as chewing gum (e.g. including compositions which comprise a substantially water-insoluble, chewable gum base, such as chicle or substitutes thereof, including jetulong, guttakay rubber or certain comestible natural synthetic resins or waxes), hard candy, soft candy, mints, nougat candy, jelly beans and the like; sauces including fruit flavored sauces, chocolate sauces and the like; edible gels; cremes including butter cremes, flour pastes, whipped cream and the like; jams including strawberry jam, marmalade and the like; breads including sweet breads and the like or other starch products; spice; general condiments including seasoned soy sauce used on roasted meats, roast fowl, barbecued meat and the like, as well as tomato catsup, sauces, noodle broth and the like; processed agricultural products, livestock products or seafood; processed meat products such as sausage and the like; retort food products, pickles, preserves boiled in soy sauce, delicacies, side dishes; snacks such as potato chips, cookies, or the like; cereal products; drugs or quasi-drugs that are administered orally or used in the oral cavity (e.g., vitamins, cough syrups, cough drops, chewable medicine tablets, amino acids, bitter-tasting drug or pharmaceutical agents, acidulants or the like), wherein the drug may be in solid, liquid, gel, or gas form such as a pill, tablet, spray, capsule, syrup, drop, troche agent, powder, and the like; personal care products such as other oral compositions used in the oral cavity such as mouth freshening agents, gargling agents, mouth rinsing agents, toothpaste, tooth polish, dentrifices, mouth sprays, teeth-whitening agents and the like; dietary supplements; tobacco products including smoke and smokeless tobacco products such as snuff, cigarette, pipe and cigar tobacco, and all forms of tobacco such as shredded filler, leaf, stem, stalk, homogenized leaf cured, reconstituted binders and reconstituted tobacco from tobacco dust, fines or ether sources in sheet, pellet or other forms, tobacco substitutes formulated from non-tobacco materials, dip or chewing tobacco; animal feed; and nutraceutical products, which includes any food or part of a food that may provide medicinal or health benefits, including the prevention and treatment of disease (e.g., cardiovascular disease and levels of high cholesterol in the blood, diabetes, osteoporosis, inflammation, or autoimmune disorders).

Generally, the amount of natural and/or synthetic high-potency sweetener present in a sweetened composition varies widely depending on the particular type of sweetened composition and its desired sweetness. Those of ordinary skill in the art can readily discern the appropriate amount of sweetener to put in the sweetened composition. In a particular embodiment, the at least one natural and/or synthetic high-potency sweetener is present in the sweetened composition in an amount in the range of about 1 to about 5,000 ppm of the sweetened composition and the at least one sweet taste improving composition is present in the sweetened composition in an amount in the range of about 0.1 to about 100,000 ppm of the sweetened composition.

In accordance with particular embodiments, suitable amounts of natural high-potency sweeteners for sweetenable compositions comprise amounts in the range from about 100 ppm to about 3,000 ppm for rebaudioside A; from about 50 ppm to about 3,000 ppm for stevia; from about 50 ppm to about 3,000 ppm for stevioside; from about 50 ppm to about 3,000 ppm for mogroside IV; from about 50 ppm to about 3,000 ppm for mogroside V; from about 50 ppm to about 3,000 ppm for Luo Han Guo sweetener; from about 5 ppm to about 300 ppm for monatin, from about 5 ppm to about 200 ppm for thaumatin; and from about 50 ppm to about 3,000 ppm for mono-ammonium glycyrrhizic acid salt hydrate.

In accordance with particular embodiments, suitable amounts of synthetic high-potency sweeteners for sweetenable compositions comprise a range from about 1 ppm to about 60 ppm for alitame; from about 10 ppm to about 600 ppm for aspartame; from about 1 ppm to about 20 ppm for neotame; from about 10 ppm to about 500 ppm for acesulfame potassium; from about 50 ppm to about 5,000 ppm for cyclamate; from about 10 ppm to about 500 ppm for saccharin; from about 5 ppm to about 250 ppm for sucralose; from about 1 ppm to about 20 ppm for N—[N-[3-(3-hydroxy-4-methoxyphenyl)propyl]-L-α-aspartyl]-L-phenylalanine 1-methyl ester; from about 1 ppm to about 20 ppm for N—[N-[3-(3-hydroxy-4-methoxyphenyl)-3-methylbutyl]-L-α-aspartyl]-L-phenylalanine 1-methyl ester; and from about 1 ppm to about 20 ppm for N—[N-[3-(3-methoxy-4-hydroxyphenyl)propyl]-L-α-aspartyl]-L-phenylalanine 1-methyl ester.

In one embodiment, an orally ingestible composition comprises a carbonated beverage comprising at least one natural and/or synthetic high-potency sweetener, at least one sweet taste improving composition, and at least one functional ingredient; wherein the at least one natural and/or synthetic high-potency sweetener comprises rebaudioside A, rebaudioside B, rebaudioside C, rebaudioside D, rebaudioside A, rebaudioside F, dulcoside A, dulcoside B, rubusoside, stevia, stevioside, mogroside IV, mogroside V, Luo Han Guo sweetener, siamenoside, monatin and its salts (monatin SS, RR, RS, SR), curculin, glycyrrhizic acid and its salts, thaumatin, monellin, mabinlin, brazzein, hernandulcin, phyllodulcin, glycyphyllin, phloridzin, trilobatin, baiyunoside, osladin, polypodoside A, pterocaryoside A, pterocaryoside B, mukurozioside, phlomisoside I, periandrin I, abrusoside A, cyclocarioside I, sucralose, acesulfame potassium or other salts, aspartame, alitame, saccharin, neohesperidin dihydrochalcone, cyclamate, neotame, N—[N-[3-(3-hydroxy-4-methoxyphenyl)propyl]-L-α-aspartyl]-L-phenylalanine 1-methyl ester, N—[N-[3-(3-hydroxy-4-methoxyphenyl)-3-ethylbutyl]-L-α-aspartyl]-L-phenylalanine 1-methyl ester, N—[N-[3-(3-methoxy-4-hydroxyphenyl)propyl]-L-α-aspartyl]-L-phenylalanine 1-methyl ester, salts thereof, or combinations thereof; wherein the at least one sweet taste improving composition is selected from the group consisting of carbohydrates, polyols, amino acids and their corresponding salts, polyamino acids and their corresponding salts, sugar acids and their corresponding salts, organic acids, inorganic acids, organic salts, inorganic salts, bitter compounds, flavorants, astringent compounds, polymers, proteins or protein hydrolysates, surfactants, emulsifiers, flavonoids, alcohols, and combinations thereof; and wherein the at least one functional ingredient comprises at least one mineral. Specific combinations of sweet taste improving compositions are disclosed in U.S. Provisional Application Nos. 60/739,302 and 60/739,124.

In particular embodiment, the at least one functional ingredient may require special processing in order to be incorporated into the functional sweetened composition. This is particularly relevant when the functional sweetened composition is aqueous and the at least one functional ingredient is hydrophobic. Techniques of incorporating hydrophobic compositions into aqueous solutions are well known to those of ordinary skill in the art, non-limiting examples of which include homogenization, encapsulation, emulsions, and addition of stabilizers, gums, and the like.

In a particular embodiment, the process for producing a substantially stable dispersion of the at least one functional ingredient in an aqueous functional sweetened composition comprises mixing the at least one functional ingredient with the aqueous orally ingestible composition to form a first dispersion of particles, heating the first dispersion of particles, and homogenizing the heated first dispersion particles to obtain an aqueous functional sweetened composition comprising particles of the at least one functional ingredient ranging in size from about 0.1 micron to about 50 microns. This method is disclosed further in U.S. application Ser. Nos. 10/458,692 and 11/315,206, filed on Oct. 24, 2003, and Dec. 23, 2005, respectively, the disclosures of which are incorporated herein by reference in their entirety.

The functional sweetener compositions and orally ingestible compositions containing the same are useful for providing healthy benefits beyond basic nutrition. For example, such benefits may include, but are not limited to, improving bone strength, reducing the risk of osteoporosis, improving cardiac and nervous system function, reducing the incidence of anemia, reducing the risk of goiter and birth defects such as cretinism, and reducing skin rashes.

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description therein, may suggest themselves to those skilled in the art without departing from the spirit of the present invention and/or the scope of the appended claims. Unless otherwise specified, %'s are by weight.

EXAMPLE SET A

Example A1

A rebaudioside A diet cola beverage (sweetness level 10% sucrose equivalent) is prepared with 100 mg of calcium per serving (240 mL), 40 mg of magnesium, 0.8 mg iron, 400 ppm of rebaudioside A, and 3.5% erythritol.

Example A2

A rebaudioside A diet lemon-lime beverage (sweetness level 10% sucrose equivalent) is prepared with 100 mg of calcium per serving (~240 mL), 40 mg of magnesium, 0.8 mg iron, 400 ppm of rebaudioside A, and 3.5% erythritol.

Example A3

Commercially available Minute Maid Orange Juice (100% juice product) is diluted 1:1 with a 360 ppm rebaudioside A/citrate composition. The product contains 100 mg of calcium per serving (~240 mL), 40 mg of magnesium, 0.8 mg iron, and 180 ppm rebaudioside A (equivalent to 5% sucrose).

Example A4

Commercially available Nestea Cool Lemon Iced Tea product is diluted 1:1 with a 360 ppm rebaudioside A/citrate composition. The product contains 100 mg of calcium per serving (~240 mL), 40 mg of magnesium, 0.8 mg iron, and 180 ppm of rehaudioside A (equivalent to 5% sucrose).

The following Examples B1-B3, C1-C3, D, E1-E3, and F illustrate methods of making purified rebaudioside A in accordance with particular embodiments of this invention:

EXAMPLE SET B

TABLE 2

Summary of Examples B1-3

|    | Crude Rebaudioside A (g) | Ethanol (95%) (mL) | Solvent Methanol (99%) (mL) | Water (mL) | Heating T (° C.) | Drying T (° C.) | Yield (g) | HPLC Purity (wt/wt %) |
|----|---|---|---|---|---|---|---|---|
| B1 | 400 | 1200 | 400 | 320 | 50 | 50 | 130 | 98.9 |
| B2 | 100 | 320 | 120 | 50 | 30-40 | 60 | 72 | 98.3 |
| B3 | 50 | 160 | 60 | 25 | ~30 | 60 | 27.3 | 98.2 |

Example B1

Crude rebaudioside A (77.4% purity) mixture was obtained from a commercial source. The impurities (6.2% stevioside, 5.6% rebaudioside C, 0.6% rebauiodioside F, 1.0% other steviolglycosides, 3.0% rebaudioside D, 4.9% rebaudioside B, 0.3% steviolbioside) were identified and quantified using HPLC on dry basis, moisture content 4.7%.

Crude rebaudioside A (400 g), ethanol (95%, 1200 mL), methanol (99%, 400 mL) and water (320 mL) were combined and heated to 50° C. for 10 minutes. The clear solution was cooled to 22° C. for 16 hours. The white crystals were filtered and washed twice with ethanol (2×200 mL, 95%) and dried in a vacuum oven at 50° C. for 16-24 hours under reduced pressure (20 mm).

The final composition of substantially pure rebaudioside A (130 g) comprised 98.91% rebaudioside A, 0.06% stevioside, 0.03% rebaudioside C, 0.12% rebaudioside F, 0.13% other steviolglycosides, 0.1% rebaudioside D, 0.49% rebaudioside B and 0.03% steviolbioside, all by weight.

Example B2

Crude rebaudioside A (80.37%) was obtained from a commercial source. The impurities (6.22% stevioside, 2.28% rebaudioside C, 0.35% Dulcoside, 0.78% rebaudioside F, 0.72% other steviolglycosides, 3.33% rebaudioside B, 0.07% steviolbioside) were identified by HPLC on dry basis, moisture content 3.4%.

Crude rebaudioside A (100 g), ethanol (95%, 320 mL), methanol (99%, 120 mL) and water (50 mL) were combined and heated to 30-40° C. for 10 minutes. The clear solution was cooled to 22° C. for 16 hours, The white crystals were filtered and washed twice with ethanol (2×50 mL, 95%). The wet filter cake (88 g) was slurried in ethanol (95%, 1320 mL) for 16 hours, filtered, washed with ethanol (95%, 2×100 mL) and dried in a vacuum oven at 60° C. for 16-24 hours under reduced pressure (20 mm).

The final composition of substantially pure rebaudioside A (72 g) comprised 98.29% rebaudioside A, 0.03% stevioside, 0.02% rebaudioside C, 0.17% rebaudioside F, 0.06% rebaudioside D and 1.09% rebaudioside B. Steviolbioside was not detected by HPLC.

Example B3

Crude rebaudioside A (80.37%) was obtained from a commercial source. The impurities (6.22% stevioside, 2.28% rebaudioside C, 0.35% Dulcoside, 0.78% rebaudioside F, 0.72% other steviolglycosides, 3.33% rebaudioside B, 0.07% steviolbioside) were identified by HPLC on dry basis, moisture content 3.4%.

Crude rebaudioside A (50 g), ethanol (95%, 160 mL), methanol (99%, 60 mL) and water (25 mL) were combined and heated to approximately 30° C. for 10 minutes. The clear solution was cooled to 22° C. for 16 hours. The white crystals were filtered and washed twice with ethanol (2×25 mL, 95%). The wet filter cake (40 g) was slurried in methanol (99%, 600 mL) for 16 hours, filtered, washed with methanol (99%, 2×25 mL) and dried in a vacuum oven at 60° C. for 16-24 hours under reduced pressure (20 mm).

The final composition of substantially pure rebaudioside A (27.3 g) comprised 98.22% rebaudioside A, 0.04% stevioside, 0.04% rebaudioside C, 0.18% rebaudioside F, 0.08% rebaudioside D and 1.03% rebaudioside B. Steviolbioside was not detected by HPLC.

EXAMPLE SET C

TABLE 3

Summary of Examples C1-3

|    | Crude Rebaudioside A (g) | Ethanol (95%) (mL) | Organic Co-solvent (mL) | Water (mL) | Wash Solvent | Yield (g) | HPLC Purity (%) |
|----|---|---|---|---|---|---|---|
| C1 | 5 | 15 | Methanol (6) | 3.5 | EtOH/MeOH (3:1 v/v) | 2.6 | >99 |
| C2 | 5 | 15 | Methanol (5) | 4 | EtOH/MeOH (3:1 v/v) | 2.3 | >99 |
| C3 | 5 | 16 | Methanol (6) | 2.5 | *EtOH/MeOH (8:3 v/v) | 3.2 | >98 |

Example C1

A mixture of crude rebaudioside A (80.37% purity, 5 g), ethanol (95%, 15 mL), methanol (5 mL) and water (3.5 mL) were combined and heated to reflux for 10 minutes. The clear solution was cooled to 22° C. for 16 hours while stirring. The white crystalline product was filtered, washed twice with ethanol:methanol (5.0 mL, 3:1, v/v) mixture and dried in a vacuum oven at 50° C. for 16-24 hours under reduced pressure (20 mm) to yield 2.6 g of purified product (>99% by HPLC).

Example C2

A mixture of crude rebaudioside A (80.37% purity, 5 g), ethanol (95%, 15 mL), methanol (5 mL) and water (4.0 mL) were combined and heated to reflux for 10 minutes. The clear solution was cooled to 22° C. for 16 hours while stirring. The white crystalline product was filtered, washed twice with ethanol:methanol (5.0 mL, 3:1, v/v) mixture and dried in a vacuum oven at 50° C. for 16-24 hours under reduced pressure (20 mm) to yield 2.3 g of purified product (>99% by HPLC).

Example C3

A mixture of crude rebaudioside A (80.37% purity, 5 g), ethanol (95%, 16 mL), methanol (6 mL) and water (2.5 mL) were combined and heated to reflux for 10 minutes. The clear solution was cooled to 22° C. for 2 hours. During this time, crystals started to appear. The mixture is stirred at room temperature for 16 hours. The white crystalline product was filtered, washed twice with ethanol:methanol (5.0 mL, 8:3, v/v) mixture and dried in a vacuum oven at 50° C. for 16-24 hours under reduced pressure (20 mm) to yield 3.2 g of purified product (>98% by HPLC).

EXAMPLE D

TABLE 4

Summary of Example D

| | | Solvent | | | | |
|---|---|---|---|---|---|---|
| | Crude Rebaudioside A (g) | Organic Solvent (mL) | Water (mL) | Wash Solvent | Yield (g) | HPLC Purity (%) |
| D | 50 | EtOH (160) | 40 | EtOH | 19.8 | 99.5 |

A mixture of crude rebaudioside A (80.37% purity, 50 g), ethanol (95%, 160 mL) and water (40 mL) were combined and heated to reflux for 30 minutes. The mixture was then allowed to cool to ambient temperature for 16-24 hours. The white crystalline product was filtered, washed twice with ethanol (95%, 25 mL), and dried in a vacuum oven at 60° C. for 16-24 hours under reduced pressure (20 mm) to yield 19.8 g of purified product (99.5% by HPLC).

EXAMPLE E

TABLE 5

Summary of Examples E1-3

| | Crude Rebaudioside A (g) | Ethanol (95%) (mL) | Organic Co-solvent (mL) | Water (mL) | Methanol Slurry (mL) | Yield (g) | HPLC Purity (%) |
|---|---|---|---|---|---|---|---|
| E1 | 50 | 160 | Methanol (60) | 25 | 200 | 12.7 | >97 |
| E2 | 50 | 160 | Methanol (60) | 25 | 300 | 18.6 | >97 |
| E3 | 50 | 160 | Methanol (60) | 25 | 350 | 22.2 | >97 |

Example E1

A mixture of crude rebaudioside A (41% purity, 50 g), ethanol (95%, 160 mL), methanol (99.8%, 60 mL) and water (25 mL) were combined by stirring at 22° C. A white product crystallized out in 5-20 hours. The mixture was stirred for additional 48 hours. The white crystalline product was filtered and washed twice with ethanol (95%, 25 mL). The wet cake of white crystalline product then was slurried in methanol (99.8%, 200 mL) for 16 hours, filtered, washed twice with methanol (99.8%, 25 mL), and dried in a vacuum oven at 60° C. for 16-24 hours under reduced pressure (20 mm) to give 12.7 g of purified product (>97% by HPLC).

Example E2

A mixture of crude rebaudioside A (48% purity, 50 g), ethanol (95%, 160 mL), methanol (99.8%, 60 mL) and water (25 mL) was combined by stirring at 22° C. The white product crystallized out in 3-6 hours. The mixture was stirred for additional 48 hours. The white crystalline product was filtered and washed twice with ethanol (95%, 25 mL). The wet cake of white crystalline product then was slurried in methanol (99.8%, 300 mL) for 16 hours, filtered, washed twice with methanol (99.8%, 25 mL) and dried in a vacuum oven at 60° C. for 16-24 hours under reduced pressure (20 mm) to give 18.6 g of purified product (>97% by HPLC).

Example E3

A mixture of crude rebaudioside A (55% purity, 50 g), ethanol (95%, 160 mL), methanol (99.8%, 60 mL) and water (25 mL) was combined by stirring at 22° C. The white product crystallized out in 15-30 minutes. The mixture was stirred for an additional 48 hours. The white crystalline product was filtered and washed twice with ethanol (95%, 25 mL). The wet cake of white crystalline product was slurried in methanol (99.8%, 350 mL) for 16 hours, filtered, washed twice with methanol (99.8%, 25 mL) and dried in a vacuum oven at 60° C. for 16-24 hours under reduced pressure (20 mm) to give 22.2 g of purified product (>97% by HPLC).

EXAMPLE F

A solution of rebaudioside A (>97% pure by HPLC) was prepared in double distilled water (12.5 gm in 50 mL, 25% concentration) by stirring the mixture at 40° C. for 5 minutes. An amorphous form of rebaudioside A was formed by immediately using the clear solution for spray drying with the Lab-Plant spray drier SD-04 instrument (Lab-Plant Ltd., West Yorkshire, U.K.). The solution was fed through the feed pump into the nozzle atomizer which atomized it into a spray of droplets with the help of a constant flow of nitrogen/air. Moisture was evaporated from the droplets under controlled temperature conditions (about 90 to about 97° C.) and airflow conditions in the drying chamber and resulted in the formation of dry particles. This dry powder (11-12 g, $H_2O$ 6.74%) was discharged continuously from the drying chamber and was collected in a bottle. The solubility in water at room temperature was determined to be >35.0%.

EXAMPLE SET G

Sensory evaluation of the samples prepared in Example Set G was carried out under the following protocol, similar to that described hereinabove. In this test protocol, none of the samples were swallowed. All samples were expectorated and the mouth was rinsed with water after the tasting. Immediately upon sensing maximal sweetness, the sample was expectorated, the mouth was rinsed with water and the rate of sweetness decay ("Sweetness Linger") was measured, where attention was focused on the sweetness 3-4 min after the water rinse. After sample tasting was complete, a salty oyster cracker was chewed followed by a water rinse, and at least 5 minutes followed before tasting the next sample. The sweetness linger was rated by a panel of experts in the sensory evaluation of foods and beverages using the following scale:

0=no sweetness linger, 1 very slight sweetness linger, 2=slight sweetness linger, 3 moderate sweetness linger, 4=moderately high sweetness linger, 5=high sweetness linger.

The "Sweetness Linger" rating for sucrose observed by this protocol is defined as 0. The Sweetness Linger of a 500 ppm of REBA control sample is defined as 5. Experimental samples were tasted by the same protocol, always allowing sufficient time between samples to ensure re-equilibration of the sensory system. Re-tasting of control samples during the course of the experiment was allowed and encouraged.

The comparison taste test was performed between two controls and addition of sweet taste improving additive on the onset and/or sweetness linger.

Control Samples

REBA is a natural non-caloric sweetener with a very clean flavor profile (i.e., only sweet) and an acceptable sweetness onset rate but with a sweetness which lingers quite noticeably more than that of carbohydrate sweeteners.

The effects of formulation change on the sweetness linger of 400 ppm REBA (equivalent to 8 g sucrose) in a citric acid/potassium citrate composition equivalent to that in a diet lemon-lime beverage were evaluated. The sweetness linger rating of this solution was determined to be 5.

8 g of sugar was dissolved in 100 ml of citrate buffer. The sweetness linger rating of this control sample was determined to be 0.

The following Examples G 1-50 illustrate combinations of rebaudioside A and sweet taste improving compositions in accordance with particular embodiments of this invention:

Example G1

400 ppm of REBA was dissolved in a citric acid/potassium citrate composition equivalent to that in a diet lemon-lime beverage. 1,250 ppm of trehalose was then mixed with the base solution. The sweetness linger of this solution was determined to be 2.

Example G2

400 ppm of REBA was dissolved in a citric acid/potassium citrate composition equivalent to that in a diet lemon-lime beverage. 10,000 ppm fructooligosaccharide (55%) was then mixed with the base solution. The sweetness linger of this solution was determined to be 3.

Example G3

400 ppm of REBA was dissolved in a citric acid/potassium citrate composition equivalent to that in a diet lemon-lime beverage. 200 ppm acacia senegal was then mixed with the base solution. The sweetness linger of this solution was determined to be 3.

Example G4

400 ppm of REBA was dissolved in a citric acid/potassium citrate composition equivalent to that in a diet lemon-lime beverage. 2,500 ppm β-Cyclodextrin was then mixed with the base solution. The sweetness linger of this solution was determined to be 3.

Example G5

400 ppm of REBA was dissolved in a citric acid/potassium citrate composition equivalent to that in a diet lemon-lime beverage. 5,000 ppm glycerol was then mixed with the base solution. The sweetness linger of this solution was determined to be 3,

Example G6

400 ppm of REBA was dissolved in a citric acid/potassium citrate composition equivalent to that in a diet lemon-lime beverage. 2,500 ppm of Fibersol-2 was then mixed with the base solution. The sweetness linger of this solution was determined to be 1.

Example G7

400 ppm of REBA was dissolved in a citric acid/potassium citrate composition equivalent to that in a diet lemon-lime beverage. 125 ppm collagen (unflavored gelatin) was then mixed with the base solution. The sweetness linger of this solution was determined to be 2. This formulation was found to have sugar-like taste characteristics.

Example G8

400 ppm of REBA was dissolved in a citric acid/potassium citrate composition equivalent to that in a diet lemon-lime beverage. 2,000 ppm collagen (unflavored gelatin) was then mixed with the base solution. The sweetness linger of this solution was determined to be 3. This formulation was found to have sugar-like taste characteristics.

Example G9

400 ppm of REBA was dissolved in a citric acid/potassium citrate composition equivalent to that in a diet lemon-lime beverage. 10,000 ppm of D-tagatose was then mixed with the base solution. The sweetness linger of this solution was determined to be 2.

Example G10

400 ppm of REBA was dissolved in a citric acid/potassium citrate composition equivalent to that in a diet lemon-lime beverage. 150 ppm of sodium chloride was then mixed with the base solution. The sweetness linger of this solution was determined to be 3.

Example G11

400 ppm of REBA was dissolved in a citric acid/potassium citrate composition equivalent to that in a diet lemon-lime beverage. 150 ppm of potassium chloride was then mixed with the base solution. The sweetness linger of this solution was determined to be 3.

Example G12

400 ppm of REBA was dissolved in a citric acid/potassium citrate composition equivalent to that in a diet lemon-lime beverage. 300 ppm of potassium dihydrogenphosphate was then mixed with the base solution. The sweetness linger of this solution was determined to be 3.

Example G13

400 ppm of REBA was dissolved in a citric acid/potassium citrate composition equivalent to that in a diet lemon-lime beverage. 500 ppm of sodium gluconate was then mixed with the base solution. The sweetness linger of this solution was determined to be 4.

Example G14

400 ppm of EBA was dissolved in a citric acid/potassium citrate composition equivalent to that in a diet lemon-lime beverage. 125-500 ppm of potassium tartrate monohydrate was then mixed with the base solution. The sweetness linger of this solution was determined to be 3.

Example G15

400 ppm of REBA was dissolved in a citric acid/potassium citrate composition equivalent to that in a diet lemon-lime beverage, 500 ppm of sodium tartrate dihydrate was then mixed with the base solution. The sweetness linger of this solution was determined to be 2.

Example G16

400 ppm of REBA was dissolved in a citric acid/potassium citrate composition equivalent to that in a diet lemon-lime beverage. 310-1,250 ppm of glucoheptonic acid, sodium salt was then mixed with the base solution. The sweetness linger of this solution was determined to be 2.

Example G17

400 ppm of REBA was dissolved in a citric acid/potassium citrate composition equivalent to that in a diet lemon-lime beverage. 250-500 ppm of L-sodium lactate was then mixed with the base solution. The sweetness linger of this solution was determined to be 3. This formulation was found to have sugar-like taste characteristics.

Example G18

400 ppm of REBA was dissolved in a citric acid/potassium citrate composition equivalent to that in a diet lemon-lime beverage. 1,000 ppm of L-sodium lactate was then mixed with the base solution. The sweetness linger of this solution was determined to be 2. This formulation was found to have sugar-like taste characteristics.

Example G19

400 ppm of REBA was dissolved in a citric acid/potassium citrate composition equivalent to that in a diet lemon-lime beverage. 600-800 ppm of malic acid was then mixed with the base solution. The sweetness linger of this solution was determined to be 3.

Example G20

400 ppm of REBA was dissolved in a citric acid/potassium citrate composition equivalent to that in a diet lemon-lime beverage. 500 ppm of hydroxycitric acid was then mixed with the base solution. The sweetness linger of this solution was determined to be 3.

Example G21

400 ppm of REBA was dissolved in a citric acid/potassium citrate composition equivalent to that in a diet lemon-lime beverage. 500 ppm of salicylic acid was then mixed with the base solution. The sweetness linger of this solution was determined to be 3.

Example G22

400 ppm of EBA was dissolved in a citric acid/potassium citrate composition equivalent to that in a diet lemon-lime beverage. 1,000 ppm of salicylic acid was then mixed with the base solution. The sweetness linger of this solution was determined to be 2.

Example G23

400 ppm of FBA was dissolved in a citric acid/potassium citrate composition equivalent to that in a diet lemon-lime beverage. 112 ppm of caffeic acid was then mixed with the base solution. The sweetness linger of this solution was determined to be 1.

Example G24

400 ppm of REBA was dissolved in a citric acid/potassium citrate composition equivalent to that in a diet lemon-lime beverage. 250 ppm of succinic acid was then mixed with the base solution. The sweetness linger of this solution was determined to be 3.

Example G25

400 ppm of REBA was dissolved in a citric acid/potassium citrate composition equivalent to that in a diet lemon-lime beverage. An 80:20 (wt/wt) ratio of citric acid/malic acid was then mixed with the base solution. The sweetness linger of this solution was determined to be 4.

Example G26

400 ppm of REBA was dissolved in a citric acid/potassium citrate composition equivalent to that in a diet lemon-lime beverage. 125 ppm of 2,4-dihydroxybenzoic acid was then mixed with the base solution. The sweetness linger of this solution was determined to be 2.

Example G27

400 ppm of EBA was dissolved in a citric acid/potassium citrate composition equivalent to that in a diet lemon-lime beverage. 250 ppm of 2,4-dihydroxybenzoic acid was then mixed with the base solution. The sweetness linger of this solution was determined to be 1.

Example G28

400 ppm of REBA was dissolved in a citric acid/potassium citrate composition equivalent to that in a diet lemon-lime beverage. 100 ppm of D/L alanine was then mixed with the base solution. The sweetness linger of this solution was determined to be 3.

Example G29

400 ppm of REBA was dissolved in a citric acid/potassium citrate composition equivalent to that in a diet lemon-lime beverage. 100 ppm of theanine was then mixed with the base solution. The sweetness linger of this solution was determined to be 1.

Example G30

400 ppm of REBA was dissolved in a citric acid/potassium citrate composition equivalent to that in a diet lemon-lime beverage. 5,000 ppm to 10,000 ppm of glycine was then mixed with the base solution. The sweetness linger of this solution was determined to be 3.

Example G31

400 ppm of REBA was dissolved in a citric acid/potassium citrate composition equivalent to that in a diet lemon-lime beverage. 2,500 ppm of creatine was then mixed with the base solution. The sweetness linger of this solution was determined to be 2. This formulation was found to have sugar-like taste characteristics.

Example G32

400 ppm of REBA was dissolved in a citric acid/potassium citrate composition equivalent to that in a diet lemon-lime beverage. 620 ppm to 5,000 ppm of L-serine was then mixed with the base solution. The sweetness linger of this solution was determined to be 2. This formulation was found to have sugar-like taste characteristics.

Example G33

400 ppm of REBA was dissolved in a citric acid/potassium citrate composition equivalent to that in a diet lemon-lime beverage. 1,250 ppm to 2,500 ppm of glucosamine hydrochloride was then mixed with the base solution. The sweetness linger of this solution was determined to be 3. This formulation was found to have sugar-like taste characteristics.

Example G34

400 ppm of REBA was dissolved in a citric acid/potassium citrate composition equivalent to that in a diet lemon-lime beverage. 2,500 ppm to 5,000 ppm of taurine was then mixed with the base solution. The sweetness linger of this solution was determined to be 3.

Example G35

400 ppm of REBA was dissolved in a citric acid/potassium citrate composition equivalent to that in a diet lemon-lime beverage. 1,000 ppm to 2,000 ppm of polypropylene glycol alginate (PGA) was then mixed with the base solution. The sweetness linger of this solution was determined to be 5. This formulation was found to have sugar-like taste characteristics.

Example G36

Two solutions were prepared. In each, 400 ppm of REBA was dissolved in a citric acid/potassium citrate composition equivalent to that in a diet lemon-lime beverage. 78 ppm to 156 ppm and 1,250 ppm of soluble rice protein were then mixed with the respective base solutions. The sweetness linger of these solutions was determined to be 3. This formulation was found to have sugar-like taste characteristics.

Example G37

400 ppm of REBA was dissolved in a citric acid/potassium citrate composition equivalent to that in a diet lemon-lime beverage. 312 ppm to 625 ppm of soluble rice protein was then mixed with the base solution. The sweetness linger of this solution was determined to be 2. This formulation was found to have sugar-like taste characteristics.

Example G38

400 ppm of REBA was dissolved in a citric acid/potassium citrate composition equivalent to that in a diet lemon-lime beverage. 25 ppm of naringin was then mixed with the base solution. The sweetness linger of this solution was determined to be 2.

Example G39

400 ppm of REBA was dissolved in a citric acid/potassium citrate composition equivalent to that in a diet lemon-lime beverage. 1.2 ppm of quinine was then mixed with the base solution. The sweetness linger of this solution was determined to be 4.

Example G40 ppm of REBA was dissolved in a citric acid/potassium citrate composition equivalent to that in a diet lemon-lime beverage. 125 ppm of enzyme modified rutin Sanmelin™ AO (San-E1 Gen F.F.I., Inc., Osaka, Japan) was then mixed with the base solution. The sweetness linger of this solution was determined to be 4. This formulation was found to have sugar-like taste characteristics.

Example G41

400 ppm of REBA was dissolved in a citric acid/potassium citrate composition equivalent to that in a diet lemon-lime beverage. 250 ppm of enzyme modified rutin Sanmelin™ AO (San-Ei Gen F.F.I., Inc., Osaka, Japan) was then mixed with the base solution. The sweetness linger of this solution was determined to be 3. This formulation was found to have sugar-like taste characteristics.

Example G42

400 ppm of REBA was dissolved in a citric acid/potassium citrate composition equivalent to that in a diet lemon-lime beverage. 1.2 ppm of viridiflorol was then mixed with the base solution. The sweetness linger of this solution was determined to be 2.

Example G43

400 ppm of REBA was dissolved in a citric acid/potassium citrate composition equivalent to that in a diet lemon-lime beverage. 625 ppm of grape skin extract was then mixed with the base solution. The sweetness linger of this solution was determined to be 4. This formulation was found to have sugar-like taste characteristics.

Example G44

400 ppm of REBA was dissolved in a citric acid/potassium citrate composition equivalent to that in a diet lemon-lime beverage. 625 ppm of Symrise™ Natural Flavor Mask for Sweeteners, 164126 (Symrise™, Holzminden, Germany) was then mixed with the base solution. The sweetness linger of this solution was determined to be 4. This formulation was found to have sugar-like taste characteristics.

Example G45

400 ppm of REBA was dissolved in a citric acid/potassium citrate composition equivalent to that in a diet lemon-lime beverage. 1,250 ppm to 2,500 ppm of Symrise™ Natural Flavor Mask for Sweeteners 164126 (Symrise™, Holzminden, Germany) was then mixed with the base solution. The sweetness linger of this solution was determined to be 3. This formulation was found to have sugar-like taste characteristics.

Example G46

400 ppm of REBA was dissolved in a citric acid/potassium citrate composition equivalent to that in a diet lemon-lime beverage. 2 ppm of Natural Advantage™ Bitterness Blocker 9 (Natural Advantage, Freehold, N.J., U.S.A.) was then mixed with the base solution. The sweetness linger of this solution was determined to be 2. This formulation was found to have sugar-like taste characteristics.

Example G47

400 ppm of REBA was dissolved in a citric acid/potassium citrate composition equivalent to that in a diet lemon-lime beverage. 1 ppm to 2 ppm of Natural Advantage™ Bitterness Blocker 2 Natural Advantage, Freehold, N.J., U.S.A.) was then mixed with the base solution. The sweetness linger of this solution was determined to be 2.

Example G48

400 ppm of REBA was dissolved in a citric acid/potassium citrate composition equivalent to that in a diet lemon-lime beverage. 2 ppm of Natural Advantage™ Bitterness Blocker 1 (Natural Advantage, Freehold, N.J., U.S.A.) was then mixed with the base solution. The sweetness linger of this solution was determined to be 3.

Example G49

400 ppm of REBA was dissolved in a citric acid/potassium citrate composition equivalent to that in a diet lemon-lime beverage. 4 ppm to 8 ppm of Natural Advantage™ Bitterness Blocker 10 Natural Advantage, Freehold, N.J., U.S.A.) was then mixed with the base solution. The sweetness linger of this solution was determined to be 2.

Example G50

400 ppm of REBA was dissolved in a citric acid/potassium citrate composition equivalent to that in a diet lemon-lime beverage. 25 ppm of AMP was then mixed with the base solution. The sweetness linger of this solution was determined to be 3.

EXAMPLE SET H

Sweet taste improving compositions were combined with a REBA solution to determine their effect on sweetness linger. Screening of the initial sample, or further dilutions, allowed identification of concentrations which were just above-threshold, herein defined as "near-threshold concentrations." The near-threshold additive concentrations, a 6- to 100-fold higher higher additive concentration (depending on the off-taste intensity), and a mid-level additive concentration (halfway between the near-threshold and higher additive concentration) were evaluated to determine the effect on sweetness linger of a REBA solution.

Formulations of a 500 ppm REBA in a phosphoric acid solution (75%) at a pH of 2.5 with phosphoric acid or a pH of 3.1 with citric acid and potassium citrate were prepared prior to the addition of the additives at the three levels of concentration.

Sensory evaluation using the protocol described in Example Set G then was used to evaluate the sweetness linger of the REBA solutions.

Controls

- 500 ppm of EBA was dissolved in one liter of carbon-treated water and phosphoric acid (75%) was added until a pH between 2.4 and 2.5 was reached. The sweetness linger rating of this control sample was determined to be 5.
- 10 g of sugar was dissolved in 100 ml of carbon treated water and phosphoric acid (75%) was added until a pH between 2.4 and 2.5 was reached. The sweetness linger rating of this control sample was determined to be 0.

The following Examples H 1-42 illustrate combinations of rebaudioside A and sweet taste improving compositions in accordance with particular embodiments of this invention.

Example H1

500 ppm of REBA was dissolved in one liter carbon-treated water and phosphoric acid (75%), was added until a pH between pH 2.4 and 2.5 was reached. 5,000 ppm of D-fructose was then mixed with the base solution. The sweetness linger of this solution was determined to be 3. This formulation was found to have sugar-like taste characteristics.

Example H2

500 ppm of REBA was dissolved in one liter carbon-treated water and phosphoric acid (75%) was added until a pH between pH 2.4 and 2.5 was reached. 1,000 ppm of Fructooligosaccharide (55%) was then mixed with the base solution. The sweetness linger of this solution was determined to be 3. This formulation was found to have sugar-like taste characteristics.

Example H3

500 ppm of REBA was dissolved in one liter carbon-treated water and phosphoric acid (75%) was added until a pH between pH 2.4 and 2.5 was reached. 5,000 ppm of D-fructose was then mixed with the base solution. The sweetness linger of this solution was determined to be 2.

Example H4

500 ppm of REBA was dissolved in one liter carbon-treated water and phosphoric acid (75%) was added until a pH between pH 2.4 and 2.5 was reached. 450 ppm of KCl and 680 ppm of $KH_2PO_4$ were then mixed with the base solution. The sweetness linger of this solution was determined to be 3. This formulation was found to have sugar-like taste characteristics.

Example H5

500 ppm of REBA was dissolved in one liter carbon-treated water and phosphoric acid (75%) was added until a pH between pH 2.4 and 2.5 was reached. 250 ppm to 2,500 ppm of potassium benzoate was then mixed with the base solution. The sweetness linger of this solution was determined to be 4.

Example H6

500 ppm of REBA was dissolved in one liter carbon-treated water and phosphoric acid (75%) was added until a pH between pH 2.4 and 2.5 was reached. 150 ppm to 200 ppm of malic acid was then mixed with the base solution. The sweetness linger of this solution was determined to be 3.

Example H7

500 ppm of REBA was dissolved in one liter carbon-treated water and phosphoric acid (75%) was added until a pH between pH 2.4 and 2.5 was reached. 50 ppm to 200 ppm of citric acid was then mixed with the base solution. The sweetness linger of this solution was determined to be 3.

Example H8

500 ppm of REBA was dissolved in one liter carbon-treated water and phosphoric acid (75%) was added until a pH between pH 2.4 and 2.5 was reached. 1,171 ppm of citric acid was then mixed with the base solution. The sweetness linger of this solution was determined to be 3.

Example H9

500 ppm of REBA was dissolved in one liter carbon-treated water and phosphoric acid (75%) was added until a pH between pH 2.4 and 2.5 was reached. 50 ppm to 1,400 ppm of adipic acid was then mixed with the base solution. The sweetness linger of this solution was determined to be 3. This formulation was found to have sugar-like taste characteristics.

Example H10

500 ppm of REBA was dissolved in one liter carbon-treated water and phosphoric acid (75%) was added until a pH between pH 2.4 and 2.5 was reached. 1,400 ppm of adipic acid was then mixed with the base solution. The sweetness linger of this solution was determined to be 2. This formulation was found to have sugar-like taste characteristics.

Example H11

500 ppm of EBA was dissolved in one liter carbon-treated water and phosphoric acid (75%) was added until a pH between pH 2.4 and 2.5 was reached. 608 ppm of 6.2 mM phosphoric acid was then mixed with the base solution. The sweetness linger of this solution was determined to be 1.

Example H12

500 ppm of EBA was dissolved in one liter carbon-treated water and phosphoric acid (75%) was added until a pH between pH 2.4 and 2.5 was reached. 666 ppm of 6.8 mM phosphoric acid was then mixed with the base solution. The sweetness linger of this solution was determined to be 1.

Example H13

500 ppm of REBA was dissolved in one liter carbon-treated water and phosphoric acid (75%) was added until a pH between pH 2.4 and 2.5 was reached. 500 ppm to 2,000 ppm of potassium benzoate was then mixed with the base solution. The sweetness linger of this solution was determined to be 4.

Example H14

500 ppm of REBA was dissolved in one liter carbon-treated water and phosphoric acid (75%) was added until a pH between pH 2.4 and 2.5 was reached. 5,000 ppm of L-α aminobutyric acid was then mixed with the base solution. The sweetness linger of this solution was determined to be 3. This formulation was found to have sugar-like taste characteristics.

Example H15

500 ppm of EBA was dissolved in one liter carbon-treated water and phosphoric acid (75%) was added until a pH between pH 2.4 and 2.5 was reached. 5,000 ppm of 4-hydroxy-L-proline was then mixed with the base solution. The sweetness linger of this solution was determined to be 3. This formulation was found to have sugar-like taste characteristics.

Example H16

500 ppm of REBA was dissolved in one liter carbon-treated water and phosphoric acid (75%) was added until a pH between pH 2.4 and 2.5 was reached. 5,000 ppm of L-glutamine was then mixed with the base solution. The sweetness linger of this solution was determined to be 4. This formulation was found to have sugar-like taste characteristics.

Example H17

500 ppm of REBA was dissolved in one liter carbon-treated water and phosphoric acid (75%) was added until a pH between pH 2.4 and 2.5 was reached. 15,000 ppm of glycine was then mixed with the base solution. The sweetness linger of this solution was determined to be 1. This formulation was found to have sugar-like taste characteristics.

Example H18

500 ppm of REBA was dissolved in one liter carbon-treated water and phosphoric acid (75%) was added until a pH between pH 2.4 and 2.5 was reached. 3,750 ppm of glycine was then mixed with the base solution. The sweetness linger of this solution was determined to be 3.5. This formulation was found to have sugar-like taste characteristics.

Example H19

500 ppm of REBA was dissolved in one liter carbon-treated water and phosphoric acid (75%) was added until a pH between pH 2.4 and 2.5 was reached. 7,000 ppm of glycine was then mixed with the base solution. The sweetness linger of this solution was determined to be 2. This formulation was found to have sugar-like taste characteristics.

Example H20

500 ppm of REBA was dissolved in one liter carbon-treated water and phosphoric acid (75%) was added until a pH between pH 2.4 and 2.5 was reached. 5,000 ppm of L-alanine was then mixed with the base solution. The sweetness linger of this solution was determined to be 2. This formulation was found to have sugar-like taste characteristics.

Example H21

Two solutions were prepared. In each, 500 ppm of REBA was dissolved in one liter carbon-treated water and phosphoric acid (75%) was added until a pH between pH 2.4 and 2.5 was reached. 2,500 ppm and 7,000 ppm to 10,000 ppm of L-alanine were then mixed with the respective base solutions. The sweetness linger of these solutions was determined to be 3. This formulation was found to have sugar-like taste characteristics.

Example H22

Two solutions were prepared. In each, 500 ppm of REBA was dissolved in one liter carbon-treated water and phosphoric acid (75%) was added until a pH between pH 2.4 and 2.5 was reached. 2,500 ppm and 10,000 ppm of β-alanine were then mixed with the respective base solutions. The sweetness linger of these solutions was determined to be 2. This formulation was found to have sugar-like taste characteristics.

Example H23

500 ppm of REBA was dissolved in one liter carbon-treated water and phosphoric acid (75%) was added until a pH between pH 2.4 and 2.5 was reached. 5,000 ppm of β-alanine was then mixed with the base solution. The sweetness linger of this solution was determined to be 3. This formulation was found to have sugar-like taste characteristics.

Example H24

500 ppm of REBA was dissolved in one liter carbon-treated water and phosphoric acid (75%) was added until a pH between pH 2.4 and 2.5 was reached. 5,000 ppm of glycine and 2,500 ppm of L-alanine was then mixed with the base solution. The sweetness linger of this solution was determined to be 2. This formulation was found to have sugar-like taste characteristics.

Example H25

500 ppm of REBA was dissolved in one liter carbon-treated water and phosphoric acid (75%) was added until a pH between pH 2.4 and 2.5 was reached. 3,750 ppm of glycine and 3,750 ppm of L-alanine was then mixed with the base solution. The sweetness linger of this solution was determined to be 2. This formulation was found to have sugar-like taste characteristics.

Example H26

500 ppm of REBA was dissolved in one liter carbon-treated water and phosphoric acid (75%) was added until a pH between pH 2.4 and 2.5 was reached. 7,500 ppm of L-alanyl-L-glutamine was then mixed with the base solution. The sweetness linger of this solution was determined to be 3. This formulation was found to have sugar-like taste characteristics.

Example H27

500 ppm of REBA was dissolved in one liter carbon-treated water and phosphoric acid (75%) was added until a pH between pH 2.4 and 2.5 was reached. 15,000 ppm of glycine and 375 ppm of $KAl(SO_4)_2 \cdot 12H_2O$ (Alum) were then mixed with the base solution. The sweetness linger of this solution was determined to be 2. This formulation was found to have sugar-like taste characteristics.

Example H28

500 ppm of REBA was dissolved in one liter carbon-treated water and phosphoric acid (75%) was added until a pH between pH 2.4 and 2.5 was reached. 1,500 ppm of urea and 584 ppm of sodium chloride were then mixed with the base solution. The sweetness linger of this solution was determined to be 3. This formulation was found to have sugar-like taste characteristics.

Example H29

500 ppm of REBA was dissolved in one liter carbon-treated water and phosphoric acid (75%) was added until a pH between pH 2.4 and 2.5 was reached. 3,750 ppm of glycine and 60 ppm to 90 ppm of poly-L-α-lysine were then mixed with the base solution. The sweetness linger of this solution was determined to be 3. This formulation was found to have sugar-like taste characteristics.

Example H30

500 ppm of REBA was dissolved in one liter carbon-treated water and phosphoric acid (75%) was added until a pH between pH 2.4 and 2.5 was reached. 3,750 ppm of glycine and 10 ppm of poly-L-ε-lysine were then mixed with the base solution. The sweetness linger of this solution was determined to be 3. This formulation was found to have sugar-like taste characteristics.

Example H31

500 ppm of REBA was dissolved in one liter carbon-treated water and phosphoric acid (75%) was added until a pH between pH 2.4 and 2.5 was reached. 3,750 ppm of glycine and 119 ppm of potassium chloride were then mixed with the base solution. The sweetness linger of this solution was determined to be 4. This formulation was found to have sugar-like taste characteristics.

Example H32

500 ppm of REBA was dissolved in one liter carbon-treated water and phosphoric acid (75%) was added until a pH between pH 2.4 and 2.5 was reached. 15,000 ppm of glycine and 239 ppm of potassium chloride were then mixed with the base solution. The sweetness linger of this solution was determined to be 2. This formulation was found to have sugar-like taste characteristics.

Example H33

500 ppm of REBA was dissolved in one liter carbon-treated water and phosphoric acid (75%) was added until a pH between pH 2.4 and 2.5 was reached. 3,750 ppm of glycine and 238 ppm of sodium chloride were then mixed with the base solution. The sweetness linger of this solution was determined to be 4. This formulation was found to have sugar-like taste characteristics.

Example H34

500 ppm of REBA was dissolved in one liter carbon-treated water and phosphoric acid (75%) was added until the pH was reached between pH 2.4 and 2.5. 3,750 ppm of glycine, 43 ppm of NaCl and 51 ppm of KCl were then mixed with the base solution. The sweetness linger of this solution was determined to be 4. This formulation was found to have sugar-like taste characteristics.

Example H35

500 ppm of REBA was dissolved in one liter carbon-treated water and phosphoric acid (75%) was added until a pH between pH 2.4 and 2.5 was reached. 15,000 ppm of glycine and 501 ppm of sodium gluconate were then mixed with the base solution. The sweetness linger of this solution was determined to be 2. This formulation was found to have sugar-like taste characteristics.

Example H36

500 ppm of REBA was dissolved in one liter carbon-treated water and phosphoric acid (75%) was added until a pH between pH 2.4 and 2.5 was reached. 2,500 ppm of L-alanine and 5,000 ppm of fructose were then mixed with the base solution. The sweetness linger of this solution was determined to be 4. This formulation was found to have sugar-like taste characteristics.

Example H37

500 ppm of REBA was dissolved in one liter carbon-treated water and phosphoric acid (75%) was added until a pH between pH 2.4 and 2.5 was reached. 3,750 ppm of glycine and 35,000 ppm of erythritol were then mixed with the base solution. The sweetness linger of this solution was determined to be 2. This formulation was found to have sugar-like taste characteristics.

Example H38

500 ppm of REBA was dissolved in one liter carbon-treated water and phosphoric acid (75%) was added until a pH between pH 2.4 and 2.5 was reached. 35,000 ppm of erythritol, 3,750 ppm of glycine, 450 ppm of KCl, 680 ppm of $KH_2PO_4$, and 1,175 ppm of choline chloride were then mixed with the base solution. The sweetness linger of this solution was determined to be 1. This formulation was found to have sugar-like taste characteristics.

Example H39

500 ppm of REBA was dissolved in one liter carbon-treated water and phosphoric acid (75%) was added until a pH between pH 2.4 and 2.5 was reached. 2,500 ppm of L-alanine, 5,000 ppm of fructose, and 35,000 ppm of erythritol were then mixed with the base solution. The sweetness linger of this solution was determined to be 4. This formulation was found to have sugar-like taste characteristics.

Example H40

500 ppm of EBA was dissolved in one liter carbon-treated water and phosphoric acid (75%) was added until a pH between pH 2.4 and 2.5 was reached. 35,000 ppm of erythritol, 3,750 ppm of glycine, 450 ppm of KCl, and 680 ppm of $KH_2PO_4$ were then mixed with the base solution. The sweetness linger of this solution was determined to be 4. This formulation was found to have sugar-like taste characteristics.

Example H41

360 ppm of REBA was dissolved in one liter carbon-treated water and phosphoric acid (75%) was added until a pH between pH 2.4 and 2.5 was reached. 400 ppm of Fibergum and 35,000 ppm of erythritol were then mixed with the base solution. The sweetness linger of this solution was determined to be 2.

Example H42

500 ppm of REBA was dissolved in one liter carbon-treated water and phosphoric acid (75%) was added until a pH between pH 2.4 and 2.5 was reached. 10,000 ppm to 20,000 ppm of $KH_2PO_4$ was then mixed with the base solution. The sweetness linger of this solution was determined to be 2.

While the invention has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereof.

We claim:

1. A functional sweetener composition comprising at least one functional ingredient, rebaudioside A and erythritol, wherein:
   the rebaudioside A has a purity greater than about 97% by weight on a dry basis;
   the weight ratio of rebaudioside A to erythritol is about 1:75 to about 1:150; and
   the at least one functional ingredient is selected from the group consisting of bismuth, boron, calcium, chlorine, chromium, cobalt, copper, fluorine, iodine, iron, lithium, magnesium, manganese, molybdenum, nickel, phosphorous, potassium, rubidium, selenium, silicon, sodium, strontium, sulfur, tellurium, tin, titanium, tungsten, vanadium, zinc or combinations thereof.

2. The functional sweetener composition of claim 1, wherein the rebaudioside A has a purity greater than about 99% by weight on a dry basis.

3. The functional sweetener composition of claim 1, further comprising at least one steviolglycoside selected from the group consisting of rebaudioside B, rebaudioside C, rebaudioside E, rebaudioside F, dulcoside A, dulcoside B, stevioside, steviolbioside or combinations thereof.

4. The functional sweetener composition of claim 1, wherein the rebaudioside A is substantially free of steviolbioside as measured by HPLC.

5. The functional sweetener composition of claim 1, wherein the rebaudioside A has a rate of dissolution greater than about 30%/5 minutes in water at 25° C.

6. The functional sweetener composition of claim 1, further comprising at least one sweet taste improving composition selected from the group consisting of carbohydrates, amino acids and their corresponding salts, polyamino acids and their corresponding salts, sugar acids and their corresponding salts, organic acids, inorganic acids, organic salts, inorganic salts, bitter compounds, flavorants, astringent compounds, polymers, proteins, protein hydrolysates, surfactants, emulsifiers, flavonoids, alcohols, synthetic sweeteners or combinations thereof.

7. A functional sweetened composition comprising a sweetenable composition and a functional sweetener composition comprising at least one functional ingredient, rebaudioside A and erythritol, wherein:
the rebaudioside A has a purity greater than about 97% by weight on a dry basis;
the weight ratio of rebaudioside A to erythritol is about 1:75 to about 1:150; and
the at least one functional ingredient is selected from the group consisting of bismuth, boron, calcium, chlorine, chromium, cobalt, copper, fluorine, iodine, iron, lithium, magnesium, manganese, molybdenum, nickel, phosphorous, potassium, rubidium, selenium, silicon, sodium, strontium, sulfur, tellurium, tin, titanium, tungsten, vanadium, zinc or combinations thereof.

8. The functional sweetened composition of claim 7, wherein the rebaudioside A has a purity greater than about 99% by weight on a dry basis.

9. The functional sweetened composition of claim 7, wherein the rebaudioside A is present in an amount from about 100 ppm to about 3,000 ppm.

10. The functional sweetened composition of claim 7, wherein the erythritol is present in an amount from about 5,000 ppm to about 40,000 ppm.

11. The functional sweetened composition of claim 7, further comprising at least one steviolglycoside selected from the group consisting of rebaudioside B, rebaudioside C, rebaudioside E, rebaudioside F, dulcoside A, dulcoside B, stevioside, steviolbioside or combinations thereof.

12. The functional sweetened composition of claim 7, wherein the rebaudioside A is substantially free of steviolbioside as measured by HPLC.

13. The functional sweetened composition of claim 7, wherein the rebaudioside A has a rate of dissolution greater than about 30% 15 minutes in water at 25° C.

14. The functional sweetened composition of claim 7, further comprising at least one sweet taste improving composition selected from the group consisting of carbohydrates, amino acids and their corresponding salts, polyamino acids and their corresponding salts, sugar acids and their corresponding salts, organic acids, inorganic acids, organic salts, inorganic salts, bitter compounds, flavorants, astringent compounds, polymers, proteins, protein hydrolysates, surfactants, emulsifiers, flavonoids, alcohols, synthetic sweeteners or combinations thereof.

15. The functional sweetened composition of claim 7, wherein the sweetenable composition is a beverage selected from the group consisting of a noncarbonated beverage, carbonated beverage, cola, root beer, fruit-flavored beverage, citrus-flavored beverage, fruit juice, fruit-containing beverage, vegetable juice, vegetable containing beverage, tea, coffee, dairy beverage, sports drink, energy drink, and flavored water.

* * * * *